(12) United States Patent
King

(10) Patent No.: US 11,027,096 B2
(45) Date of Patent: Jun. 8, 2021

(54) FLEXIBLE CIRCUIT BEARING A TRACKABLE LOW-FREQUENCY ELECTROMAGNETIC COIL

(71) Applicant: Lucent Medical Systems, Inc., Kirkland, WA (US)

(72) Inventor: Curtis S. King, Kirkland, WA (US)

(73) Assignee: LUCENT MEDICAL SYSTEMS, INC., Kirkland, WA (US)

( * ) Notice: Subject to any disclaimer, the term of this patent is extended or adjusted under 35 U.S.C. 154(b) by 746 days.

(21) Appl. No.: 15/911,006

(22) Filed: Mar. 2, 2018

(65) Prior Publication Data

US 2019/0054274 A1 Feb. 21, 2019

Related U.S. Application Data

(60) Provisional application No. 62/548,131, filed on Aug. 21, 2017.

(51) Int. Cl.
*A61M 25/01* (2006.01)
*A61B 5/06* (2006.01)
*A61M 25/00* (2006.01)

(52) U.S. Cl.
CPC ......... *A61M 25/0127* (2013.01); *A61B 5/062* (2013.01); *A61M 25/0012* (2013.01); *A61B 2562/12* (2013.01); *A61B 2562/222* (2013.01); *A61M 2025/0166* (2013.01); *A61M 2205/502* (2013.01)

(58) Field of Classification Search
CPC .......... A61M 25/0127; A61M 25/0012; A61M 2025/0166; A61M 2205/502; A61B 5/062; A61B 2562/222; A61B 2562/12
See application file for complete search history.

(56) References Cited

U.S. PATENT DOCUMENTS

| 5,425,367 A | 6/1995 | Shapiro et al. |
| 5,425,382 A | 6/1995 | Golden et al. |
| 5,622,169 A | 4/1997 | Golden et al. |
| 5,645,065 A | 7/1997 | Shapiro et al. |
| 5,767,669 A | 6/1998 | Hansen et al. |
| 5,775,322 A | 7/1998 | Silverstein et al. |
| 5,879,297 A | 3/1999 | Haynor et al. |
| 5,902,238 A | 5/1999 | Golden et al. |
| 6,129,668 A | 10/2000 | Haynor et al. |

(Continued)

OTHER PUBLICATIONS

Amphenol® RF, "Frequency Range Chart," archived Nov. 9, 2015, URL=https://web.archive.org/web/20151109154937/http://www.amphenolrf.com/frequency-range-chart/, download date Mar. 15, 2017, 3 pages.

(Continued)

*Primary Examiner* — Sanjay Cattungal
(74) *Attorney, Agent, or Firm* — Seed IP Law Group LLP

(57) ABSTRACT

A medical system tracks the position of a medical instrument within a body of a patient. The medical instrument includes an elongated flexible printed circuit and an electromagnet structure having a conductive coil wound around a core. A control circuit applies an excitation signal across the conductive coil. Electrical current running through the conductive coil (wound around the core) generates a magnetic field. A plurality of sensors sense parameters of the magnetic field and output sensor signals. The control circuit calculates the position of the medical instrument based on the sensor signals.

34 Claims, 33 Drawing Sheets

(56) References Cited

U.S. PATENT DOCUMENTS

| | | | |
|---|---|---|---|
| 6,173,715 B1 | 1/2001 | Sinanan et al. | |
| 6,216,028 B1 | 4/2001 | Haynor et al. | |
| 6,263,230 B1 | 7/2001 | Haynor et al. | |
| 6,292,680 B1 | 9/2001 | Somogyi et al. | |
| 7,158,754 B2 | 1/2007 | Anderson | |
| 7,976,518 B2 | 7/2011 | Shaughnessy et al. | |
| 8,197,494 B2 | 6/2012 | Jaggi et al. | |
| 8,265,732 B2 | 9/2012 | Besz et al. | |
| 8,478,382 B2 | 7/2013 | Burnside et al. | |
| 8,606,347 B2 | 12/2013 | Besz et al. | |
| 8,644,907 B2 * | 2/2014 | Hartmann | A61B 17/1615 600/424 |
| 8,781,555 B2 * | 7/2014 | Burnside | A61B 8/0833 600/424 |
| 8,934,960 B2 | 1/2015 | Besz et al. | |
| 9,028,441 B2 | 5/2015 | Kuhn | |
| 9,131,956 B2 | 9/2015 | Shaughnessy et al. | |
| 9,579,488 B2 | 2/2017 | Shaughnessy et al. | |
| 9,585,599 B2 | 3/2017 | Besz et al. | |
| 9,687,174 B2 | 6/2017 | Jaggi et al. | |
| 2002/0165448 A1 * | 11/2002 | Ben-Haim | A61N 1/36564 600/424 |
| 2003/0006759 A1 | 1/2003 | Govari | |
| 2004/0087877 A1 | 5/2004 | Besz et al. | |
| 2008/0004663 A1 | 1/2008 | Jorgenson | |
| 2009/0171190 A1 | 7/2009 | Uchiyama et al. | |
| 2012/0130228 A1 | 5/2012 | Zellers et al. | |
| 2012/0130229 A1 | 5/2012 | Zellers et al. | |
| 2014/0051983 A1 | 2/2014 | Schroeder et al. | |
| 2014/0196723 A1 | 7/2014 | Kirkpatrick et al. | |
| 2015/0238388 A1 | 8/2015 | Kuhn | |
| 2016/0067148 A1 | 3/2016 | Nordquist et al. | |
| 2017/0128701 A1 | 5/2017 | Shaughnessy et al. | |
| 2017/0143235 A1 | 5/2017 | Besz et al. | |

OTHER PUBLICATIONS

International Search Report, dated Apr. 7, 2017, for International Application No. PCT/US2017/014395, 2 pages.

Sacolick et al., "Electromagnetically tracked placement of a peripherally inserted central catheter,"*SPIE Medical Imaging Proceedings*, 2004, 5 pages.

U.S. Appl. No. 16/071,891, filed Jul. 20, 2018, Low-Frequency Electromagnetic Tracking.

U.S. Appl. No. 15/820,209, filed Nov. 21, 2017, Connector and Methods for Making and Using the Connector.

U.S. Appl. No. 15/820,001, filed Nov. 21, 2017, Accuracy Testing of Electromagnetic Device Tracking.

U.S. Appl. No. 15/911,003, filed Mar. 2, 2018, Wireless Electromagnetic Navigational Element.

* cited by examiner

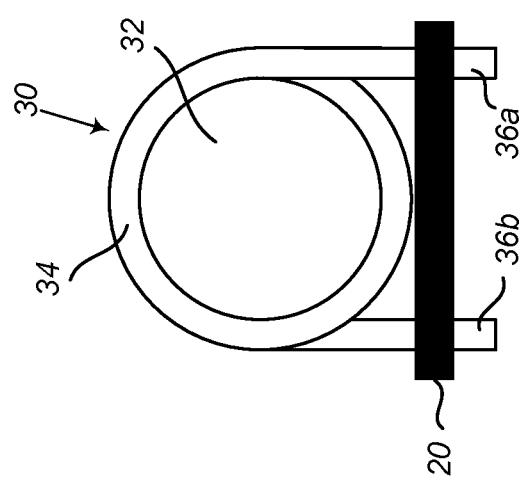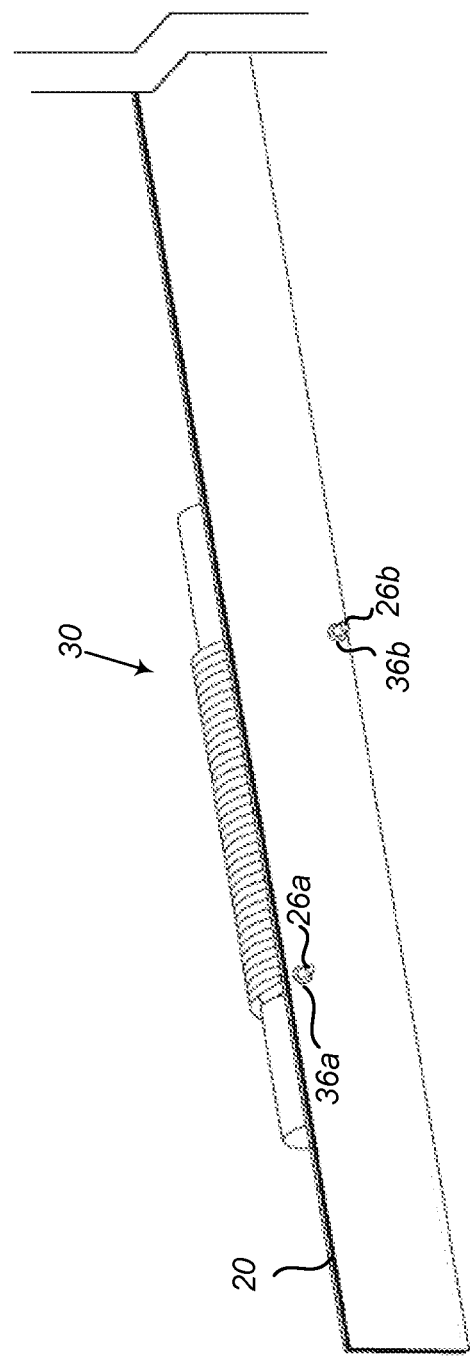

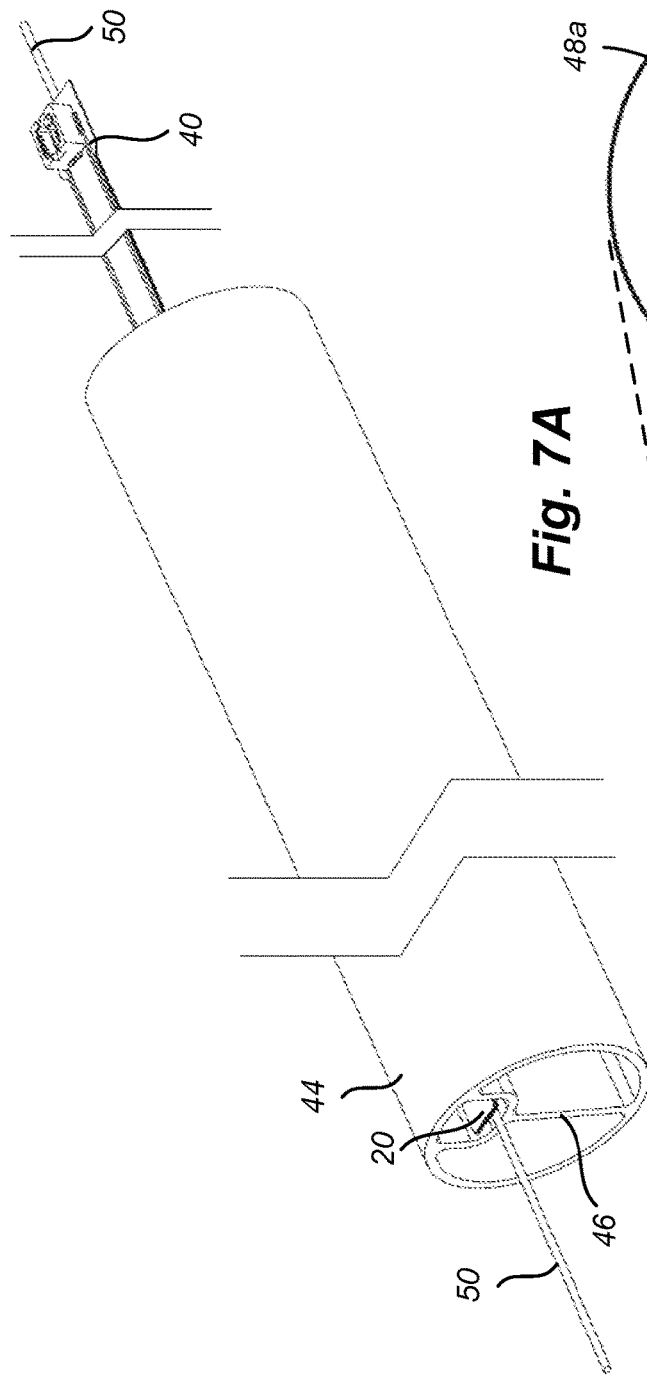
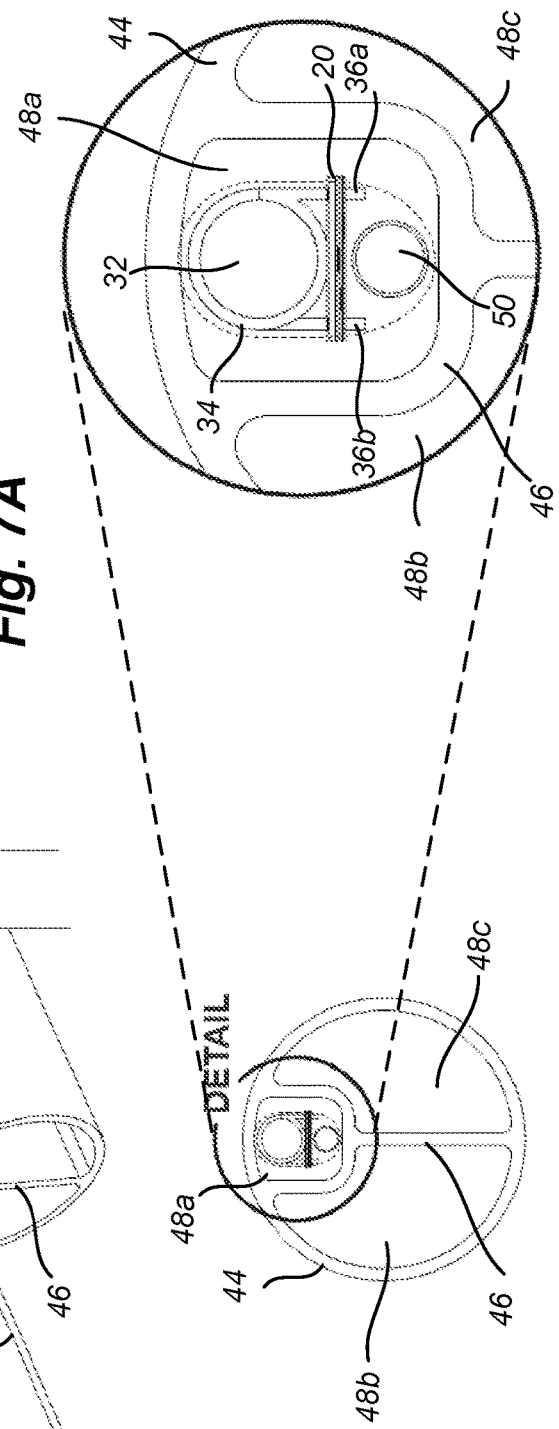
Fig. 7A
Fig. 7B
Fig. 7C

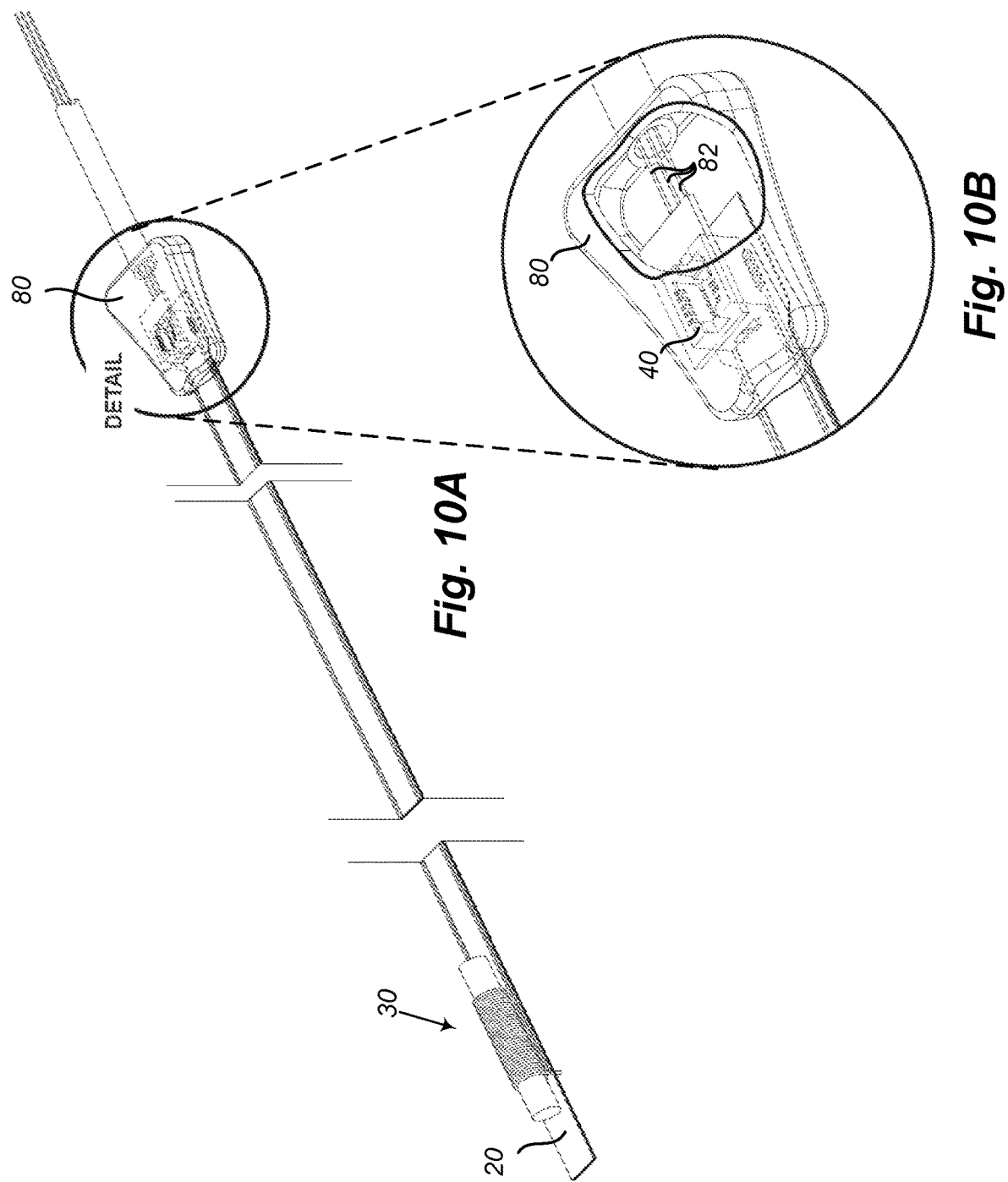

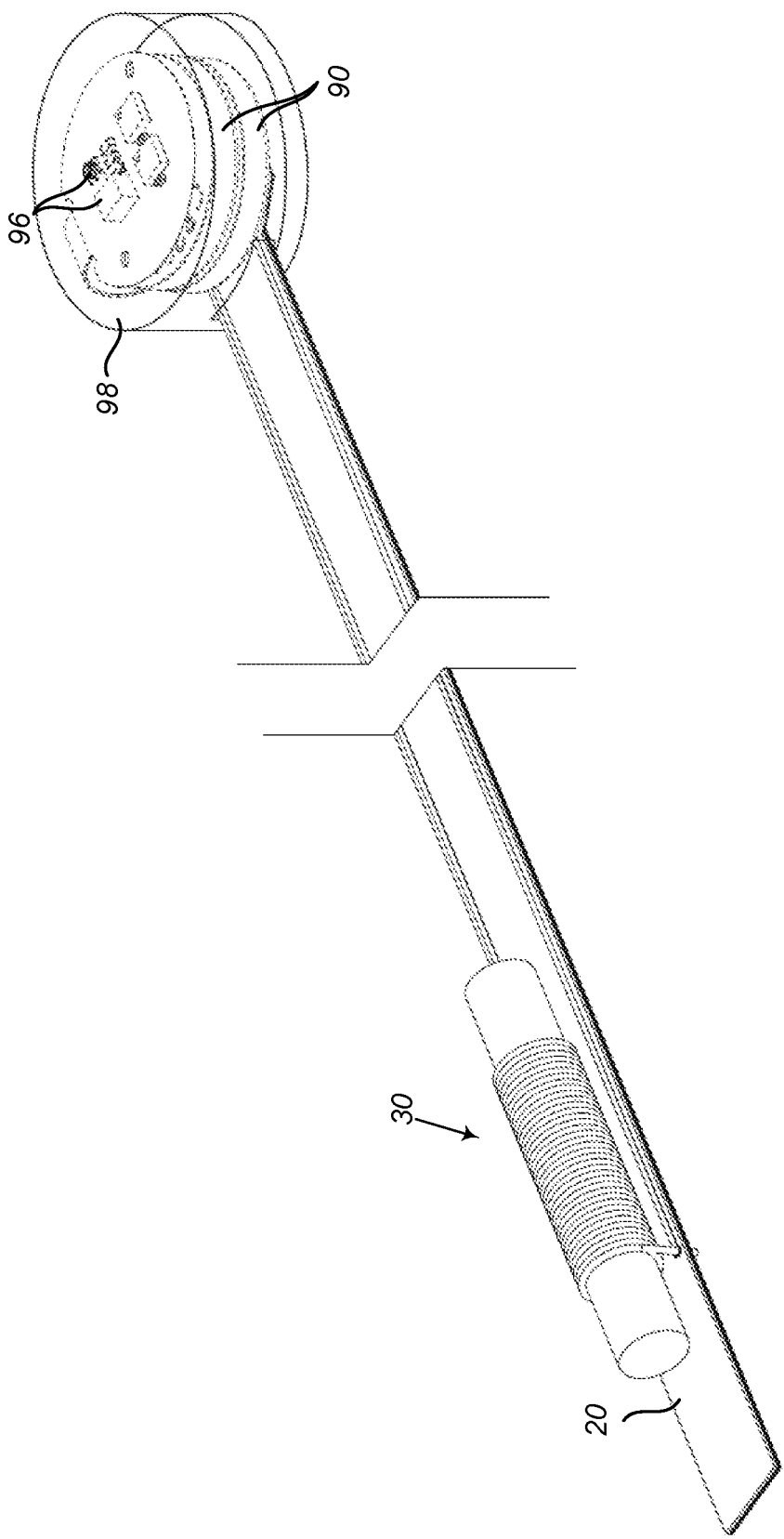

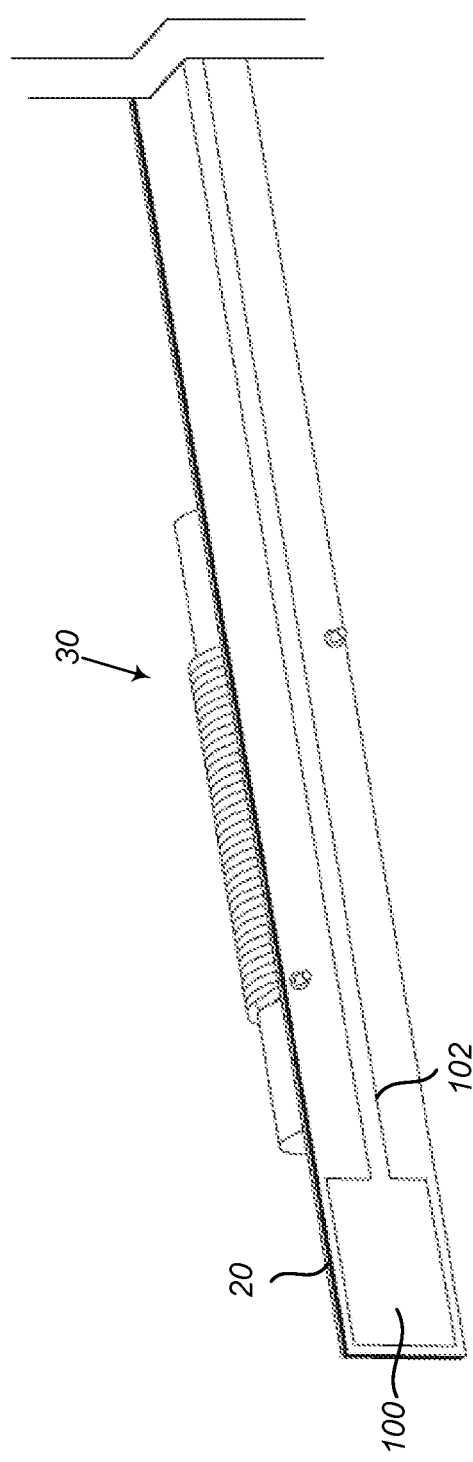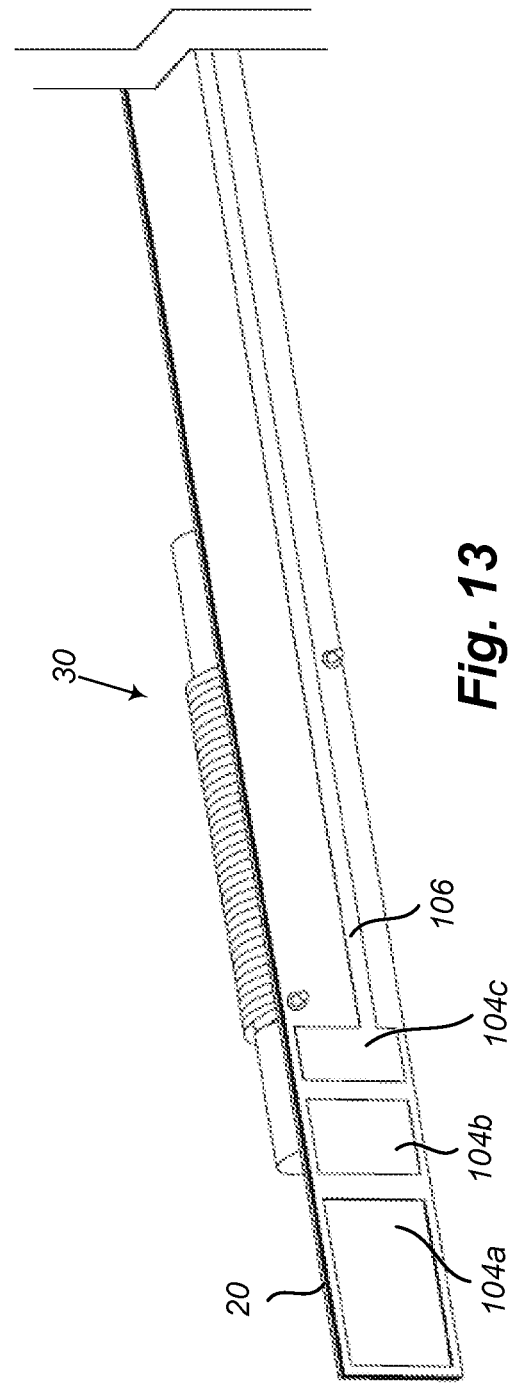
Fig. 12
Fig. 13

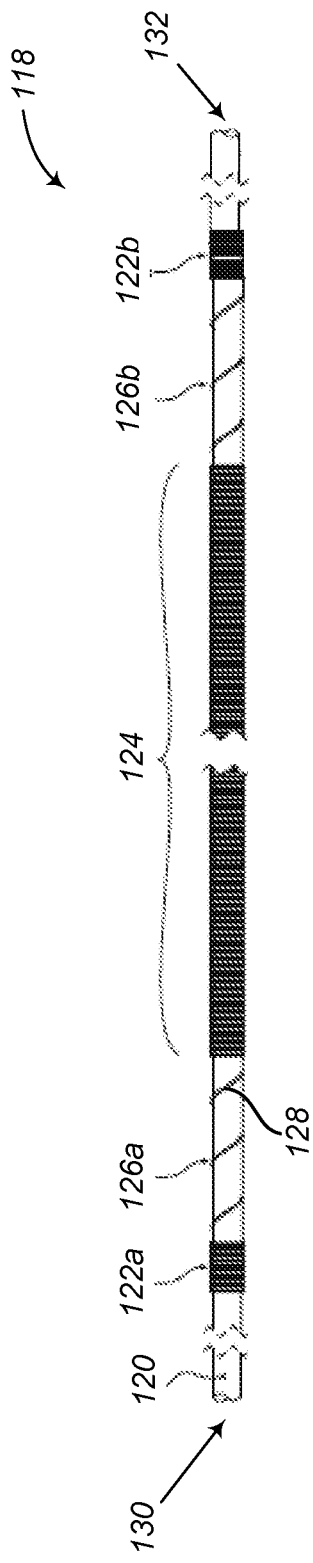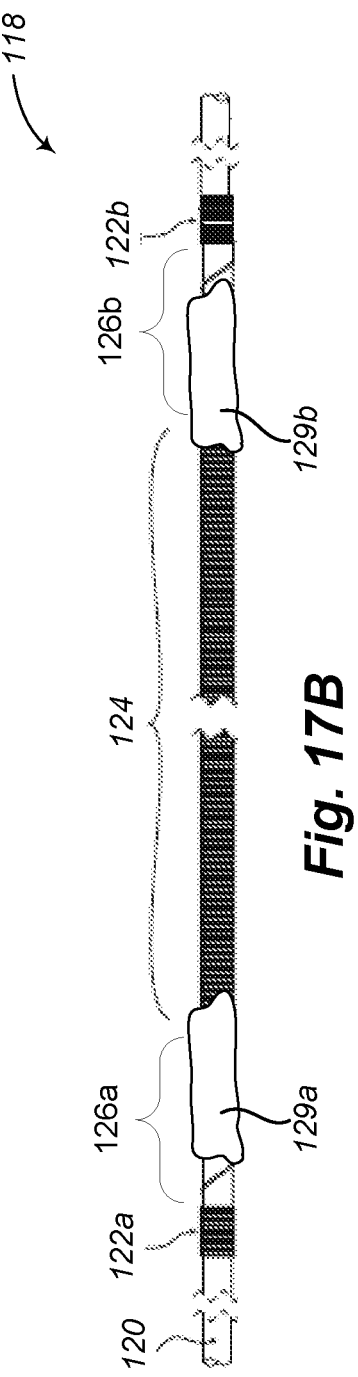
Fig. 17A
Fig. 17B

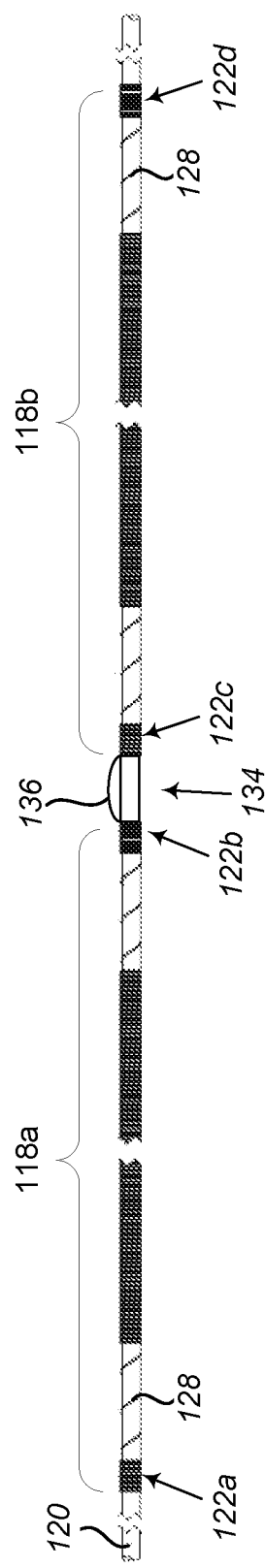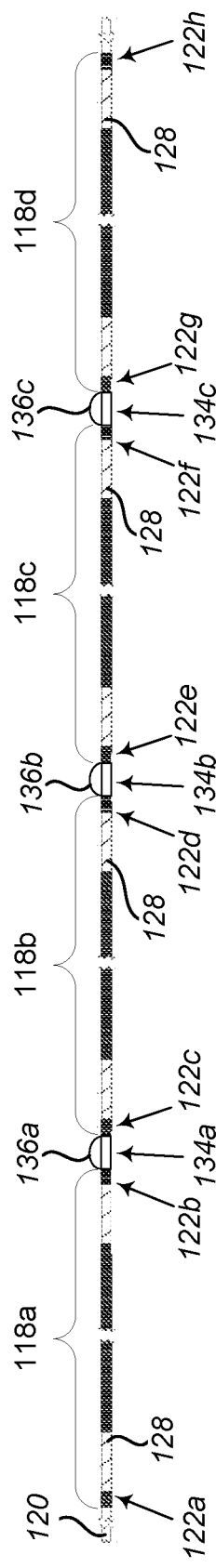
Fig. 21A
Fig. 21B

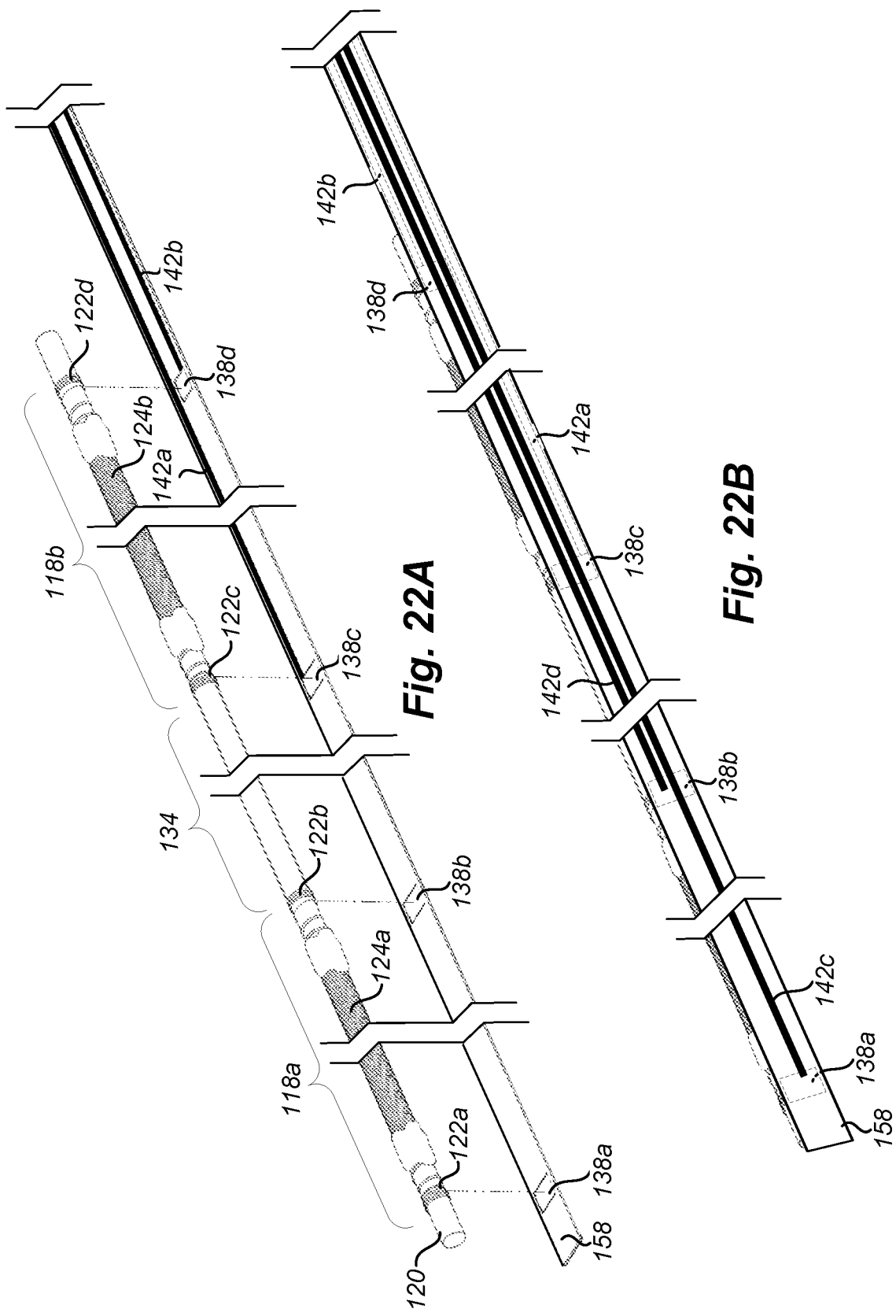

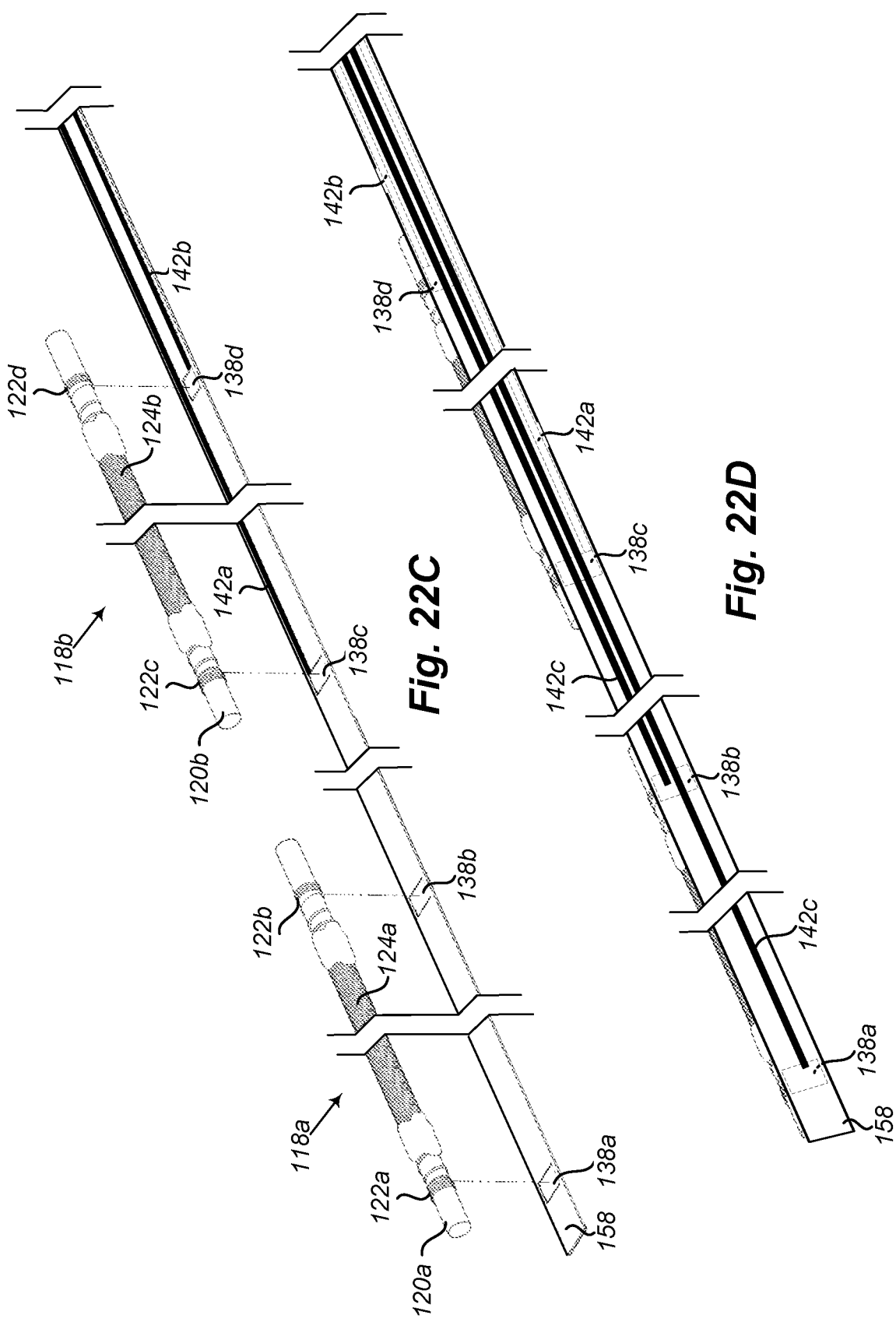

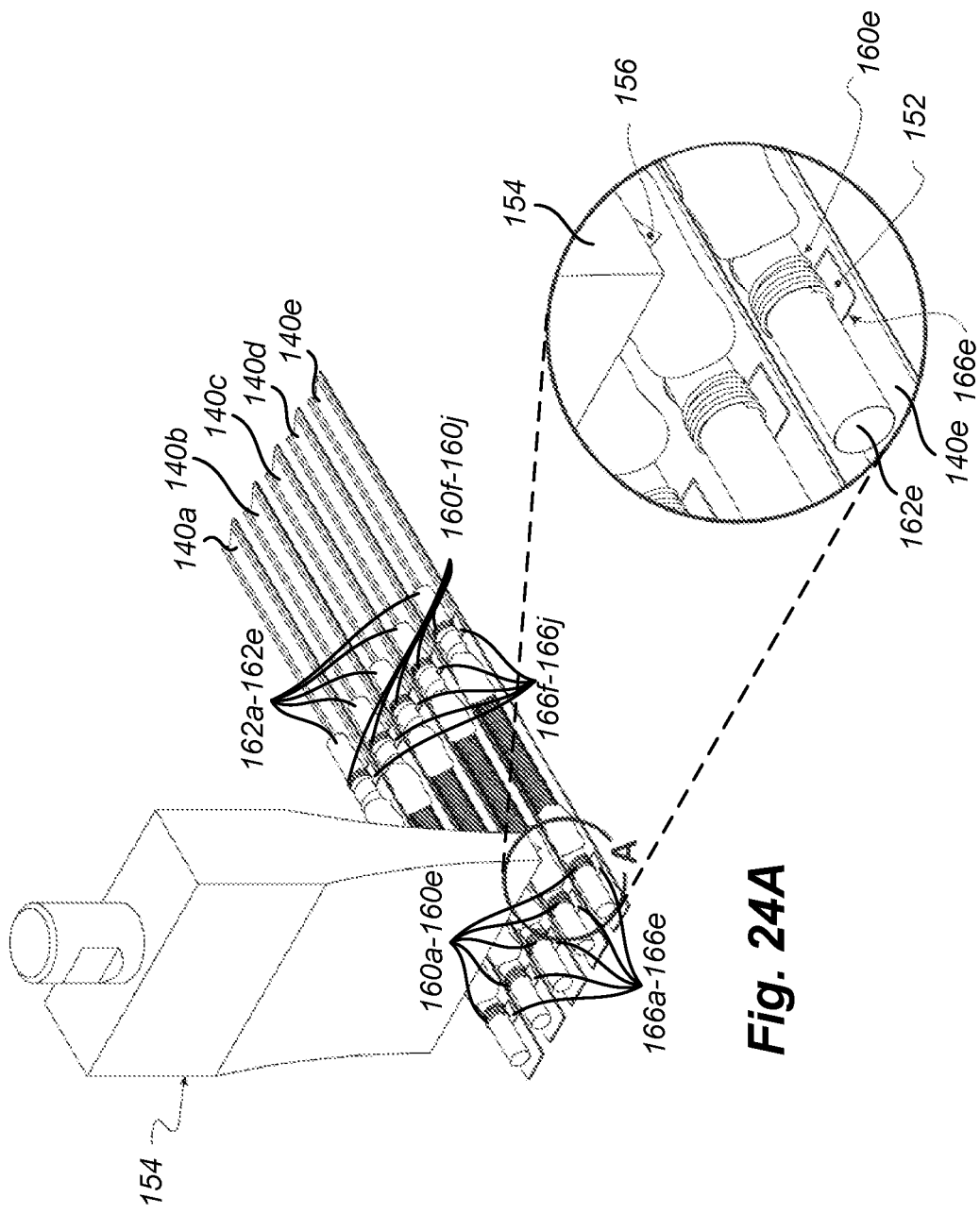

SECTION B-B

FLEXIBLE CIRCUIT BEARING A TRACKABLE LOW-FREQUENCY ELECTROMAGNETIC COIL

TECHNICAL FIELD

The present disclosure generally relates to tracking a medical instrument bearing an electromagnet structure within a body. More particularly, but not exclusively, the present disclosure relates to stimulating the electromagnet structure, which is formed at one end of a flexible circuit, with a low-frequency excitation signal, and tracking the electromagnet structure in real time when a portion of the medical instrument bearing the electromagnet structure is advanced within a body of a patient.

BACKGROUND

Description of the Related Art

In many medical procedures, a medical practitioner accesses an internal cavity of a patient using a medical instrument. In some cases, the medical practitioner accesses the internal cavity for diagnostic purposes. In other cases, the practitioner accesses the cavity to provide treatment. In still other cases, different therapy is provided.

Due to the sensitivity of internal tissues of a patient's body, incorrectly positioning the medical instrument within the body can cause great harm. Accordingly, it is beneficial to be able to precisely track the position of the medical instrument within the patient's body. However, accurately tracking the position of the medical instrument within the body can be quite difficult. The difficulties are amplified when the medical instrument is placed deep within the body of a large patient.

It is known that the medical instrument maybe tracked as it travels or remains stationary within the patient's body. For example, U.S. Pat. No. 5,425,382 to Golden et al. is entitled, APPARATUS AND METHOD FOR LOCATING A MEDICAL TUBE IN THE BODY OF A PATIENT. The patent describes an apparatus and method for locating a medical tube within the body of a patient. The medical tube is located by a detection apparatus, which senses the static magnetic field strength gradient generated by a magnet associated with the medical tube. The detection apparatus indicates the value of the field strength gradient to the medical practitioner. To use the device, the detection apparatus is moved about the body of the patient until the greatest gradient magnitude is indicated. The detection apparatus distinguishes the field strength of the magnet associated with the medical tube from the earth's field strength by sensing the magnet's field strength at two different distances from the magnet. U.S. Pat. No. 5,425,382 to Golden et al. is incorporated herein by reference to the fullest extent allowed by law.

Other examples are also provided. U.S. Pat. No. 5,622,169 to Golden et al. is entitled, APPARATUS AND METHOD FOR LOCATING A MEDICAL TUBE IN THE BODY OF A PATIENT. The patent describes a method of detecting the location of a magnet associated with a medical tube within the body of a patient. A first static magnetic field strength is sensed at a first distance from the magnet, and a second static magnetic field strength is sensed at a second distance from the magnet. The second distance is greater than the first distance. A first sensor signal is provided as a vector, which is a function of the first static magnetic field strength, and a second sensor signal is provided as a vector, which is a function of the second static magnetic field strength. The difference between the first static magnetic field strength and the second static magnetic field strength is provided as a differential signal vector value. The location of the medical tube can be determined by varying the first and second distances until the greatest value for the differential signal is indicated. U.S. Pat. No. 5,622,169 to Golden et al. is incorporated herein by reference to the fullest extent allowed by law.

U.S. Pat. No. 5,775,322 to Silverstein et al. is entitled, TRACHEAL TUBE AND METHODS RELATED THERETO. The patent describes a tracheal tube for insertion into the trachea of a patient. The tracheal tube includes a tube portion having a distal end, and a signal source such as a permanent magnet associated with the tube portion at a predefined distance from its distal end. The tracheal tube is inserted into the trachea of the patient such that the signal source is immediately posterior to the patient's cricothyroid ligament. Methods related to confirming proper placement of the tracheal tube by detecting the signal source immediately posterior to the patient's cricothyroid ligament are also disclosed. U.S. Pat. No. 5,775,322 to Silverstein et al. is incorporated herein by reference to the fullest extent allowed by law.

U.S. Pat. No. 5,879,297 to Haynor et al. is entitled, SYSTEM AND METHOD TO DETERMINE THE LOCATION AND ORIENTATION OF AN INDWELLING MEDICAL DEVICE. The patent describes a device to detect the location of a magnet coupled to an indwelling medical device within a patient. The device uses three or more sets of magnetic sensors each having sensor elements arranged in a known fashion. Each sensor element senses the magnetic field strength generated by the magnet, and each sensor element provides data indicative of the direction of the magnet in a three-dimensional space. The device uses fundamental equations for electricity and magnetism that relate measured magnetic field strength and magnetic field gradient to the location and strength of a magnetic dipole. The device uses an iterative process to determine the actual location and orientation of the magnet. An initial estimate of the location and orientation of the magnet results in the generation of predicted magnetic field values. The predicted magnetic field values are compared with the actual measured values provided by the magnetic sensors. Based on the difference between the predicted values and the measured values, the device estimates a new location of the magnet and calculates new predicted magnetic field strength values. This iteration process continues until the predicted values match the measured values within a desired degree of tolerance. At that point, the estimated location matches the actual location within a predetermined degree of tolerance. A two-dimensional display provides an indication of the location of the magnet with respect to the housing of the detector. A depth indicator portion of the display can be used to provide a relative or absolute indication of the depth of the magnet within the patient. U.S. Pat. No. 5,879,297 to Haynor et al. is incorporated herein by reference to the fullest extent allowed by law.

U.S. Pat. No. 5,902,238 to Golden et al. is entitled, MEDICAL TUBE AND APPARATUS FOR LOCATING THE SAME IN THE BODY OF A PATIENT. The patent describes a medical tube, an apparatus, and a method for locating the medical tube within the body of a patient. The medical tube has a permanent magnet associated therewith, which is capable of being located by a detection apparatus that senses the static magnetic field strength gradient generated by the permanent magnet. The detection apparatus indicates the value of the gradient to the user. In one embodiment, the magnet is associated with the distal end of the medical tube in a fixed orientation with a magnetic dipole pointing to the proximal end and parallel to a longitudinal axis of the medical tube. In this way, the polarity of the magnet's static magnetic field, as sensed by the detection apparatus, indicates the orientation of the distal end of the medical tube within the body of a patient. U.S. Pat. No. 5,902,238 to Golden et al. is incorporated herein by reference to the fullest extent allowed by law.

U.S. Pat. No. 6,129,668 to Haynor et al. is entitled, SYSTEM AND METHOD TO DETERMINE THE LOCATION AND ORIENTATION OF AN INDWELLING MEDICAL DEVICE. The patent describes a system to detect the position of a magnet associated with an indwelling medical device from a measurement location on the surface of a patient. The system includes a housing and first, second, and third magnetic sensors supported by the housing. Each of the magnetic sensors includes sensor elements to detect magnetic field strength in three orthogonal directions. The first, second, and third magnetic sensors generate first, second, and third sets of signals, respectively, as a function of static magnetic field strength and direction due to the magnet. A processor calculates an estimated position of the magnet in a three-dimensional space and calculates a predicted magnetic field strength for the first, second and third sensors based on the estimated position. The processor also calculates an actual magnetic field strength using the first, second, and third sets of signals and generates an error function based on a difference between the predicted magnetic field strength and the actual magnetic field strength. A display provides a visual display of data related to the position of the magnet in the three-dimensional space using the error function. U.S. Pat. No. 6,129,668 to Haynor et al. is incorporated herein by reference to the fullest extent allowed by law.

U.S. Pat. No. 6,173,715 to Sinanan et al. is entitled, MAGNETIC ANATOMICAL MARKER AND METHOD OF USE. The patent describes an anatomical marker that uses a permanent magnet to indicate a selected location within a patient. The magnet is enclosed within a non-degradable envelope and coupled to a retention member that is preferably manufactured from a biodegradable material, such as a polyglucuronic acid based material. The retention member may include one or more barbs to retain the anatomical marker in the selected location. An insertion tool, usable with an endoscope, can insert the anatomical marker. A retention magnet is fixedly attached to the insertion tool and holds the anatomical marker in place due to the attractive magnetic forces between the retention magnet and the marker magnet in the non-biodegradable envelope. When the anatomical marker is securely fastened at the selected location in the patient, the forces exerted by the patient's body on the retention member exceed the attractive magnetic forces between the retention magnet and the magnet in the envelope, thus causing the anatomical marker to be released from the insertion tool. The location of the magnet may be subsequently detected using a magnetic detector system. U.S. Pat. No. 6,173,715 to Sinanan et al. is incorporated herein by reference to the fullest extent allowed by law.

U.S. Pat. No. 6,216,028 to Haynor et al. is entitled, METHOD TO DETERMINE THE LOCATION AND ORIENTATION OF AN INDWELLING MEDICAL DEVICE. The patent describes a method to detect a position of a magnet associated with an indwelling medical device from a measurement location on the surface of a patient and in the presence of a magnetic field of the Earth. In the method, first, second, and third magnetic sensors having a known spatial relationship with respect to each other are positioned at the measurement location. At the first sensor positioned at a first distance from the magnet, a first set of electrical signals are generated as a function of a first magnetic field strength and direction due to the magnet; at the second sensor positioned at a second distance from the magnet, a second set of electrical signals are generated as a function of a second magnetic field strength and direction due to the magnet; and at the third sensor positioned at a third distance from the magnet, a third set of electrical signals are generated as a function of a third magnetic field strength and direction due to the magnet. An estimated position of the magnet in a three-dimensional space is calculated, and a predicted magnetic field strength for the first, second and third sensors based on the estimated position is also calculated. The effects of the Earth's magnetic field are canceled by subtracting a first selected one of the first, second, and third sets of electrical signals from a second selected one of the first, second, and third sets of electrical signals different from the first selected one of the first, second, and third sets of electrical signals to thereby generate a measured magnetic field strength using the first, second, and third sets of electrical signals. An error function is generated based on a difference between the predicted magnetic field strength and the measured magnetic field strength, and the three-dimensional position of the indwelling device is indicated by providing a visual display of the three-dimensional position of the associated magnet using the error function. U.S. Pat. No. 6,216,028 to Haynor et al. is incorporated herein by reference to the fullest extent allowed by law.

U.S. Pat. No. 6,263,230 to Haynor et al. is entitled, SYSTEM AND METHOD TO DETERMINE THE LOCATION AND ORIENTATION OF AN INDWELLING MEDICAL DEVICE. The patent describes a system to detect a position of a plurality of magnets within a patient from a measurement location outside the patient. The system includes a housing and a plurality of magnetic sensors supported by the housing. Each of the plurality of sensors is oriented in a known direction and generates a set of signals as a function of static magnetic field strength and direction due to the plurality of magnets within the patient. A processor calculates an estimated position of each of the plurality of magnets in a three-dimensional space and calculates values of a predicted magnetic field strength for at least a portion of the plurality of sensors based on the estimated positions of each of the plurality of magnets. The processor also calculates values of an actual magnetic field strength using the set of signals and determines values of the location of each of the plurality of magnets based on the difference between the values of the predicted magnetic field strength and the values of the actual magnetic field strength. A display provides a visual display of the position of each of the plurality of magnets in the three-dimensional space. U.S. Pat. No. 6,263,230 to Haynor et al. is incorporated herein by reference to the fullest extent allowed by law.

U.S. Pat. No. 6,292,680 to Somogyi et al. is entitled, NON-INVASIVE SENSING OF A PHYSICAL PARAMETER. The patent describes a method and device for non-invasively sensing a physical parameter within the body of a patient by employing a magnetically-based sensing device and a monitoring device. The magnetically-based sensing device has a first magnet and a second magnet, which generate a combined magnet field. The first and second magnets are positioned such that a change in a physical parameter causes a change in the combined magnet field, and the change is monitored by the monitoring device. U.S. Pat. No. 6,292,680 to Somogyi et al. is incorporated herein by reference to the fullest extent allowed by law.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

BRIEF SUMMARY

A system may be summarized as including: a medical instrument having a first portion and a second portion with the first portion configured for insertion into a body of a patient, the medical instrument including: a flexible printed circuit having a length and a width, wherein the length is at least twenty times the width, the flexible printed circuit including: a first metal trace running substantially along the length of the flexible printed circuit, the first metal trace having a first end in the first portion of the medical instrument and a second end in the second portion of the medical instrument; and a second metal trace running substantially along the length of the flexible printed circuit, the second metal trace having a first end in the first portion of the medical instrument and a second end in the second portion of the medical instrument; an electromagnet structure in the first portion of the medical instrument, the electromagnet structure including: a core; and a conductive coil wound around the core with a first end of the conductive coil electrically coupled to the first end of the first metal trace and a second end of the conductive coil electrically coupled to the first end of the second metal trace; and ancillary circuitry arranged in the second portion of the medical instrument and electrically coupled to the second end of the first metal trace and to the second end of the second metal trace, the ancillary circuitry configured to drive an excitation signal through the conductive coil via the first and second metal traces to generate a magnetic field about the electromagnet structure.

The system may further include: a sensor configured to sense the magnetic field created when the excitation signal is driven through the conductive coil and further configured to output a sensor signal representative of at least one portion of the sensed magnetic field; and a control circuit configured to calculate a position corresponding to the first portion of the medical instrument within the body of the patient based on the sensor signal. The first portion of the medical instrument may further include: a containment structure that contains the electromagnet structure and a first portion of the flexible printed circuit. The containment structure may be arranged as a multi-lumen catheter having at least two cavities that extend along a length of the multi-lumen catheter, wherein the electromagnet structure and the first portion of the flexible printed circuit are positioned in one of the two cavities of the multi-lumen catheter. The medical instrument may further include: a stiffness member that extends linearly along the length of the flexible printed circuit. The stiffness member may extend linearly along only a portion of the length of the flexible printed circuit. The stiffness member may be arranged as an electrode that is electrically coupled to additional ancillary circuitry, the additional ancillary circuitry and the electrode may be arranged to capture one or more electrical measurements within the body of the patient. The medical instrument may further include: a multi-lumen catheter that contains the first portion of the medical instrument in a first lumen, the first lumen extending along a length of the multi-lumen catheter. The medical instrument may further include: a stiffness member coupled to the flexible printed circuit; and a tube-like structure that contains the electromagnet structure, a first portion of the flexible printed circuit, and at least a portion of the stiffness member. The core may have a length that extends linearly along the length of the flexible printed circuit, wherein the conductive coil may be wound around a first portion of the length of the core, and wherein a second portion of the length of the core may be affixed to the flexible printed circuit. The medical instrument may further include: third and fourth metal traces running along the length of the flexible printed circuit wherein the third and fourth metal traces each have a first end in the first portion of the medical instrument and a second end in the second portion of the medical instrument; a second electromagnet structure in the first portion of the medical instrument, the second electromagnet structure including: a second core; and a second conductive coil wound around the second core with a first end of the second conductive coil electrically coupled to the first end of the third metal trace and a second end of the second conductive coil electrically coupled to the first end of the fourth metal trace; and second ancillary circuitry arranged in the second portion of the medical instrument and electrically coupled to the second end of the third metal trace and to the second end of the fourth metal trace, the second ancillary circuitry configured to drive a second excitation signal through the second conductive coil via the third and fourth metal traces. The core and the second core may share a single core structure. The flexible printed circuit may further include: a substantially flat first surface and a substantially flat opposing second surface that both run along the length of the flexible printed circuit; wherein the first and second metal traces run along the length of the flexible printed circuit on the first surface; and an electrode pattern runs along the length of the flexible printed circuit on the second surface. The flexible printed circuit may further include: a plurality of layers, wherein the first and second metal traces run substantially along the length of the flexible printed circuit on a first layer of the plurality of layers; a first electrode pattern runs substantially along the length of the flexible printed circuit on a second layer of the plurality of layers; and a second electrode pattern runs substantially along the length of the flexible printed circuit on a third layer of the plurality of layers. The second portion of the medical instrument may further include: a housing that contains the ancillary circuitry. The housing may contain at least one battery arranged to supply power to the ancillary circuitry to drive the excitation signal to the conductive coil.

A method to make a medical device may be summarized as including: creating an electromagnet structure by winding a wire-like conductor into a coil around a core, the wire-like conductor having two opposing ends, wherein a first of the two opposing ends is arranged as a first lead of the coil and a second of the two opposing ends is arranged as a second lead of the coil; providing a flexible printed circuit structure having patterned therein a first metal trace and a second metal trace running linearly along a substantial length of a flexible substrate to form the flexible printed circuit structure, each of the first and second metal traces having a first end and a second end; electrically connecting the first lead of the coil to the first end of the first metal trace; electrically connecting the second lead of the coil to the first end of the second metal trace; and electrically connecting ancillary circuitry to the second end of the first metal trace and to the second end of the second metal trace, the ancillary circuitry positioned on the flexible printed circuit structure at an opposite end from the electromagnet structure.

The method may further include: creating a second electromagnet structure by winding a second wire-like conductor into a second coil around a second core, the second wire-like conductor having two opposing ends, wherein a first of the two opposing ends is arranged as a first lead of the second coil and a second of the two opposing ends is arranged as a second lead of the second coil; providing the flexible printed circuit structure having patterned therein a third metal trace and a fourth metal trace running linearly along the substantial length of the flexible printed circuit structure, each of the third and fourth metal traces having a first end and a second end; electrically connecting the first lead of the second coil to the first end of the third metal trace; electrically connecting the second lead of the second coil to the first end of the fourth metal trace; and electrically connecting the ancillary circuitry to the second end of the third metal trace and to the second end of the fourth metal trace. The method of may further include: containing at least a first portion of the flexible printed circuit structure and the electromagnet structure within a tube-like structure. The method may further include: containing at least a first portion of the flexible printed circuit structure and the electromagnet structure within a cavity of a multi-lumen catheter. The method may further include integrating an electrode in the medical device substantially along the substantial length of the flexible printed circuit structure.

A method of operating a medical device may be summarized as including: passing a first portion of the medical device into a body of a patient while a second portion of the medical device remains outside the body of the patient; operating ancillary circuitry arranged at the second portion of the medical device to drive an excitation signal through a conductive coil of an electromagnet structure arranged at the first portion of the medical device, the excitation signal passed via first and second traces running substantially along a length of a flexible printed circuit, wherein the electromagnet structure includes a core and the conductive coil wound around the core, and wherein a first end of the conductive coil is electrically connected to a first end of the first trace and a second end of the conductive coil is electrically connected to a first end of the second trace; and sensing a magnetic field generated about the electromagnet structure by the excitation signal being driven through the conductive coil.

The method may further include; based at least in part on the sensed magnetic field, generating a representation of the first portion of the medical device in the body of the patient; and outputting the representation of the first portion of the medical device in the body of the patient to a presentation system. The method may further include; advancing the first portion of the medical device further into the body of the patient; and tracking the first portion of the medical device as it advances into the body of the patient.

A method to make a plurality of medical devices may be summarized as including: forming a plurality of electromagnet structures by winding a wire-like conductor into a respective coil around each respective core of a plurality of cores, the wire-like conductor of each respective coil having two opposing ends, wherein a first of the two opposing ends is arranged as a first lead of the respective coil and a second of the two opposing ends is arranged as a second lead of the respective coil; arranging the plurality of electromagnet structures on an assembly tray; forming an assembly panel of a plurality of flexible printed circuit structures, each respective flexible printed circuit structure of the plurality of flexible printed circuit structures having patterned therein a first metal trace and a second metal trace running linearly along a substantial length of a flexible substrate to form the respective flexible printed circuit structure, each of the first and second metal traces having a first end and a second end; for each corresponding pair of electromagnet structures of the plurality of electromagnet structures on the assembly tray and flexible printed circuit structure of the plurality of flexible printed circuit structures in the assembly panel: removing an electromagnet structure from the assembly tray and aligning the electromagnet structure with a corresponding flexible printed circuit structure with the first lead of the coil of the electromagnet structure positioned with the first end of the first metal trace of the corresponding flexible printed circuit structure and the second lead of the coil of the electromagnet structure positioned with the first end of the second metal trace of the corresponding flexible printed circuit structure; electrically connecting the first lead of the coil of the electromagnet structure to the first end of the first metal trace of the corresponding flexible printed circuit structure; electrically connecting the second lead of the coil of the electromagnet structure to the first end of the second metal trace of the corresponding flexible printed circuit structure; positioning corresponding ancillary circuitry on the corresponding flexible printed circuit structure at an opposite end from the electromagnet structure; and electrically connecting the corresponding ancillary circuitry to the second end of the first metal trace of the corresponding flexible printed circuit structure and to the second end of the second metal trace of the corresponding flexible printed circuit structure.

The arranging of the plurality of electromagnet structures on the assembly tray may include: positioning an orientation of each of the plurality of electromagnet structures substantially similar to one another. The forming of the assembly panel of plurality of flexible printed circuit structures may include: forming each of the plurality of flexible printed circuit structures in the assembly panel with a substantially similar orientation.

A system may be summarized as including: a medical instrument having a first portion and a second portion with the first portion configured for insertion into a body of a patient, the medical instrument including: a flexible printed circuit having a length, the flexible printed circuit including: a first metal trace running substantially along the length of the flexible printed circuit, the first metal trace having a first end in the first portion of the medical instrument and a second end in the second portion of the medical instrument; a first contact pad electrically coupled to the first end of the first metal trace; a second metal trace running substantially along the length of the flexible printed circuit, the second metal trace having a first end in the first portion of the medical instrument and a second end in the second portion of the medical instrument; and a second contact pad electrically coupled to the first end of the second metal trace; an electromagnet structure in the first portion of the medical instrument, the electromagnet structure including: a core; a first lead contact electrically coupled to the first contact pad; a second lead contact electrically coupled to the second contact pad; and a conductive coil wound around the core with a first end of the conductive coil electrically coupled to the first lead contact and a second end of the conductive coil electrically coupled to the second lead contact; and ancillary circuitry arranged in the second portion of the medical instrument and electrically coupled to the second end of the first metal trace and to the second end of the second metal trace, the ancillary circuitry configured to drive an excitation signal through the conductive coil via the first and second metal traces to generate a magnetic field about the electromagnet structure.

The first lead contact, the second lead contact, and the conductive coil may be configured from a wire wound around the core with the conductive coil disposed between the first and second lead contacts. The wire wound around the core for the first lead contact may have a first pitch, the wire wound around the core for the second lead contact may have a second pitch, and the wire wound around the core for the conductive coil may have a third pitch. The electromagnet structure may further include: a first gap section between the first lead contact and the conductive coil; and a second gap section between the second lead contact and the conductive coil. The electromagnet structure may further include: a wire wound around the core to form the first and second lead contacts, the first and second gap sections and the conductive coil, wherein the wound wire for the first and second lead contacts and the conductive coil have a first pitch, and wherein the wound wire for the first and second gap sections have a second pitch that is higher than the first pitch.

A method to make a medical device may be summarized as including: forming an electromagnet structure by winding a wire-like conductor around a core to form a first lead contact, a second lead contact, a conductive coil disposed between the first lead contact and the second lead contact, a first gap section disposed between the first lead contact and the conductive coil, and a second gap section disposed between the conductive coil and the second lead contact; forming a flexible printed circuit structure having a flexible substrate and patterned therein a first metal trace, a second metal trace, a first contact pad, and a second contact pad, the first and second metal traces having a first end and a second end and running linearly along a length of the flexible substrate, the first end of the first metal trace being electrically coupled to the first contact pad, and the first end of the second metal trace being electrically coupled to the second contact pad; aligning the electromagnet structure with the flexible printed circuit structure, the aligning including aligning first lead contact of the electromagnet structure with the first contact pad of the flexible printed circuit structure and aligning the second lead contact of the electromagnet structure with the second contact pad of the flexible printed circuit structure; electrically connecting the first lead contact of the electromagnet structure to the first contact pad of the flexible printed circuit structure; electrically connecting the second lead contact of the electromagnet structure to the second contact pad of the flexible printed circuit structure; positioning ancillary circuitry on the flexible printed circuit structure at an opposite end from the electromagnet structure; and electrically connecting the ancillary circuitry to the second end of the first metal trace of the flexible printed circuit structure and to the second end of the second metal trace of the flexible printed circuit structure.

Forming the electromagnet structure may include: winding the wire-like conductor around the core at a first pitch to form the first lead contact; winding the wire-like conductor around the core at a second pitch to form the first gap section, the second pitch being higher than the first pitch; winding the wire-like conductor around the core at a third pitch to form the conductive coil, the third pitch being lower than the second pitch; winding the wire-like conductor around the core at a fourth pitch to form the second gap section, the fourth pitch being higher than the third pitch; and winding the wire-like conductor around the core at a fifth pitch to form the second lead contact, the fifth pitch being lower than the fourth pitch.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. The shapes of various elements and angles are not necessarily drawn to scale either, and some of these elements are enlarged and positioned to improve drawing legibility. One or more embodiments are described hereinafter with reference to the accompanying drawings in which:

FIGS. 2A-2C are illustrations of a flexible printed circuit with an electromagnet structure as part of a medical instrument, according to one embodiment;

FIGS. 7A-7C are illustrations of a flexible printed circuit with an electromagnet structure and a wire electrode within a tri-lumen catheter of a medical instrument, according to one embodiment;

FIGS. 10A-10B are illustrations of a flexible printed circuit with an electromagnet structure and a housing with ancillary circuitry and cables, according to one embodiment;

FIGS. 11A-11D are illustrations of a flexible printed circuit with an electromagnet structure assembly with batteries, according to one embodiment;

FIGS. 12-13 are illustrations of various flexible printed circuits with an electromagnet structure and multiple electrode patterns, according to various embodiments;

FIGS. 17A-17B are illustrations of an electromagnet structure as part of a medical instrument, according to one embodiment;

FIGS. 21A-21B are illustrations of alternative multiple electromagnet structures manufactured on a single core, according to one embodiment;

FIGS. 22A-22D are illustrations of a flexible printed circuit with multiple electromagnet structures as part of a medical instrument, according to one embodiment;

FIGS. 24A-24D are illustrations of assembly of a plurality of flexible printed circuits with electromagnet structure assemblies, according to one embodiment.

DETAILED DESCRIPTION

Figure 1:
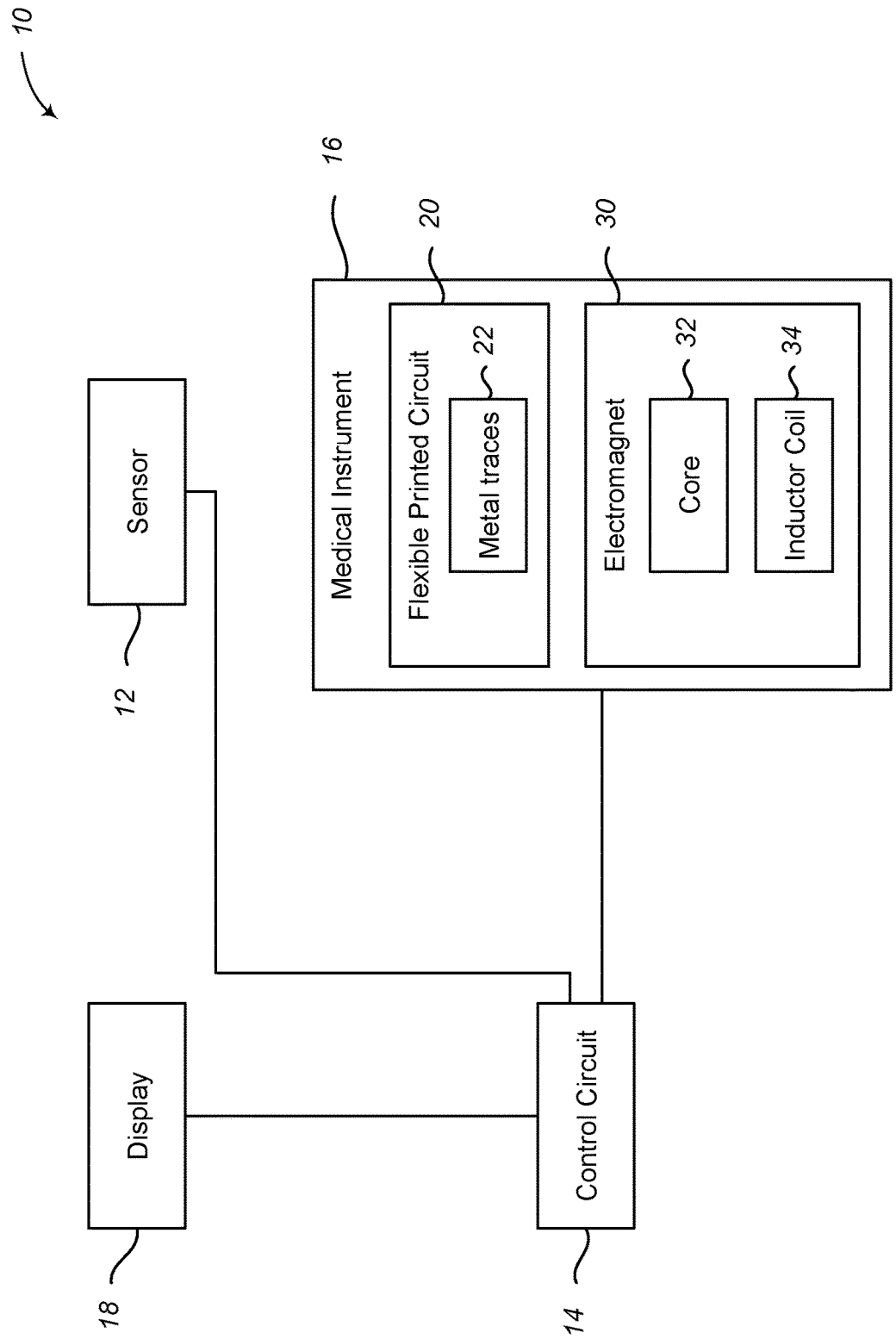
FIG. 1 is a block diagram of a system for detecting the position of a medical instrument within a body of a patient, according to one embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. Also in these instances, well-known structures may be omitted or shown and described in reduced detail to avoid unnecessarily obscuring descriptions of the embodiments.

Prior to setting forth the embodiments, however, it may be helpful to an understanding thereof to first set forth definitions of certain terms that are used hereinafter.

"Medical instrument" refers to a device, instrument, apparatus, constructed element or composition, machine, implement, or similar or related article that can be utilized to diagnose, prevent, treat or manage a disease or other condition(s). For example, medical instruments are used on patients in surgery, preventive care, diagnosis of disease or other condition, treatment, and a wide range of other physiological processes. A medical instrument is a device used in a procedure on the body of a subject (e.g., a patient). Medical instruments include needles, probes, stylets, catheters (e.g., a Peripherally Inserted Central Catheter (PICC)), cannulas, medical tubes, tracheal tubes, rigid tubes, and other such apparatus. Some medical instruments have passages to pass light, fluid, or other therapies. Other medical instruments are solid and pass electricity or mechanical force (e.g., a probe used by a medical practitioner to move or sample a biological mass). Accordingly, in some cases, the medical instrument is a hollow tube-like device. In some cases, the medical instrument is an elongated solid member. In some cases, the medical instrument takes another form.

The medical instrument may be placed through the mouth of the subject or through another of the subject's orifices. Alternatively, the medical instrument may be placed through a surgical incision made by a medical practitioner at some location on the body of the subject. The medical instrument may be placed and moved in other ways. The placement of the medical instrument or a device placed by the medical instrument may be permanent, semi-permanent, or temporary.

The medical instruments provided herein may, depending on the device and the embodiment, be implanted within a subject, utilized to deliver a device to a subject, or utilized externally on a subject. In many embodiments the medical instruments provided herein are sterile and subject to regulatory requirements relating to their sale and use. Representative examples of medical instruments are used in cardiovascular procedures to implant, for example, cardiovascular devices, implantable cardioverter defibrillators, pacemakers, stents, stent grafts, bypass grafts, catheters and heart valves; they are used in orthopedic procedures to implant, for example, hip and knee prostheses, and spinal implants and hardware (spinal cages, screws, plates, pins, rods and artificial discs); and they are used in a wide variety of procedures that place medical tubes, cosmetic and/or aesthetic implants (e.g., breast implants, fillers). Other representative examples of medical instruments are used to deliver a wide variety of polymers, bone cements, bone fillers, scaffolds, and naturally occurring materials (e.g., heart valves, and grafts from other naturally occurring sources); intrauterine devices; orthopedic hardware (e.g., casts, braces, tensor bandages, external fixation devices, tensors, slings and supports) and internal hardware (e.g., K-wires, pins, screws, plates, and intramedullary devices (e.g., rods and nails)); cochlear implants; dental implants; medical polymers; a wide variety of neurological devices; and artificial intraocular eye lenses. Other uses are also contemplated.

An "electromagnet structure" or "electromagnetic structure" is a structure that includes one or more electromagnets. In cases where two or more electromagnet structures are formed, some or all of the electromagnet structures may be arranged in a determined orientation relative to one or more other electromagnet structures. Each electromagnet structure is created having a wire-like conductor wound into a coil, and a core structure centrally located within the center of the coil. In some cases, two or more electromagnet structures may share a core structure. For example, a first electromagnet structure may be formed by winding a copper-based wire around a ferrous rod core structure at a first location of the ferrous rod core structure. In some cases, a second coil of copper-based wire is wound around the ferrous rod core structure at a second location of the ferrous rod core structure different from the first location of the ferrous rod core structure.

The "wire-like conductor" of a coil in an electromagnet structure may be a wire, a trace manufactured with any type of electronic process (e.g., a semiconductor process, a printed circuit process, and the like), or some other such structure. The wire-like conductor may have a cross-reference shape that is circumferential, substantially circular, substantially square, octagonal, hexagonal, or having some other cross-section. The wire-like conductor may be arranged in a coil structure by winding the wire-like conductor around the core structure. Alternatively, the wire-like conductor may be arranged in a coil by another process, and the core structure may be later placed centrally in the inner void of the coil. The wire-like conductor may be formed from copper, a copper alloy, gold, tin, or some other electrically conductive material.

"Contain" in all of its forms refers to one structure being integrated or otherwise located inside another structure.

Contain includes encase, enclose, encapsulate, surround, envelop, confine, and other like terms. When a first structure contains a second structure, the containment may be total or partial. For example, a housing may contain an electronic circuit. The housing may have holes, slots, open sides, or other features the allow the some or all of the electronic circuit to be seen without opening or otherwise manipulating the housing. As another example, an insulating jacket may contain a wire, a lumen may contain an electromagnet structure, and a conductive coil may contain a ferrous-based core structure.

"Substantial" may refer to a portion of a dimension that is greater than or equal to 50 percent (>=50%). For example, where a conductive trace extends substantially along the length of a flexible circuit, the conductive trace is at least one half of the length of the flexible circuit.

In many medical situations, it is desirable to penetrate the solid or semi-solid biological matter of a patient's body, and guide a medical instrument to a precise location. For example, one common medical practice involves diagnosis and therapy of a tumor in a patient's body. Another common medical practice involves accurately placing a flexible catheter in a patient's body. When a portion of the medical instrument (e.g., the flexible catheter) that will penetrate and pass into the patient's body has at least one electromagnet structure, and when the electromagnet structure is driven with a low-frequency excitation signal, then the electromagnet structure will be trackable to a precise location within the body of the patient.

A magnetic field sensing device (e.g., a sensor) is operated by a medical practitioner proximal to the body of the patient. In some cases, the medical practitioner places the magnetic field sensing device directly in contact with the body of the patient. Generally, the medical practitioner will attempt to place the magnetic field sensing device adjacent to the portion of the patient's body where the electromagnet structure is believed to be.

A presentation system includes one or more of a video display, an audio input/output system, a tactile feedback system, or some other presentation mechanism. The presentation system may further include one or more user input interfaces for keyboards, mice, touch screens, buttons, dials, and other like controls. The presentation system provides input information to the magnetic field sensing device and receives output information from the magnetic field sensing device.

Embodiments of the presentation system are used to present information representing the position and orientation of the medical instrument by receiving and processing magnetic field information. Magnetic field information is generated when the low-frequency excitation signal is applied to the electromagnet structure. The electromagnet structure is tracked as the medical instrument (e.g., flexible catheter) is advanced through the body of the patient. The medical instrument does not need to follow a straight line or any specific pattern in order to be tracked.

The present invention may be understood more readily by reference to the following detailed description of the preferred embodiments of the invention. It is to be understood that the terminology used herein is for the purpose of describing specific embodiments only and is not intended to be limiting. It is further to be understood that unless specifically defined herein, the terminology used herein is to be given its traditional meaning as known in the relevant art.

FIG. 1 is a block diagram of a system 10 for detecting the position of a medical instrument 16 within the body of a patient, according to one embodiment. The system 10 includes a medical instrument 16, a sensor 12, a presentation system 18, and a control circuit 14. The control circuit 14 is coupled to the medical instrument 16, the sensor 12, and the presentation system 18. The medical instrument 16 includes a flexible printed circuit 20, also referred to as a flexible circuit, and an electromagnet structure 30. The electromagnet structure 30 includes a conductive coil 34 wound about a core 32 (e.g., a ferrous-based core structure). The flexible printed circuit 20 includes a plurality of metal traces 22 (e.g., two metal traces). The metal traces 22 are electrically coupled to the lead ends of the conductive coil 34 so that electrical current passes through the conductive coil 34.

In one embodiment, the medical instrument 16 is a medical device configured to be introduced, either partially or wholly, into the body of a patient in conjunction with a medical procedure. The patient may be a human patient or a non-human patient.

In many cases, the electromagnet structure 30 and the flexible printed circuit 20 are integrated with the medical instrument 16. For example, when the medical instrument 16 includes or is a stylet, the electromagnet structure 30 and at least a portion of the flexible printed circuit 20 may be formed as part of the stylet.

In many medical procedures, it can be very advantageous to accurately track the position of the medical instrument 16 within the body of the patient. For example, if the medical instrument 16 is delivering fluid to a particular part of the patient's body, then it can be very advantageous to accurately track the position of medical instrument 16 to provide confidence that the medical instrument is in the correct position for fluid delivery. In some particularly sensitive medical procedures, knowing the exact position of the medical instrument 16 with substantial certainty can improve the well-being of the patient during a medical procedure.

The electromagnet structure 30 enables tracking of the position of the medical instrument 16. When a current is passed through the conductive coil 34, a detectable and trackable magnetic field is generated. Depending at least in part on the material of the core 32, the core 32 can supplement or strengthen the magnetic field. The magnetic field can enable detection and tracking of the medical instrument 16.

The sensor 12 includes one or more magnetic sensors that sense a magnetic field created when an excitation signal is driven through the conductive coil 34. The sensor 12 generates data representative of the magnetic field generated by the conductive coil 34 and the core 32. The sensor 12 can detect parameters of the magnetic field such as field strength and direction. The sensor 12 generates one or more sensor signals indicative of parameters of the magnetic field. The position of the medical instrument 16, along with orientation, motion, and other location-based information, can be determined based on the parameters of the magnetic field generated by the conductive coil 34 and the core 32. Operations of the sensor 12 are in some cases coordinated by the control circuit 14 such that parameters to direct the sensor functions are applied in cooperation with parameters to direct excitation of the electromagnet structure 30.

In one embodiment, the control circuit 14 both drives the current through the conductive coil 34 and calculates location-based information (e.g., position, orientation, motion, and the like) of the medical instrument 16. The control circuit 14 receives the one or more sensor signals from the sensor 12 and analyzes the one or more sensor signals. The control circuit 14 generates the location-based information, such as the position of the medical instrument 16, based on the one or more sensor signals.

In some embodiments, the control circuit 14 may be separate from the medical instrument 16. In other embodiments, the control circuit 14 may be integrated into the medical instrument 16.

In one embodiment the control circuit 14 executes particular algorithms to identify and track the position of the medical instrument 16 in three dimensions and the orientation of medical instrument 16 relative to a reference point, based on the position of the electromagnet structure 30. In these and other cases, tracking the position of the medical instrument 16 includes integrating current and historical position data in order to predict one or more future positions of the medical instrument 16.

It can be difficult to accurately track the position of the medical instrument 16 within the body of the patient as the medical instrument 16 is positioned deeper within the body of the patient. In larger patients, the problem can be exacerbated because the medical instrument 16 may need to travel deeper below the skin of the patient in order to reach particular areas of the body in accordance with various medical procedures. It can be difficult to generate a magnetic field with sufficient strength and stability to allow reliable tracking of the medical instrument 16. This problem can be compounded by the fact that in many circumstances it is more desirable to have a conductive coil 34 and a core 32 that are relatively small, in order to reduce disruption of body tissues as the medical instrument 16 is introduced into the body of the patient. As the dimensions of the conductive coil 34 are reduced, it can be difficult to generate sufficiently strong and acceptably stable magnetic fields to enable detection. Furthermore, interference from the Earth's magnetic field, from other medical and non-medical equipment that may be positioned in or near the patient's body, and from the medical instrument 16 itself can make it difficult to accurately calculate the position of the medical instrument 16 within the body of the patient.

In one embodiment, in order to enable more accurate tracking of the medical instrument 16 deep within the body of a patient, the control circuit 14 drives the conductive coil 34 with a low frequency excitation signal instead of a DC signal or a high-frequency excitation signal. The low-frequency excitation signal causes a current to be passed through the metal traces 22 and through the conductive coil 34. As the direction and magnitude of the current change, the parameters of the magnetic field generated by the conductive coil 34 also change. The magnetic field generated by the electromagnet structure 30 has particular characteristics based in part on the waveform of the excitation signal. These particular oscillating characteristics can enable the sensor 12 to distinguish the magnetic field from noise, interference, and/or other magnetic fields. In this way, the sensor 12 can track the position of the medical instrument 16 with acceptable accuracy, even when the medical instrument 16 is deep within the body of the patient.

In one embodiment, the control circuit 14 drives the conductive coil 34 with an excitation signal having a frequency less than 10,000 Hz. In one embodiment, the control circuit 14 can drive the conductive coil 34 with an excitation signal having a frequency less than 500 Hz. In one embodiment, the control circuit 14 drives the conductive coil 34 with an excitation signal having a frequency of about 330 Hz. The selection of a 330-Hz excitation signal helps to avoid AC line related components, which might occur at a multiple of a line frequency. For example, 300 Hz, which is a multiple of both 50 Hz and 60 Hz—two common line frequencies in Europe and the U.S., respectively—may provide strong magnetic returns, but the strong magnetic returns may also have measurable harmonic components associated with the AC line frequency.

The control circuit 14 has been described as driving the conductive coil 34 with an excitation signal or by applying an excitation signal to the conductive coil 34. The control circuit 14 can accomplish this by directly applying the excitation signal to the conductive coil 34 via the metal traces 22 on the flexible printed circuit 20. Alternatively, the control circuit 14 can accomplish this indirectly by controlling a voltage source to apply a voltage to the conductive coil 34 or by controlling a current source to supply a current to the conductive coil 34 via the metal traces 22. Those of skill in the art will recognize, in light of the present disclosure, that the control circuit 14 can apply an excitation signal to the conductive coil 34 in many other ways. All such other ways fall within the scope of the present disclosure.

In one embodiment, the presentation system 18 displays a visual representation of the position of the medical instrument 16 within the body of the patient. The visual representation of the position of the medical instrument 16 enables medical personnel to accurately know the position of the medical instrument 16 within the body of the patient. This in turn can enable the medical personnel to correctly perform medical procedures on the patient.

In one embodiment, the control circuit 14 generates a video signal, and outputs the video signal to the presentation system 18. The video signal includes a representation of the position of the medical instrument 16 within the body of the patient. The video signal can also include position data that can be displayed on the presentation system 18. The position data can include text that indicates numerical coordinates representing the position, orientation, and motion of the medical instrument 16. The presentation system 18 can display both the visual representation of the position of the medical instrument 16 within the body of the patient and the position data indicating the position of the medical instrument 16 within the body of the patient.

The control circuit 14 may include multiple discrete control circuit portions. The control circuit 14 can include one or more microcontrollers, one or more microprocessors, one or more memory devices, one or more voltage sources, one or more current sources, one or more analog-to-digital converters, one or more digital-to-analog converters, and/or one or more wireless transceivers. One or more of these components can collectively make up the control circuit 14.

Figure 2A:
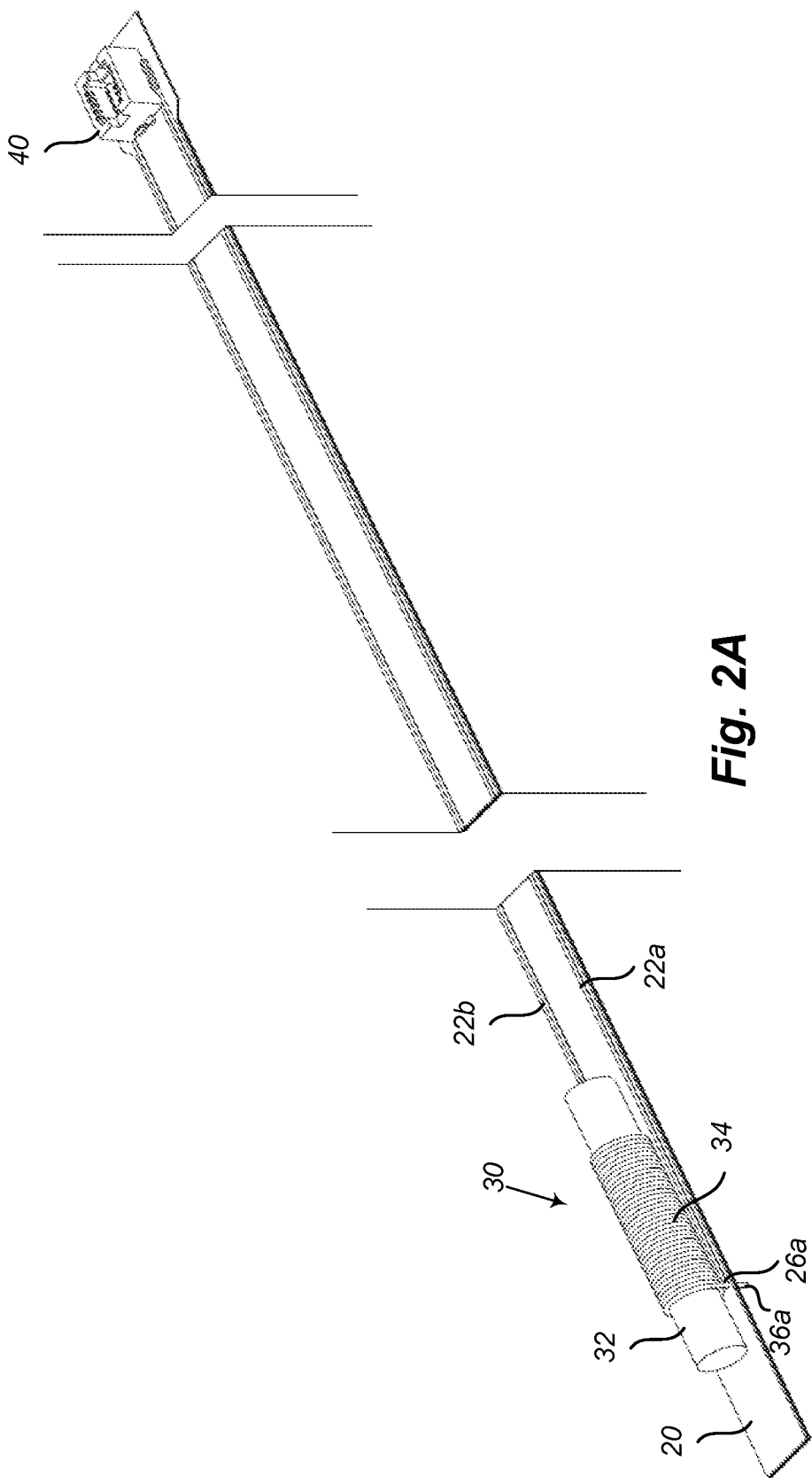

FIGS. 2A-2C are illustrations of a flexible printed circuit 20 with an electromagnet structure 30 as part of a medical instrument 16 (FIG. 1), according to one embodiment. The flexible printed circuit 20 is a flexible substrate that includes patterned metal traces 22a, 22b with an electromagnet structure 30 affixed thereto. Such a medical instrument may be used autonomously, or it may be installed within, or as a part of, another device.

The flexible printed circuit 20 has a length, a width, and a thickness. The flexible printed circuit 20 has a substantially flat top surface, and a substantially flat opposing (i.e., bottom) surface. In some cases, the flexible printed circuit 20 has a plurality of layers that together form the thickness of the flexible printed circuit 20. In some cases, one or more traces are arranged on a first layer of the flexible printed circuit 20 and one or more different traces are arranged on a second layer. Additional traces, electrodes, or other printed circuit features may be formed on still other layers.

The length of the flexible printed circuit 20 may be five times the width, 10 times the width, 20 times the width, or some greater number times the width. The width may be about four millimeters (4 mm), five millimeters (5 mm), 10 mm, 20 mm or another width. The thickness of the flexible printed circuit 20 may be about one millimeter (1 mm) or less, two millimeters (2 mm) or less, four millimeters (4 mm) or less, or another thickness. In at least one embodiment, the flexible printed circuit 20 has a length of about 250 centimeters (250 cm), a width of about one centimeter (1 cm), and a thickness of about 0.5 mm. Other dimensions are contemplated.

As illustrated, the flexible printed circuit 20 includes metal traces 22a, 22b. The metal traces 22a, 22b run substantially along the length of the flexible printed circuit 20 from ancillary circuitry 40 in one portion of the flexible printed circuit 20 to the electromagnet structure 30 in an opposing, different portion of the flexible printed circuit 20. A first end of each of the metal traces 22a, 22b is electrically coupled to the ancillary circuitry 40, and a second opposing end of each of the metal traces 22a, 22b is electrically coupled to a corresponding lead connector 26 (e.g., metal trace 22a is connected to lead connector 26a and metal trace 22b is connect to different lead connector 26b). In various embodiments, each lead connector 26 has a solderable pad through which a wire-like conductor (e.g., a wire) can pass, or be attached, and to which the wire-like conductor can be electrically coupled.

The electromagnet structure 30 includes a core 32 and a conductive coil 34, as described herein. The conductive coil 34 is wound around the core 32 such that the ends of the conductive coil 34 are on opposite ends of the core 32 and are parallel to one another as they extend perpendicular to the linear dimension of the core 32. The ends, or leads 36, of the conductive coil 34 pass through, or are otherwise electrically connected to, corresponding lead connectors 26 of the metal traces 22a, 22b on the flexible printed circuit 20. For example, lead 36a of the conductive coil 34 is electrically connected (e.g., soldered) to lead connector 26a of metal trace 22a, and an opposing lead 36b of the conductive coil 34 is soldered to a corresponding lead connector 26b of metal trace 22b. In some cases, the opposing leads 36 of the conductive coil 34 are electrically connected (e.g., soldered) at the surface of the flexible printed circuit 20 to metal traces 22a, 22b without passing through the flexible printed circuit 20.

The ancillary circuitry 40 may be arranged separate from the flexible printed circuit 20. For example, as illustrated in certain ones of the figures herein, the ancillary circuitry 40 may include a multi-pin header into which a cooperating connector is plugged. Alternatively, or in addition, ancillary circuitry 40 may be arranged in a single containment structure (e.g., a housing) electrically and mechanically coupled to the flexible printed circuit 20. For simplicity and to avoid confusion, the header illustrated in certain ones of the figures (e.g., FIGS. 2A, 3A, 4A) is representative of a header, a header plus additional circuitry, and circuitry without a header.

The ancillary circuitry 40 includes additional electrical logic (e.g., passive or active electronic components, batteries, connectors, other electrical and electro-mechanical hardware or components, and the like) for driving the excitation signals through the conductive coil 34 of the electromagnet structure 30 via metal traces 22a, 22b to generate a magnetic field about the electromagnet structure 30. In some embodiments, the ancillary circuitry 40 may include control circuit 14 (FIG. 1) to control the excitation signal, and the sensor 12 for detecting the generated magnetic field information. In at least one such embodiment, the ancillary circuitry 40 can receive signals from sensor 12 (FIG. 1) or send signals to presentation system 18 via a wired or wireless connection.

In other embodiments, the control circuit 14 (FIG. 1) may be separate from, or external to, the ancillary circuitry 40. In at least one such embodiment, the ancillary circuitry 40 operates as a converter, adaptor, or other connector for receiving signals, via wired or wireless connection, from the control circuit 14. In this way, the control circuit separately communicates with the sensor 12 and the presentation system 18 independent of the medical instrument 16.

In various embodiments, the ancillary circuitry 40 can include an internal power source (e.g., batteries). Alternatively, or in addition, the ancillary circuitry 40 may be connected to an external power source (e.g., a 3-conductor cable to a computer or other electronic device) to receive power.

The ancillary circuitry 40 connects to the flexible printed circuit 20 and is electrically coupled to the metal traces 22. For example, ancillary circuitry 40 includes electrical components that are configured to pass an electrical current to flow through the metal traces 22a, 22b and through the conductive coil 34 of the electromagnet structure 30. As described herein, this electrical current may be referred to as an excitation signal, which has a particular waveform over time.

When a current passes through the conductive coil 34, the conductive coil 34 generates a magnetic field. The magnetic field has a direction based on the direction of flow of the current through the conductive coil 34. As the direction of the current changes, the direction of the magnetic field also changes. As the excitation signal traverses its particular waveform over time, the magnetic field will correspondingly form, grow, and collapse based on the electrical current associated with the excitation signal. The magnetic field generated by the electromagnet structure 30 enables detection and tracking of the medical instrument 16, and generation of information that represents the position of the medical instrument 16 (see FIG. 1) within the body of the patient. It is beneficial to be able to detect the position, orientation, and movement of the medical instrument 16 at any depth within the body of the patient.

In various embodiments, only a portion of the medical instrument 16 (FIG. 1) is configured to be inserted into the body of a patient. For example, a first portion of the medical instrument that includes the electromagnet structure 30 is configured to be inserted into the body of a patient, while a second portion that includes the ancillary circuitry 40 is configured to remain outside the body of the patient. In yet other embodiments, the entire portion of the medical instrument may be configured to be inserted or implanted into the body of the patient.

Figure 3A:
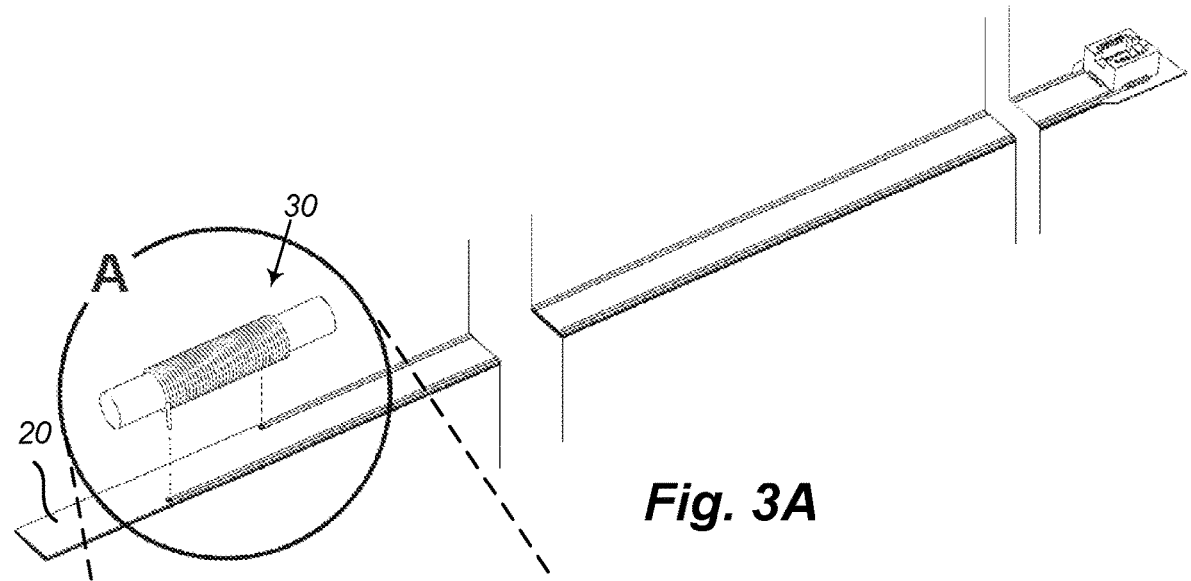
FIGS. 3A-3B are illustrations of assembly of a flexible printed circuit with an electromagnet structure, according to one embodiment.
Figure 3B:
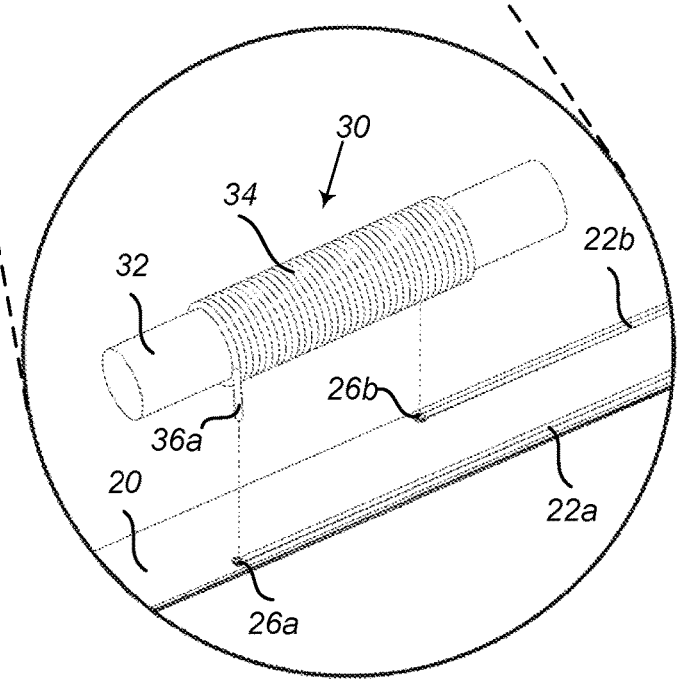

FIGS. 3A-3B are illustrations of assembly of a flexible printed circuit 20 with an electromagnet structure 30, according to one embodiment. The flexible printed circuit 20 and electromagnet structure 30 assembly illustrated in FIGS. 3A-3B is an embodiment of the flexible printed circuit 20 and electromagnet structure 30 assembly described herein in conjunction with FIGS. 2A-2C. As illustrated, electromagnet structure 30 includes a core 32 with a conductive coil 34 wrapped around or convoluted (i.e., wound) around the core 32. The ends of the wire-like conductor that forms the conductive coil 34 are extended away from the core 32 to create leads 36 that are electrically coupled to corresponding metal traces 22a, 22b of flexible printed circuit 20.

The flexible printed circuit 20 is patterned with metal traces 22a and 22b. The metal traces 22a, 22b are electrically coupled to corresponding lead connectors 26a, 26b, respectively. The leads 36 of the conductor coil 34 of the electromagnet structure 30 pass through the corresponding lead connectors 26a, 26b. For example, as illustrated, lead 36a passes through lead connector 26a, and an opposing lead (not illustrated, but illustrated as lead 36b in FIGS. 2B-2C) passes through lead connector 26b. Once the leads 36 are passed through the corresponding lead connectors 26, the leads 36 are then soldered to the lead connectors 26 to create an electrical connection between the metal traces 22a, 22b and the conductive coil 34.

Figure 4:
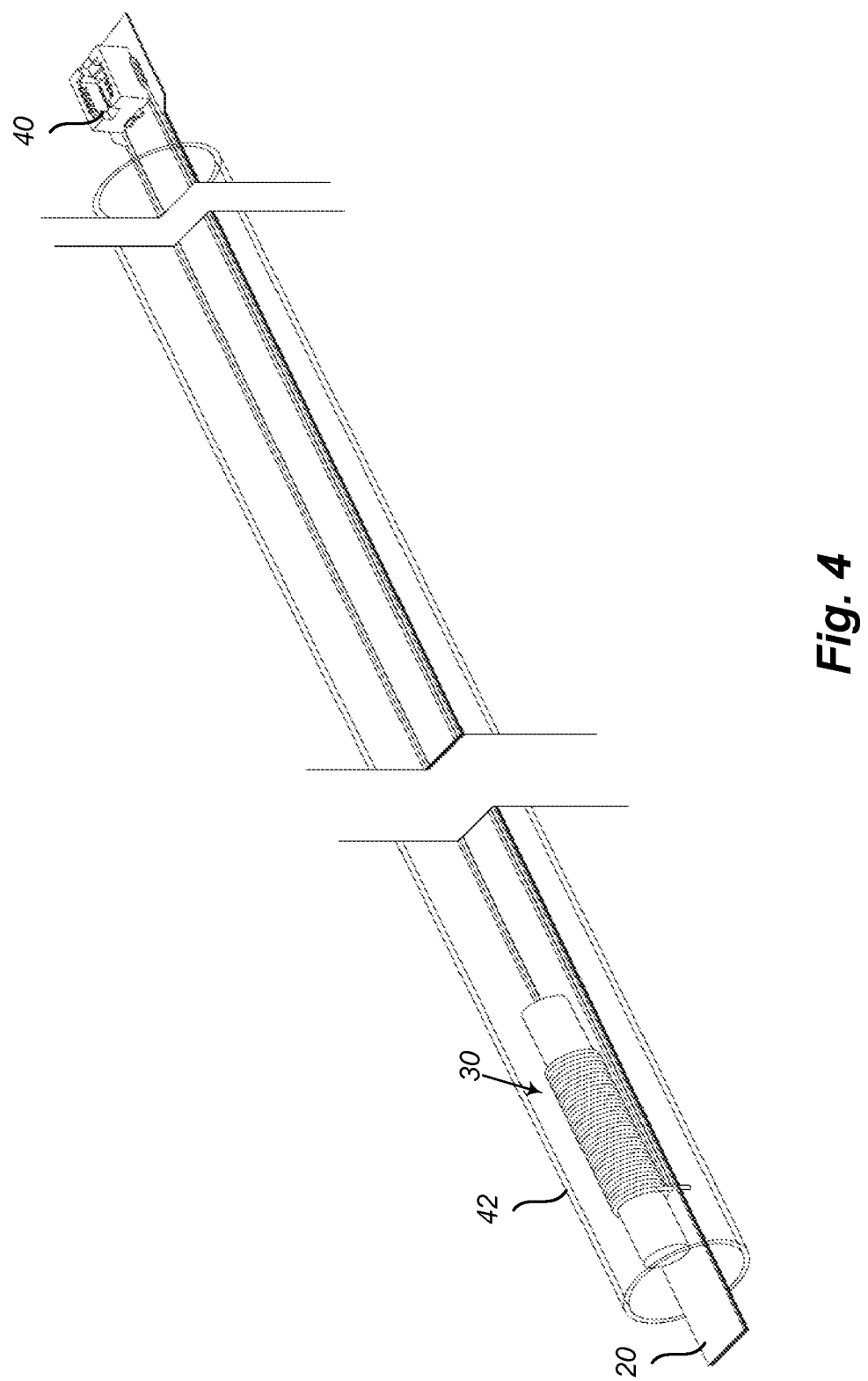
FIG. 4 is an illustration of a flexible printed circuit with an electromagnet structure within a tubing of a medical instrument, according to one embodiment.

FIG. 4 is an illustration of a flexible printed circuit 20 with an electromagnet structure 30 within a tube-like structure. In FIG. 4, the tube-like structure is arranged as tubing 42, according to one embodiment. The flexible printed circuit 20 and electromagnet structure 30 assembly illustrated in FIG. 4 is an embodiment of the flexible printed circuit 20 and electromagnet structure 30 assembly described herein in conjunction with FIGS. 2A-2C. In various embodiments, at least a first portion of the flexible printed circuit 20 with the electromagnet structure 30 that is inserted into the patient's body is contained within the tubing 42.

In the illustration, the tubing 42 encases a substantial portion of the flexible printed circuit 20 without encasing the ancillary circuitry 40. However, in other embodiments, the tubing 42 may be shorter and only encase the electromagnet structure 30 and the portion of the flexible printed circuit 20 that is connected to the electromagnet structure 30. In yet other embodiments, other dimensions or lengths of tubing 42 may also be utilized to contain various different portions or sections of the flexible printed circuit 20. Tubing 42 may also have exposed or excised sections allowing for regional or localized exposure of portions of the flexible printed circuit to be exposed to the body. The tubing 42 may be heat-shrink tubing or other polymer tubing that prevents the flexible printed circuit 20 and electromagnet structure 30 from being exposed to the body of the patient in which the medical instrument 16 (FIG. 1) with the flexible printed circuit 20 is being inserted.

Figure 5A:
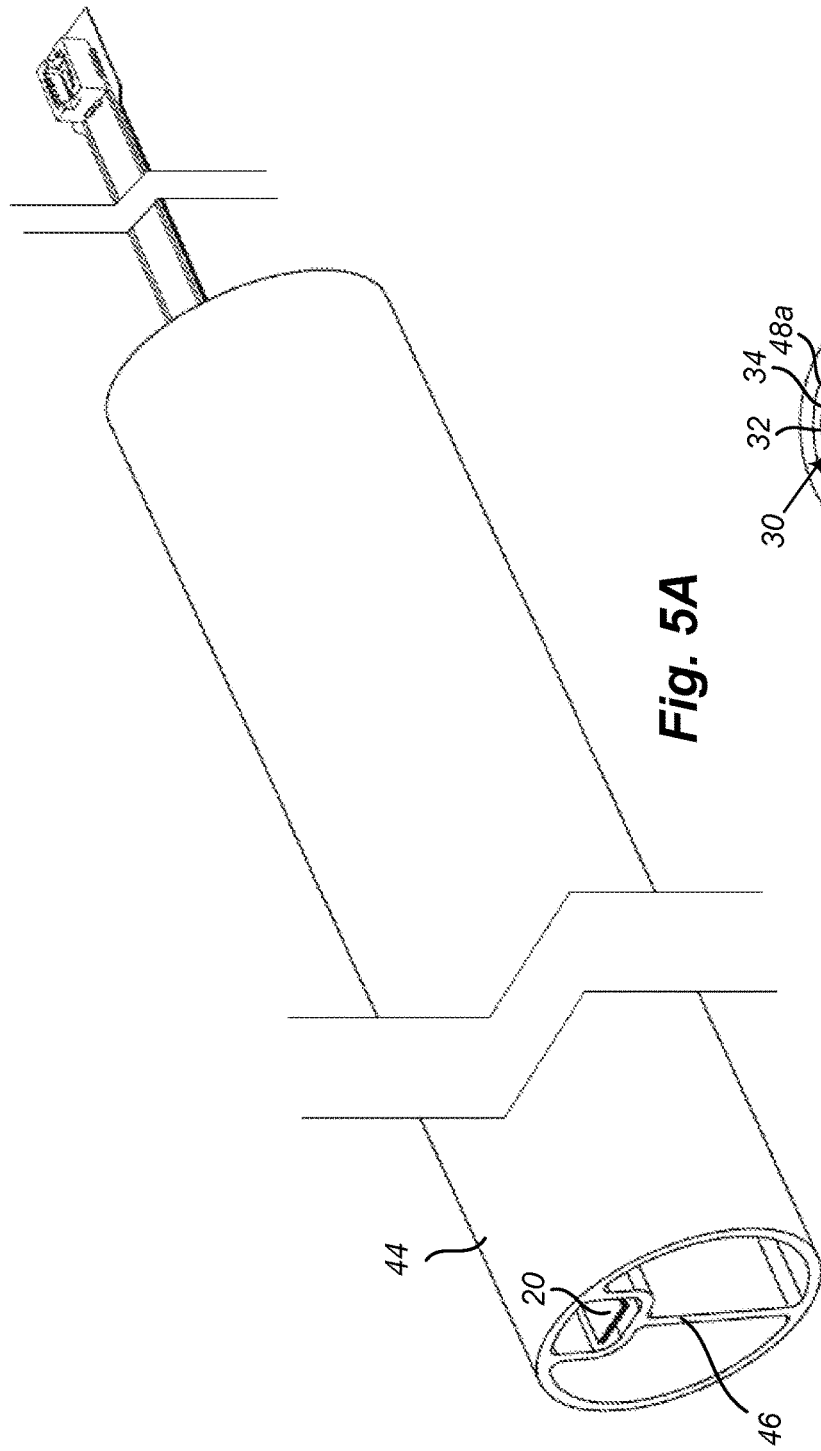
FIGS. 5A-5B are illustrations of a flexible printed circuit with an electromagnet structure within a tri-lumen catheter of a medical instrument, according to one embodiment.
Figure 5B:
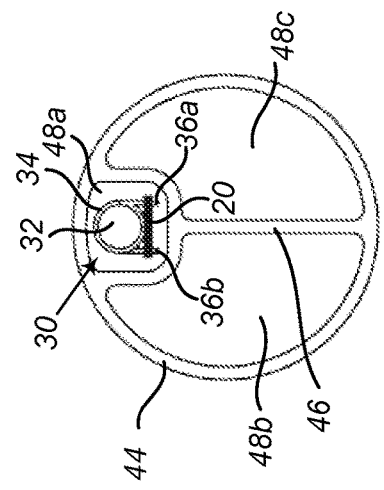

FIGS. 5A-5B are illustrations of a flexible printed circuit 20 with an electromagnet structure 30 within a containment structure having the form of a multi-lumen catheter. The catheter may have any acceptable number of lumens; however in FIGS. 5A-5B, the multi-lumen catheter is a tri-lumen catheter 44, according to one embodiment. Similar to FIG. 4, the flexible printed circuit 20 and electromagnet structure 30 assembly illustrated in FIGS. 5A-5B is an embodiment of the flexible printed circuit 20 and electromagnet structure 30 assembly described herein in conjunction with FIGS. 2A-2C. However, in this illustrated example, at least a first portion of the flexible printed circuit 20 with the electromagnet structure 30 is encased within the tri-lumen catheter 44. The tri-lumen catheter 44 includes a catheter support 46 that runs substantially through the length of the catheter 44, which creates three cavities 48a-48c that each extends the length of the catheter 44. In this illustrated example, the support 46 creates a y-like formation inside the catheter 44 with the cavity 48a being in the "gap" of the y-like formation. The flexible printed circuit 20 and electromagnet structure 30 are positioned inside the cavity 48a of the catheter 44.

Similar to what is shown in FIG. 4, catheter 44 extends substantially along of the length of the flexible printed circuit 20 with the ancillary circuitry 40 not being encased or positioned inside the catheter 44. However, in other embodiments, the catheter 44 may be shorter and only encase the electromagnet structure 30 and the portion of the flexible printed circuit 20 that is connected to the electromagnet structure 30. In yet other embodiments, other dimensions or lengths of catheter 44 may also be utilized to cover various different portions or sections of the flexible printed circuit 20. In any event, the catheter 44 is structured to prevent the flexible printed circuit 20 and electromagnet structure 30 from being exposed to the body of the patient in which the medical instrument 16 (FIG. 1) with the flexible printed circuit 20 is being inserted, and to allow for fluids to flow through the catheter 44 without interacting with the flexible printed circuit 20 or the electromagnet structure 30.

Figure 6:
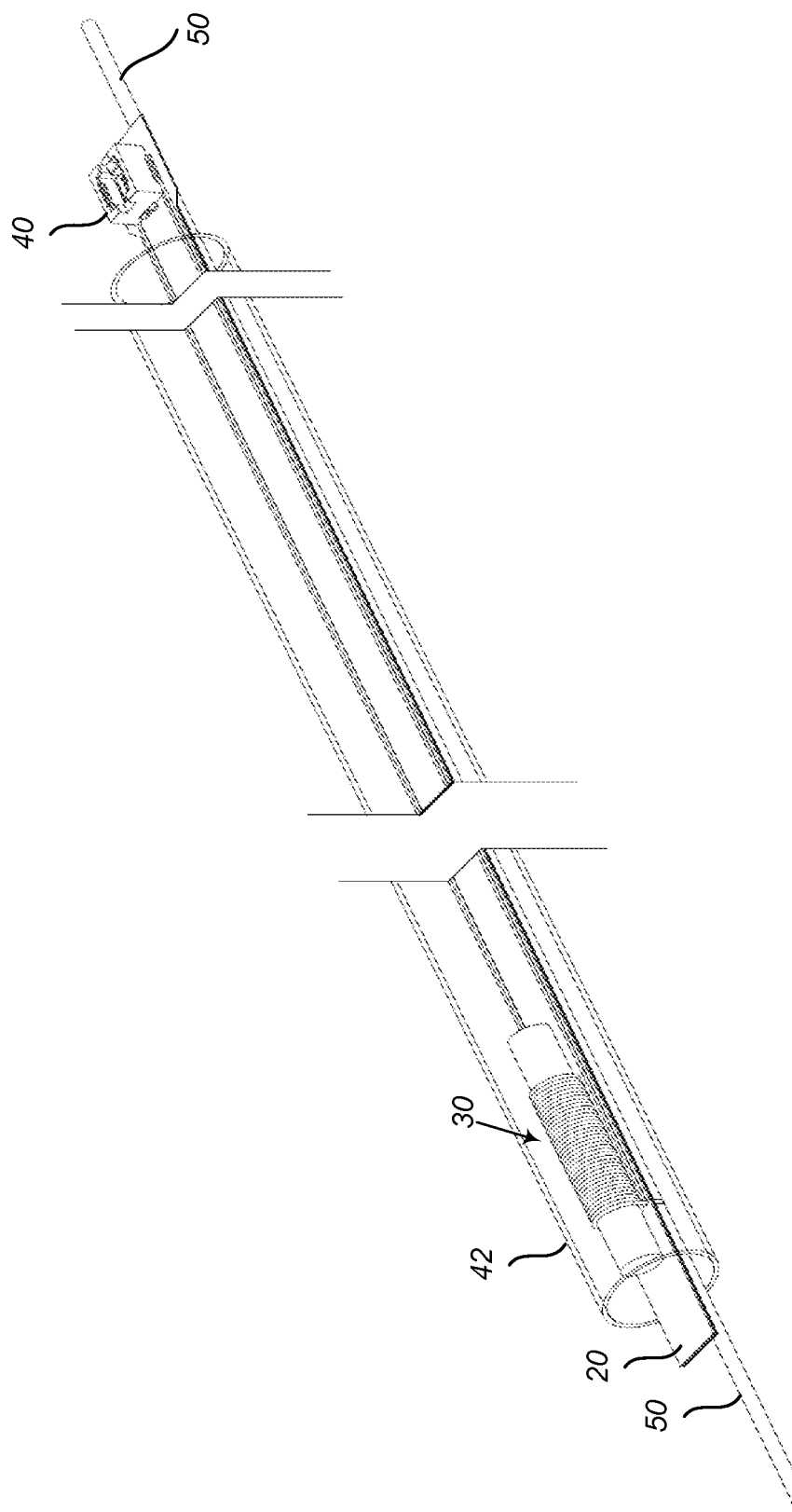
FIG. 6 is an illustration of a flexible printed circuit with an electromagnet structure and a wire electrode within a tubing of a medical instrument, according to one embodiment.

FIG. 6 is an illustration of a flexible printed circuit 20 with an electromagnet structure 30 and a wire electrode 50 arranged within a tube-like structure, which may be tubing 42, according to one embodiment. Similar to FIG. 4, the flexible printed circuit 20, electromagnet structure 30, and tubing 42 assembly illustrated in FIG. 6 is an embodiment of the flexible printed circuit 20, electromagnet structure 30, and tubing 42 assembly described herein in conjunction with FIG. 4. However, in this illustrated example, the assembly also includes a wire electrode 50.

The wire electrode 50 is structured to provide a mechanical stiffness or support to the medical instrument 16 (FIG. 1)) linearly along the length of the flexible printed circuit 20. Different thicknesses or materials may be used to change the amount of stiffness applied to the medical instrument. In various embodiments, the wire electrode 50 is positioned on a side of the flexible printed circuit 20 that is opposite the electromagnet structure 30, as illustrated. In this way, the wire electrode 50 has less impact on the magnetic field generated by the electromagnet structure 30. However, in other embodiments, the wire electrode 50 may be positioned on the same side of the flexible printed circuit 20 as the electromagnet structure 30.

In some embodiments, the wire electrode 50 extends along the entire length of the flexible printed circuit 20. In other embodiments, the wire electrode 50 does not extend the full length of the flexible printed circuit 20. In some other embodiments, the wire electrode 50 extends beyond the length of the flexible printed circuit 20, as illustrated. However, in yet other embodiments, the wire electrode 50 extends beyond the flexible printed circuit 20 at the one end of the flexible printed circuit 20, but not the other. For example, in one embodiment, the wire electrode 50 extends beyond the flexible printed circuit 20 on the end with the ancillary circuitry 40, but not the end with the electromagnet structure 30. But in another embodiment, the wire electrode 50 extends beyond the flexible printed circuit 20 at the end with the electromagnet structure 30 but not the end with the ancillary circuitry 40.

In some embodiments, the wire electrode 50 is a single component running along the length of the flexible printed circuit 20. In other embodiments, the wire electrode 50 is a plurality of segments that each run along some or all of the length of the flexible printed circuit 20 providing regional stiffness along the length of the flexible printed circuit 20. The number and position of wire electrodes along the length of the flexible printed circuit 20 is dependent on the desired stiffness of the various portions of the medical instrument 16 (FIG. 1) or desired joints or bendable portions or positions of the medical instrument.

In various embodiments, the wire electrode 50 is electrically coupled to the ancillary circuitry 40 to capture electrical measurements within the body. For example, in some cases, one or more electrodes are arranged as electrodes that are used in cooperation with the ancillary circuitry 40 or other circuitry to measure the electrical potential of the patient's heart during an electrocardiogram procedure.

FIGS. 7A-7C are illustrations of a flexible printed circuit 20 with an electromagnet structure 30 and a wire electrode 50 within a tri-lumen catheter 44, according to one embodiment. Similar to FIGS. 5A-5B, the flexible printed circuit 20, electromagnet structure 30, and tri-lumen catheter 44 assembly illustrated in FIGS. 7A-7C is an embodiment of the flexible printed circuit 20, electromagnet structure 30, and tri-lumen catheter 44 assembly described herein in conjunction with FIGS. 5A-5B. Accordingly, the catheter 44 includes a support 46 that creates three cavities 48a-48c that substantially run the length of the catheter 44. However, in this illustrated example, the assembly also includes a wire electrode 50, similar to what is described herein in conjunction with FIG. 6.

As discussed in more detail herein, the wire electrode 50 is structured to provide a mechanical stiffness or support to the medical instrument 16 (FIG. 1)) linearly and substantially along the length of the flexible printed circuit 20. Different thicknesses or materials may be used to change the amount of stiffness applied to the medical instrument, or for other reasons. As illustrated, the wire electrode 50 is positioned on a side of the flexible printed circuit 20 that is opposite the electromagnet structure 30 and in the same cavity 48a. In this way, the wire electrode 50 provides the desired stiffness to the medical instrument, while also not impacting the functionality of the other cavities 48b, 48c of the tri-lumen catheter 44.

Moreover, similar to what is described herein, the wire electrode 50 extends substantially along the length of the flexible printed circuit 20. In some embodiments, the wire electrode 50 extends the entire length of the flexible printed circuit 20. In other embodiments, the wire electrode 50 does not extend the full length of the flexible printed circuit 20. In some other embodiments, the wire electrode 50 extends beyond the length of the flexible printed circuit 20, as illustrated. However, in yet other embodiments, the wire electrode 50 extends beyond the flexible printed circuit 20 at the one end of the flexible printed circuit 20 but not the other. For example, in one embodiment, the wire electrode 50 extends beyond the flexible printed circuit 20 on the end with the ancillary circuitry 40 but not the end with the electromagnet structure 30. But in another embodiment, the wire electrode 50 extends beyond the flexible printed circuit 20 at the end with the electromagnet structure 30 but not the end with the ancillary circuitry 40.

Again, the wire electrode 50 may be a single component or a plurality of segments that each run along the length of the flexible printed circuit 20 providing regional stiffness along the length of the flexible printed circuit 20.

Figure 8:
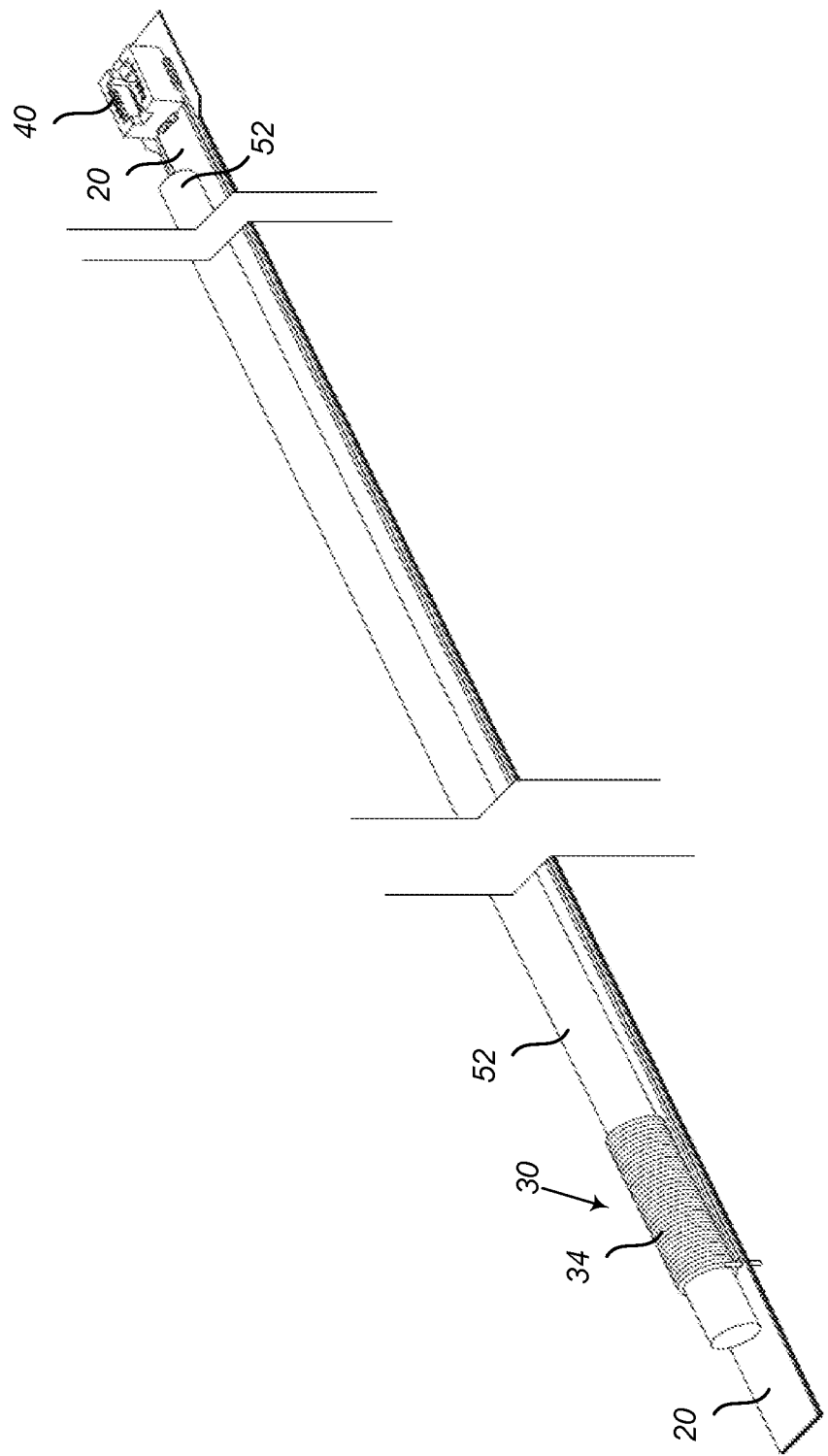
FIG. 8 is an illustration of a flexible printed circuit with an electromagnet structure having an extended core, according to one embodiment.

FIG. 8 is an illustration of a flexible printed circuit 20 with an electromagnet structure 30 having an extended core 52, according to one embodiment. The flexible printed circuit 20 and electromagnet structure 30 assembly illustrated in FIG. 8 is an embodiment of the flexible printed circuit 20 and electromagnet structure 30 assembly described herein in conjunction with FIGS. 2A-2C. However, the electromagnet structure 30 of the assembly illustrated in FIG. 8 includes a core 52 that extends substantially along a length of the flexible printed circuit 20 with the conductive coil 34 only wrapping around a portion of the core 52 that is distal from the ancillary circuitry 40. In this embodiment, the extension of the core 52 along the length of the flexible printed circuit 20 provides a mechanical stiffener to the medical instrument 16 (FIG. 1) similar to the electrode 50 described herein in conjunction with FIGS. 6 and 7A-7C.

Various embodiments of the assembly illustrated in FIG. 8 may be combined with other embodiments described herein. For example, the extended core 52 may be utilized in the electromagnet structure 30 of the assemblies illustrated in FIGS. 4 and 5A-5B.

Figure 9:
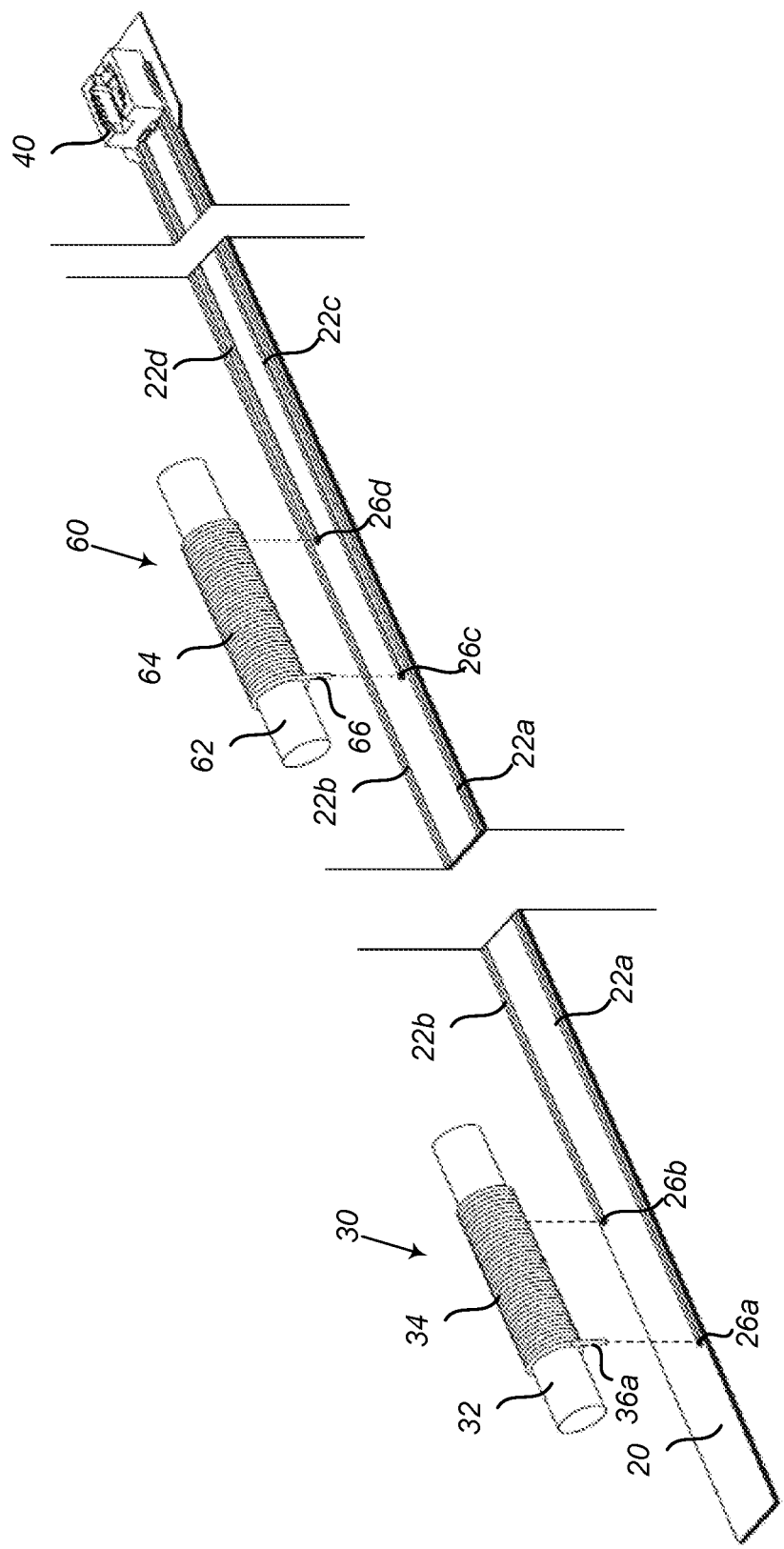
FIG. 9 is an illustration of a flexible printed circuit with multiple electromagnet structures, according to one embodiment.
Figure 11A:
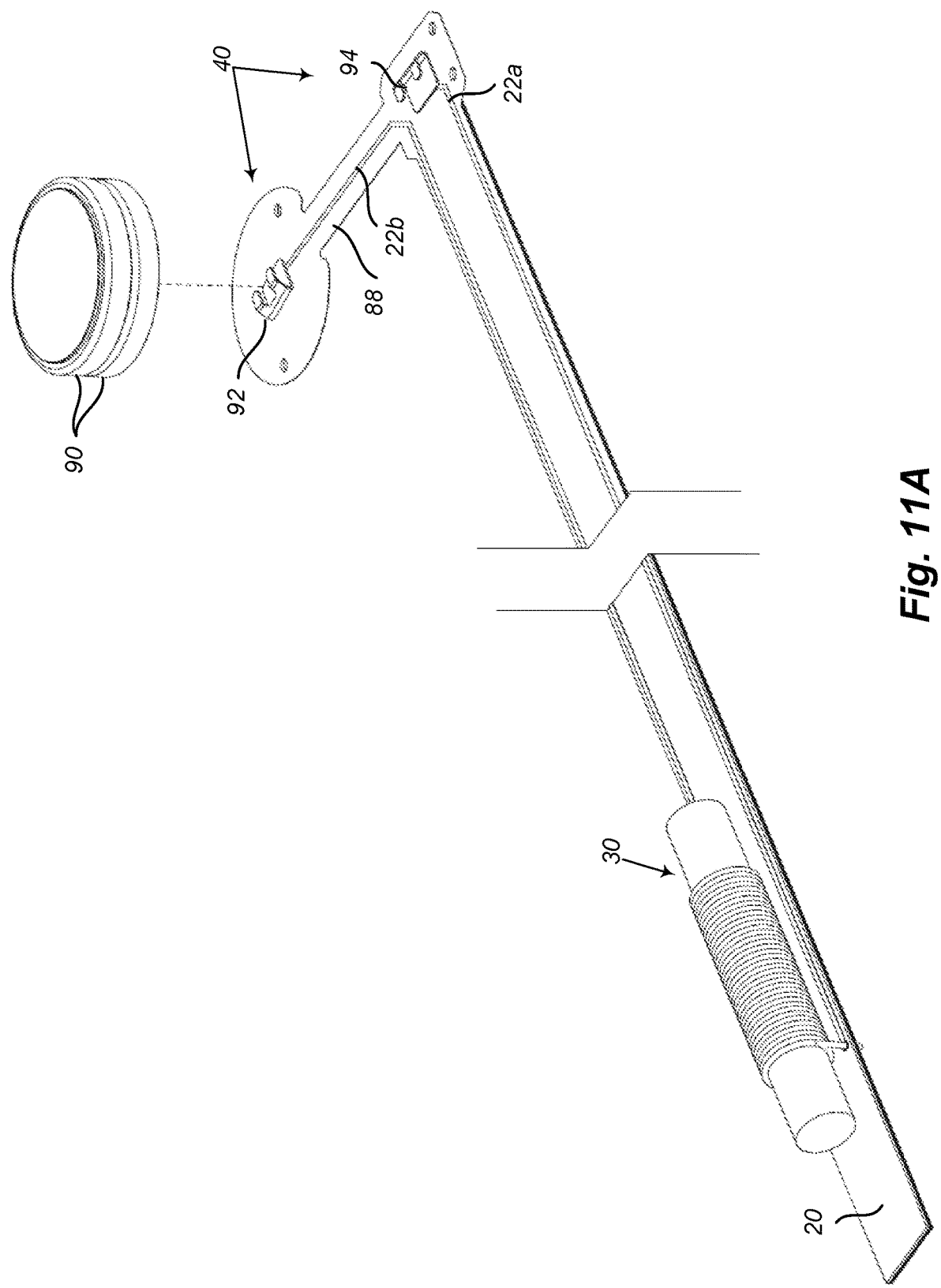
Figure 11B:
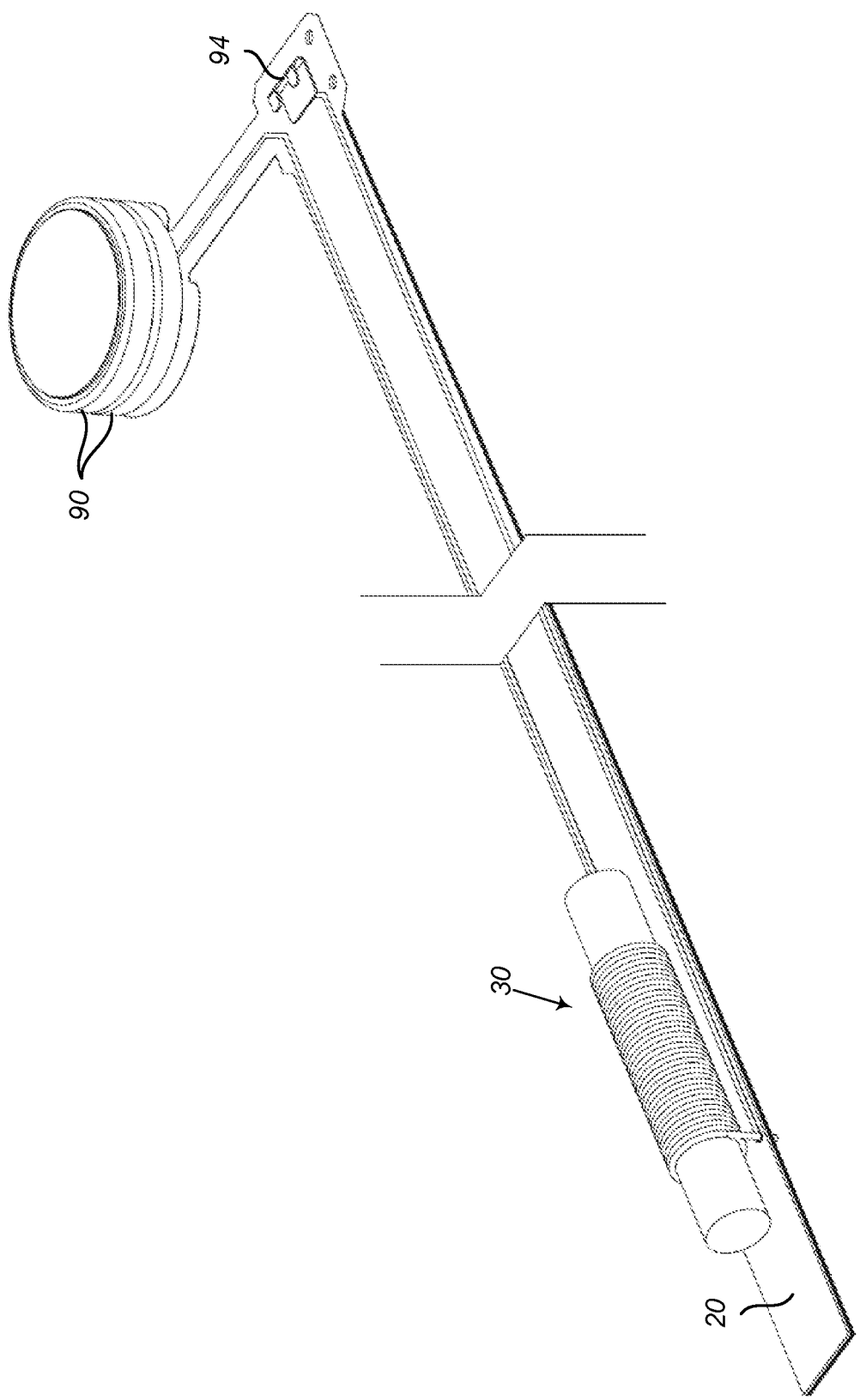
Figure 11C:
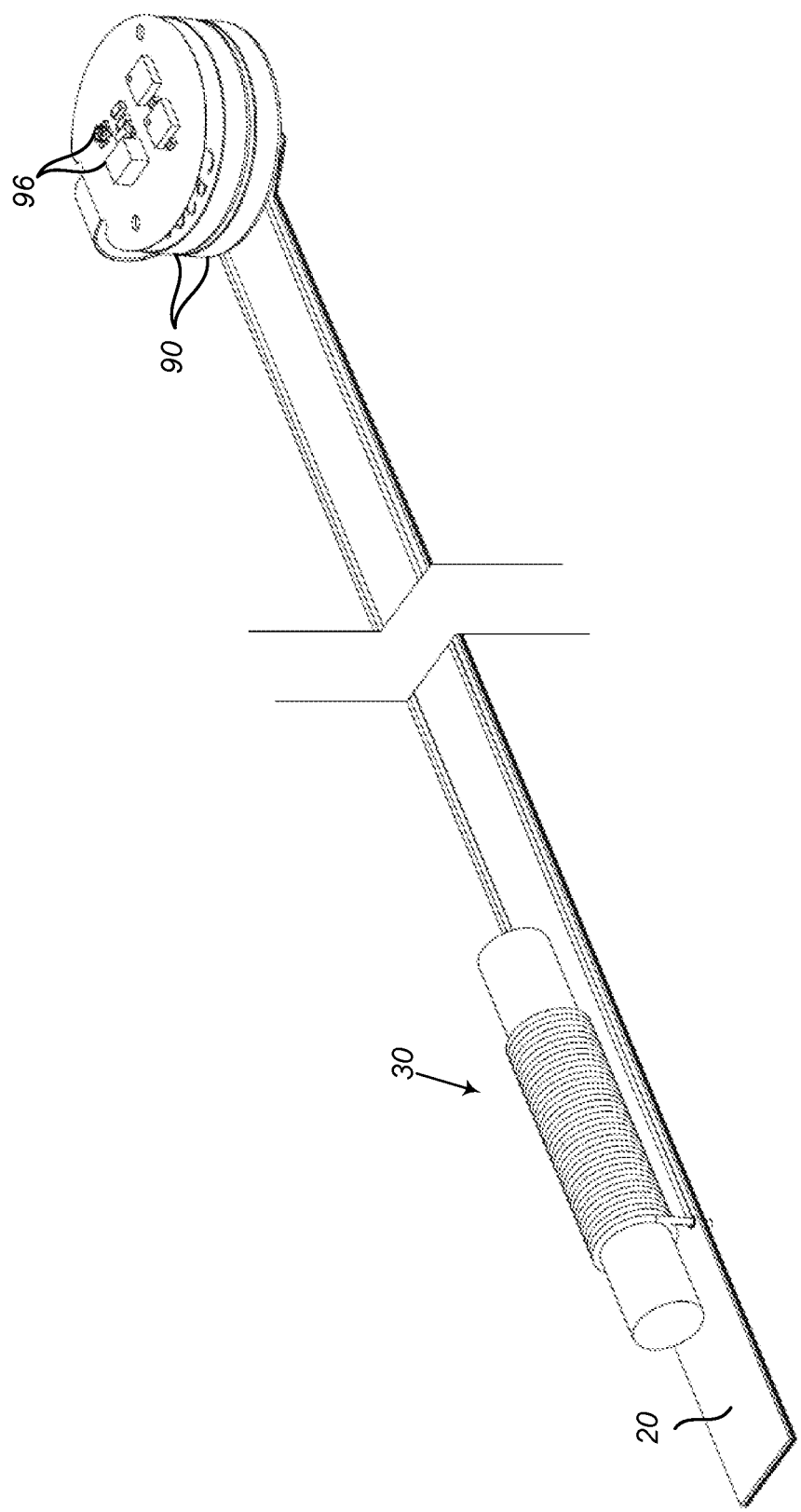

FIG. 9 is an illustration of a flexible printed circuit 20 with multiple electromagnet structures 30, 60, according to one embodiment. The flexible printed circuit 20 and electromagnet structure 30 assembly illustrated in FIG. 9 is an embodiment of the flexible printed circuit 20 and electromagnet structure 30 assembly described herein in conjunction with FIGS. 2A-2C. However, the assembly illustrated in FIG. 9 also includes a second electromagnet structure 60 that is similar to electromagnet structure 30 described herein.

In this illustrated embodiment, the flexible printed circuit 20 includes metal traces 22a, 22b for electromagnet structure 30 and metal traces 22c, 22d for electromagnet structure 60. The metal traces 22a, 22b run substantially along the length of the flexible printed circuit 20 from the ancillary circuitry 40 to the electromagnet structure 30, as described herein. The metal traces 22c, 22d run substantially along the length of the flexible printed circuit 20 from ancillary circuitry 40 to electromagnet structure 60. In various embodiments, the lengths of the metal traces 22a, 22b are longer than the metal traces 22c, 22d. In this way, electromagnet structure 30 is positioned on the flexible printed circuit 20 further from the ancillary circuitry 40 than electromagnet structure 60.

A first end of each of the metal traces 22c, 22d is electrically coupled to the ancillary circuitry 40, and a second opposing end of each of the metal traces 22c, 22d is electrically coupled to a corresponding lead connector 26 (e.g., metal trace 22c is connected to lead connector 26c and metal trace 22c is connect to a different lead connector (not illustrated)).

The electromagnet structure 60 is similar to electromagnet structure 30, and includes a core 62 and a conductive coil 64. The conductive coil 64 is wrapped around the core 62 such that the ends of the conductive coil 64 are on opposite ends of the core 62 and are parallel to one another as they extend perpendicular to the length of the core 62. The ends, or leads 66, of the conductive coil 64 pass through and are electrically connected to corresponding lead connectors 26 of the metal traces 22c, 22d on the flexible printed circuit 20. For example, lead 66 of the conductive coil 64 is electrically connected (e.g., soldered) to lead connector 26c of metal trace 22c, and an opposing lead of the conductive coil 64 is soldered to a corresponding lead connector (not illustrated) of metal trace 22d.

Optionally, in some cases, the electromagnet structure 30 and the electromagnet structure 60 share a common core structure, similar to what is described below in conjunction with FIG. 22A.

In various embodiments, the electromagnet structures 30, 60 are controlled together such that they receive the same excitation signal. In various other embodiments, each electromagnet structure 30, 60 is individually controllable. Ancillary circuitry 40, or control circuit 14 (FIG. 1), includes various circuit components to control the separate flow of electrical current to each electromagnet structure 30, 60. The separate control of electrical current allows for separate or distinct excitation signals to be sent to each electromagnet structure 30, 60 via their corresponding metal traces 22a, 22b and 22c, 22d, respectively. As described herein, the excitation signal traverses its particular waveform over time, the magnetic field will correspondingly form, grow, and collapse based on the electrical current associated with the excitation signal, the distance the current has to travel, the materials and dimensions of the various structures, and other such parameters. By providing separate or distinct excitation signals to the separate electromagnet structures 30, 60, the magnetic field generated by electromagnet structures 30, 60 can be different at any given point in time, which allows for the sensor 12 (FIG. 1) to detect the separate magnetic fields. By sensing different magnetic fields, the position, orientation, and movement of various different portions (i.e., where the different electromagnet structures 30, 60 are positioned along the length of the flexible printed circuit) of the medical instrument 16 (FIG. 1) is determined at various depths within the body of the patient.

Moreover, although FIG. 9 illustrates two electromagnet structures, embodiments are not so limited, and in other embodiments, three or more electromagnet structures may be utilized along the length of the flexible printed circuit.

FIGS. 10A-10B are illustrations of a flexible printed circuit 20 with an electromagnet structure 30 and a containment structure arranged as housing 80 with ancillary circuitry 40, according to one embodiment. The flexible printed circuit 20 and electromagnet structure 30 assembly illustrated in FIGS. 10A-10B is an embodiment of the flexible printed circuit 20 and electromagnet structure 30 assembly described herein in conjunction with FIGS. 2A-2C, but with housing 80 to encase ancillary circuitry 40.

As described herein, the ancillary circuitry 40 optionally includes additional electrical hardware that connects to the flexible printed circuit 20. For example, ancillary circuitry 40 includes electrical components that are configured to provide an excitation signal to electromagnet structure 30. In various embodiments described herein, the ancillary circuitry 40 is housed, enclosed, or otherwise contained in housing 80. Housing 80 provides a sterile barrier around the ancillary circuitry 40 so that it does not introduce biological contaminants that can infect the patient, and it provides a support barrier so that the ancillary circuitry 40 is not damaged or subject to external forces while medical instrument 16 (FIG. 1) is being utilized.

As described herein, the ancillary circuitry 40 may be integrated in or separate from control circuit 14 (FIG. 1). In some embodiments where the ancillary circuitry 40 and control circuit 14 are separate from one another, ancillary circuitry 40 may connect to control circuit 14 via cable 82. Cable 82 is configured to transmit electrical signals from control circuit 14 to ancillary circuitry 40. In other embodiments, cable 82 transfers electrical power to the ancillary circuitry 40 from a power source (not illustrated). In such an embodiment, the ancillary circuitry 40 is powered via cable 82, but generates the excitation signals itself.

Although FIGS. 10A-10B illustrate the housing 80 with a particular embodiment of flexible printed circuit 20 and electromagnet structure 30 assembly, embodiments are not so limited. Rather housing 80 may be utilized for any embodiment described herein that includes ancillary circuitry 40.

FIGS. 11A-11D are illustrations of a flexible printed circuit 20 with an electromagnet structure 30 assembly with one or more batteries 90. The flexible printed circuit 20 and electromagnet structure 30 assembly illustrated in FIGS. 11A-11D is an embodiment of the flexible printed circuit 20 and electromagnet structure 30 assembly described herein in conjunction with FIGS. 2A-2C. In the illustrated example, however, the ancillary circuitry 40 that connects to flexible printed circuit 20 and provides excitation signals to electromagnet structure 30 also includes one or more batteries 90 and terminals 92, 94.

The flexible printed circuit 20 includes additional flexible printed circuit 88, which is structured to bend so that a positive side of the one or more batteries 90 contacts a positive terminal 92 and a negative side of the one or more batteries 90 contacts a negative terminal 94. The positive terminal 92 connects to the metal trace 22b and the positive terminal 94 connects to metal trace 22a. Additional electrical components 96 are configured to control the flow of electricity from the one or more batteries 90 to generate the excitation signals that are provided to the electromagnet structure 30 via metal traces 22a and 22b. The ancillary circuitry 40 (i.e., the additional flexible printed circuit 88, the one or more batteries 90, and additional electrical components 96) is enclosed in housing 98, which is configured similar to housing 80, described herein.

FIGS. 12-13 are illustrations of various flexible printed circuits 20 with multiple electrode patterns, according to various embodiments. The flexible printed circuit 20 and electromagnet structure 30 assembly illustrated in FIGS. 12-13 is an embodiment of the flexible printed circuit 20 and electromagnet structure 30 assembly described herein in conjunction with FIGS. 2A-2C.

In FIG. 12, however, the flexible printed circuit 20 also includes electrode pattern 100. In this illustrated example, the electrode 100 is patterned on the side of the flexible printed circuit 20 that is opposite the electromagnet structure 30. The electrode 100 is positioned near the same distal tip (away from the ancillary circuitry) of the flexible printed circuit 20 as the electromagnet structure 30. Metal trace 102 is patterned into the flexible printed circuit 20 and connects the electrode 100 to the ancillary circuitry (not illustrated). The electrode 100 can pick up electrical signals from the patient's body and transfer them to the ancillary circuitry via metal trace 102 for processing or for transmission to the control circuit for additional processing. This single patterned electrode 100 can be used to make or otherwise facilitate in the capture of electrical measurements within the body, such as echocardiogram readings.

FIG. 13 also includes patterned electrodes 104, but in this example, multiple electrodes 104a-104c are patterned into the flexible printed circuit 20. In this illustrated example, the electrodes 104a-104c are patterned on the side of the flexible printed circuit 20 that is opposite the electromagnet structure 30. The electrodes 104a-104c are positioned near the same distal tip (away from the ancillary circuitry) of the flexible printed circuit 20 as the electromagnet structure 30. The electrodes 104 can pick up electrical signals from the patient's body and transfer them to the ancillary circuitry for processing or for transmission to the control circuit for additional processing. These patterned electrodes 104 can be used to make electrical measurements within the body, such as amperometric or cyclic voltametric-type measurements of analytes within the body, in a method analogous to that of a glucose test strip.

Each electrode 104a-104c is electrically coupled to the ancillary circuitry (not illustrated) via a metal trace patterned into the flexible printed circuit 20. In this illustrated example, electrode 104c is electrically coupled to the ancillary circuitry via metal trace 106. Electrodes 104a, 104b are also electrically coupled to the ancillary circuitry via respective metal traces. However, these metal traces are patterned into separate layers of the flexible printed circuit 20 and are thus not illustrated. Accordingly, different electrode configurations can be utilized with different electrodes or traces being constructed in a layered fashion within the flexible printed circuit 20, which also allows for multiple electrodes/connection points in very small spaces.

Figure 14:
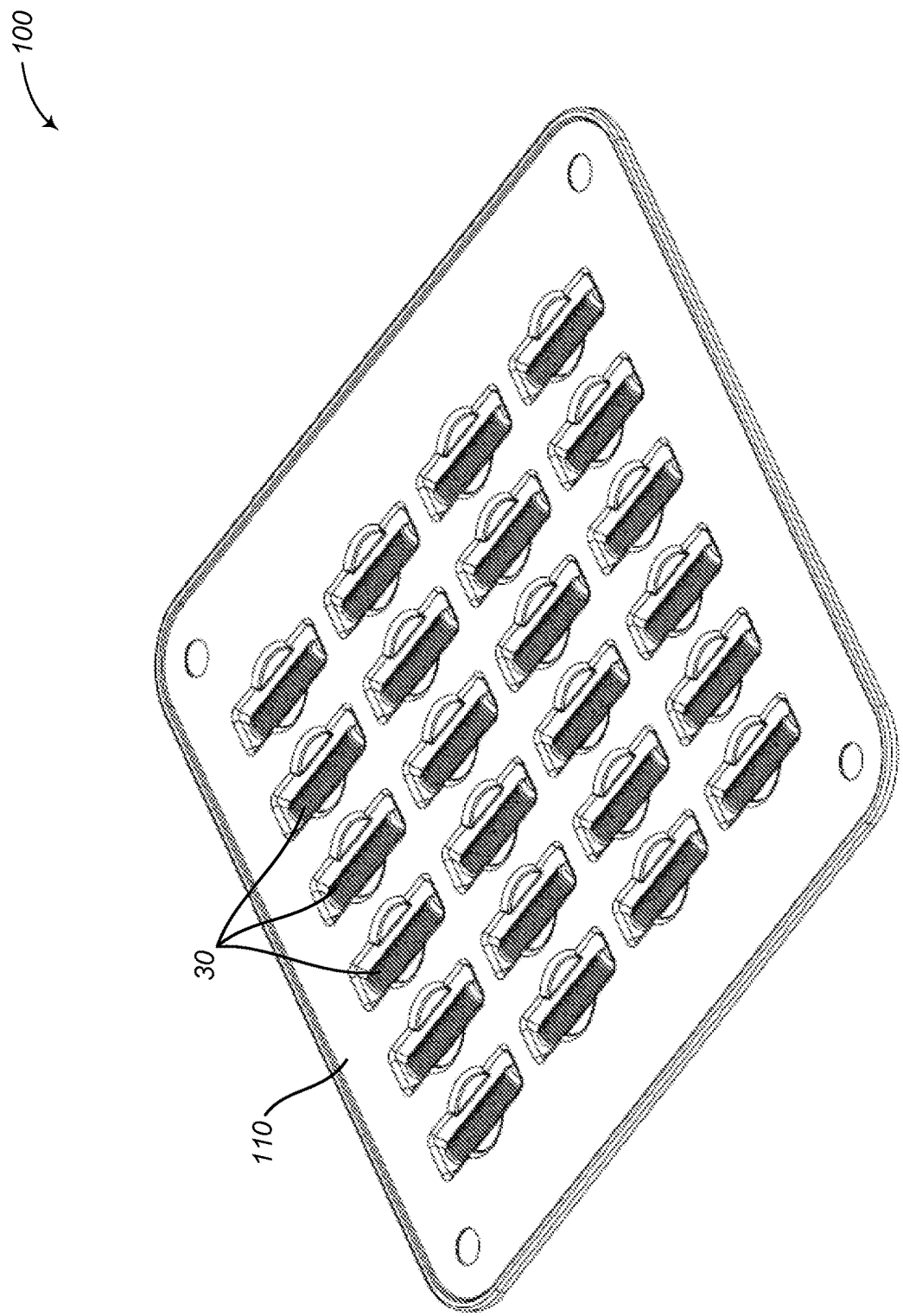
FIG. 14 is an illustration of an assembly tray with electromagnet structure assemblies ready for assembly, according to one embodiment.

FIG. 14 is an illustration of an assembly tray 110 with electromagnet structures 30 ready for assembly, according to one embodiment. In this illustrated example, each separate electromagnet structure 30 is pre-assembled (i.e., the conductive coil is wrapped or otherwise wound around the core) and then positioned into separate pockets in tray 110. Each electromagnet structure 30 is removable from its corresponding tray pocket by human, by a robot, or by some other mechanical tool to be positioned for assembly with a corresponding flexible printed circuit.

For example, each of the plurality of electromagnet structures 30 is formed by winding a wire-like conductor into a respective coil around a respective core, with the wire-like conductor of the respective coil having two opposing ends (a first of the two opposing ends is arranged as a first lead of the respective coil and a second of the two opposing ends is arranged as a second lead of the respective coil), as described herein. The plurality of electromagnet structures 30 are then arranged on the assembly tray 110. In various embodiments, the plurality of electromagnet structures 30 are positioned such that their orientation is substantially similar on the assembly tray 110.

Figure 15A:
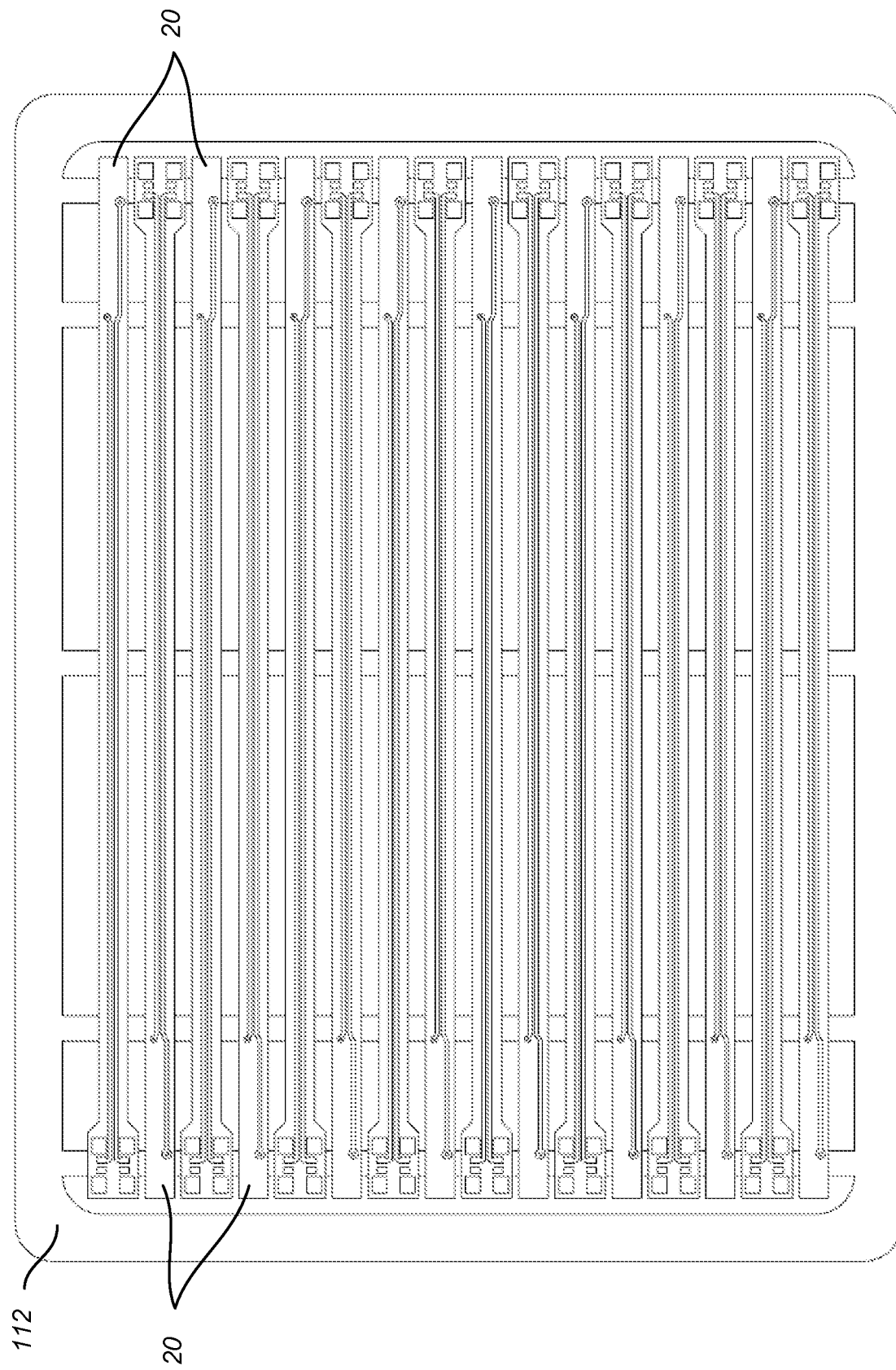
FIGS. 15A-15B are illustrations of an assembly tray with a plurality of flexible printed circuits ready for assembly, according to one embodiment.
Figure 15B:
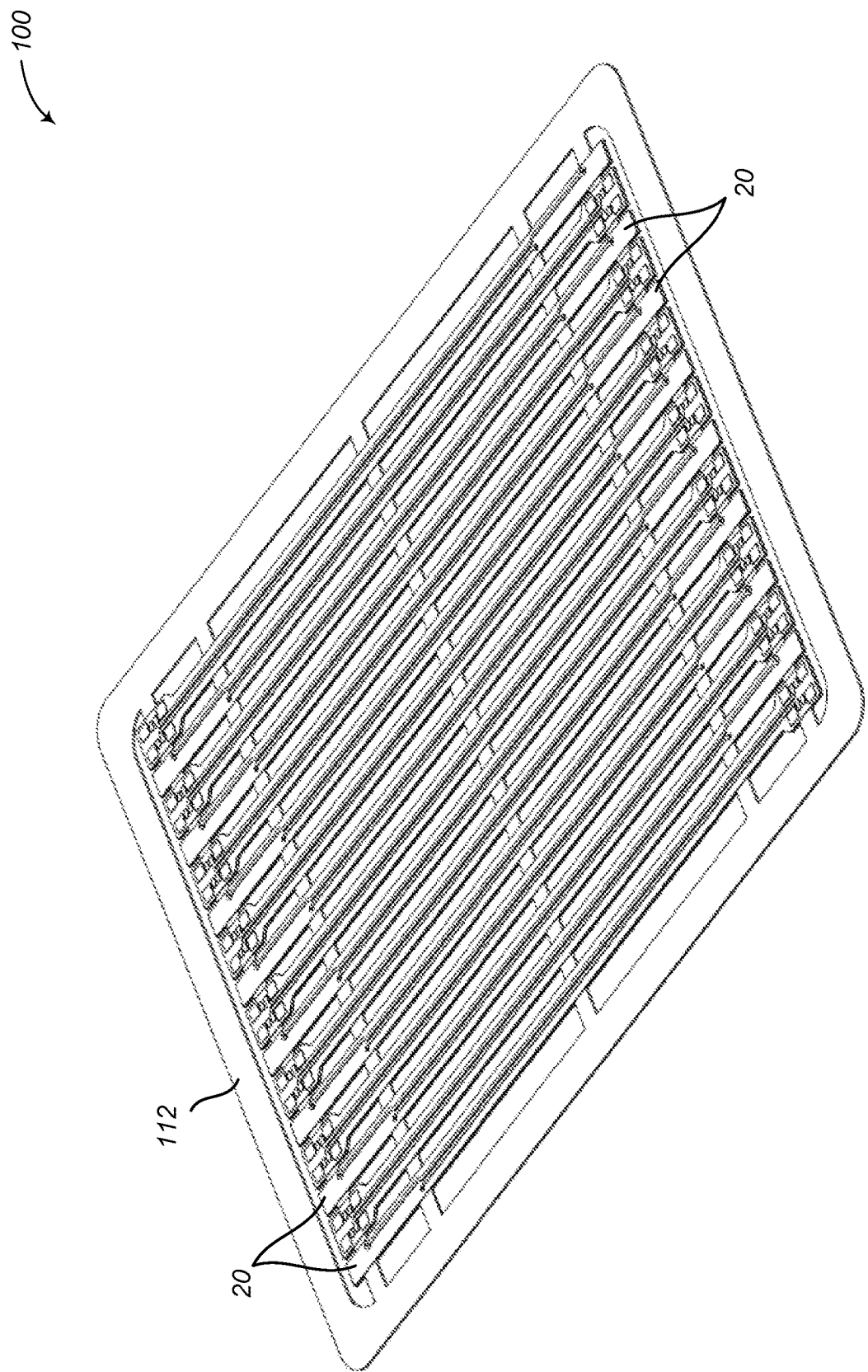

FIGS. 15A-15B are illustrations of an assembly panel 112 with a plurality of flexible printed circuits 20 ready for assembly, according to one embodiment. In various embodiments, multiple flexible printed circuits 20 are formed in a panelized configuration for automated assembly. In various embodiments, the flexible printed circuits 20 are pre-formed prior to connecting corresponding electromagnet structures and ancillary circuitry to each flexible printed circuit.

For example, the assembly panel 112 of plurality of flexible printed circuits 20 is formed such that each respective flexible printed circuit has patterned therein a first metal trace and a second metal trace running linearly along a substantial length of a flexible substrate to form the respective flexible printed circuit, each of the first and second metal traces having a first end and a second end, as described herein. In various embodiments, the plurality of flexible printed circuits 20 are formed such that their orientation is substantially similar in the assembly panel 112, or alternating orientations, as shown.

Figure 16:
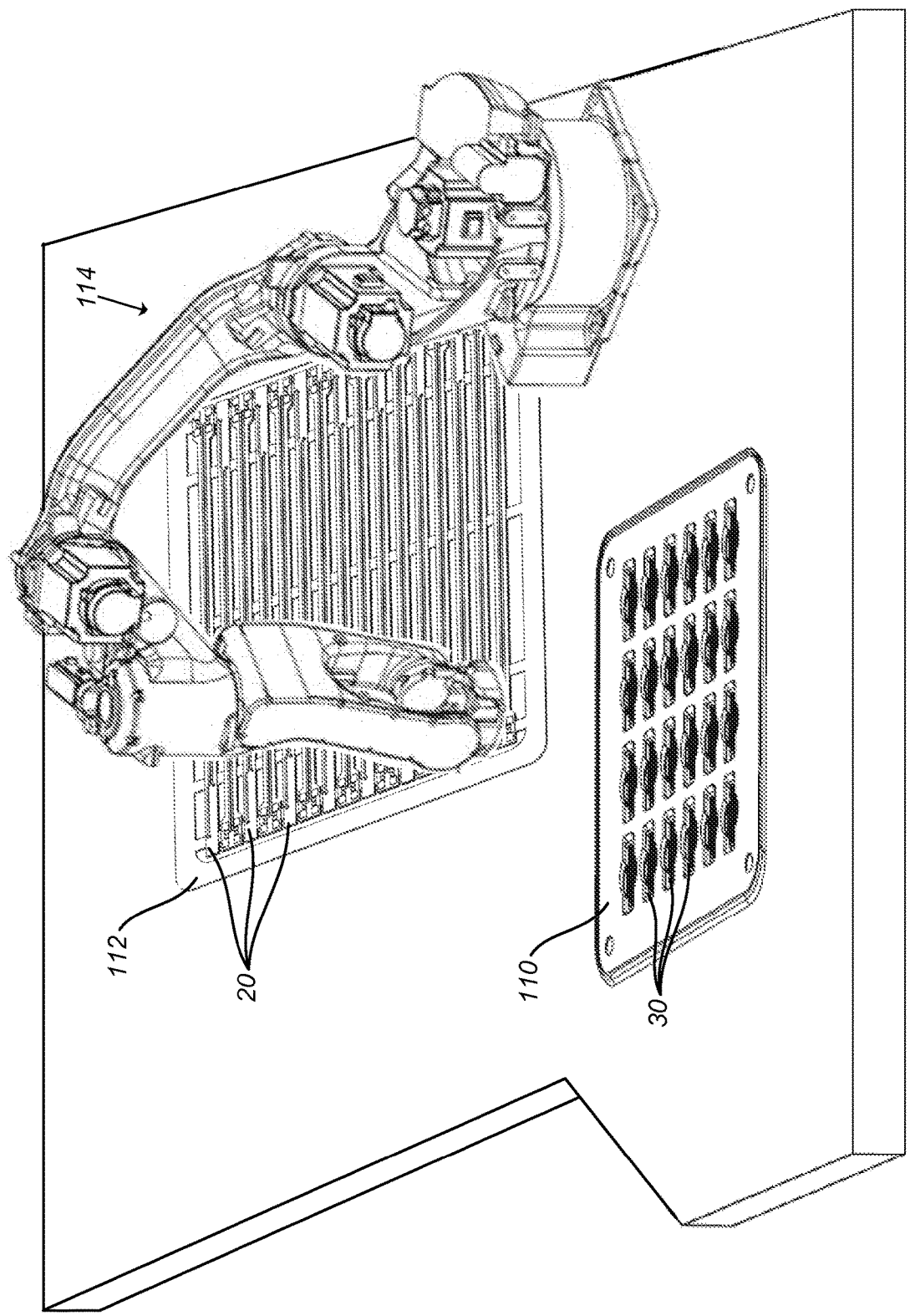
FIG. 16 is an illustration of an assembly robot, according to one embodiment.

FIG. 16 is an illustration of an assembly robot 114, according to one embodiment. Assembly robot 114 is positioned to pick-and-place electromagnet structures 30 from tray 110 and onto corresponding flexible printed circuits 20 in the panel 112. Solder paste is pre-applied to electrical component mounting pads (e.g., lead connectors 26) on the flexible printed circuits 20. The robot 114 picks up an electromagnet structure 30 from tray 110. In some embodiments, the robot 114 is affixed with a magnet, or some other assembly tool, to pick up the electromagnet structure out of the pocket of the tray 110 in a predetermined orientation. The robot 114 repositions itself to place the electromagnet structure 30 into its corresponding location on a respective flexible printed circuit 20. The robot 114 can also pick-and-place other circuit components, e.g., ancillary circuitry (not illustrated), in their respective locations on the flexible printed circuit 20. It should be noted that the entire panelized assembly may be placed in an oven for solder reflow during one or more steps of the assembly process.

For example, the robot 114 may position one or more corresponding pairs of electromagnet structure 30 and flexible printed circuit 20 by pairs at a time. For each pair, the robot 114 removes an electromagnet structure from the assembly tray 110 and aligns it with a corresponding flexible printed circuit in the panel 112 with the first lead of the coil of the electromagnet structure positioned with the first end of the first metal trace of the corresponding flexible printed circuit and the second lead of the coil of the electromagnet structure positioned with the first end of the second metal trace of the corresponding flexible printed circuit, as described herein. The first lead of the coil of the electromagnet structure is electrically connected to the first end of the first metal trace of the corresponding flexible printed circuit, and the second lead of the coil of the electromagnet structure is electrically connected to the first end of the second metal trace of the corresponding flexible printed circuit. Corresponding ancillary circuitry is positioned on the corresponding flexible printed circuit at an opposite end from the electromagnet structure, and the corresponding ancillary circuitry is electrically connected to the second end of the first metal trace of the corresponding flexible printed circuit and to the second end of the second metal trace of the corresponding flexible printed circuit.

As described in the present disclosure, embodiments are directed towards a medical instrument that includes a flexible printed circuit with an electromagnet structure such that the electromagnet structure is tracked as the medical instrument is advanced through the body of patient. The following description and corresponding figures describe alternative embodiments for manufacturing and connecting the electromagnet structure and the flexible printed circuit.

FIGS. 17A-17B are illustrations of an electromagnet structure 118 as part of a medical instrument 16 (FIG. 1), according to one embodiment. The electromagnet structure 118 includes a core 120 with a wire 128 wrapped around the core 120. The core 120 is a ferrous-based core structure similar to core 32 described herein. In various embodiments, the core 120 is coated with an electrically insulating material (e.g., polymer, oxide, etc.). Similarly, in some embodiments, the wire 128 is coated with an electrically insulating material. In at least one embodiment, the melting point of the insulation on the wire 128 is lower than the melting point of the insulation on the core 120. In this way, the insulation on the wire 128 can be removed at specific locations (e.g., lead contacts for soldering) without removing or damaging the insulation on the core 120.

As illustrated, the core 120 has a first end portion 130 and a second end portion 132. The wire 128 is wrapped around and along the length of the core 120 from the first end portion 130 towards the second end portion 132 to create multiple different coil segments. As the wire 128 is wrapped around the core 120, the pitch of the coils is adjusted, to structure and define the different coil segments. The pitch is the tightness between consecutive coils of the wire 128 as it is wrapped around the core 120 (i.e., the number of coils per unit length of the core). Accordingly, a tighter or lower pitch has consecutive coils that are closer together then a looser or higher pitch (i.e., a tighter pitch has more coils per unit length than a loose pitch).

In various embodiments, the wire 128 is wrapped around the core 120 by advancing (e.g., pushing, pulling, or the like) the core 120 along its central axis and circumferentially wrapping the wire 128 around the central axis of the core 120. The pitch of the coils is adjusted by changing the rate of speed at which the core 120 is advanced along its central axis, changing the rate of speed at which the wire 128 is circumferentially wrapped around the core 120, or both. For example, the pitch may be increased (or made looser) by increasing the speed at which the core 120 is advanced along its central axis or by decreasing the speed at which the wire 128 is circumferentially wrapped around the core 120. Conversely, the pitch may be decreased (or made tighter) by decreasing the speed at which the core 120 is advanced along its central axis or by increasing the speed at which the wire 128 is circumferentially wrapped around the core 120.

As the wire 128 is wrapped around the core 120, the pitch of the wire 128 is adjusted to create different coil segments. The electromagnet structure 118 includes five primary coil segments structured over the length of the core 120: first and second lead contacts 122a, 122b; first and second contact/coil gaps 126a, 126b; and a conductive coil 124. The first lead contact 122a and the conductive coil 124 are separated by the first contact/coil gap 126a, and the conductive coil 124 and the second lead contact 122b are separated by the second contact/coil gap 126b. The first and second contact/coil gaps 126a, 126b create thermal insulation sections between the conductive coil 124 and the first and second lead contacts 122a, 122b.

The first and second lead contacts 122a, 122b and the conductive coil 124 are structured by the wire 128 having a tight or low pitch, whereas the first and second contact/coil gaps 126a, 126b are structured by the wire 128 having a loose or high pitch. Accordingly, the pitch of the first and second lead contacts 122a, 122b and the conductive coil 124 is tighter than the pitch of the first and second contact/coil gaps 126a, 126b. In various embodiments, the pitch of each coil segment is substantially consistent throughout the length of the coil segment. In other embodiments, however, the pitch may be different at various parts throughout a coil segment.

The following is an example of one assembly embodiment of electromagnet structure 118. Starting at a first end portion 130 of the core 120, the wire 128 is wrapped around the core 120 multiple times with a tight pitch to create the first lead contact 122a. The pitch of wrapping is then adjusted such that the wire 128 is wrapped around the core 120 multiple times with a loose pitch to create the first contact/coil gap 126a. This loose pitch wrapping creates the thermal insulation section between the first lead contact 122a and the conductive coil 124. The conductive coil 124 is then created by wrapping the wire 128 around the core 120 multiple times with a tight pitch. The length of the conductive coil 124 is longer than the first lead contact 122a (i.e., the number of wraps to create the conductive coil 124 is substantially more than the number of wraps to create the first lead contact 122a). In one non-limiting example, the length of the conductive coil 124 is approximately 50 to 1000 times longer than the length of the first lead contact 122a. The pitch of wrapping is then adjusted such that the wire 128 is wrapped around the core 120 multiple times with a loose pitch to create the second contact/coil gap 126b, similar to the first contact/coil gap 126a. This loose pitch wrapping creates the thermal insulation section between the conductive coil 124 and the second lead contact 122b. The second lead contact 122b is then created by wrapping the wire 128 around the core 120 multiple times with a tight pitch, similar to the first lead contact 122a.

After the wire 128 is wrapped around the core 120 to create the five coil sections of the electromagnet structure 118, an adhesive compound is applied to mechanically bond the conductive coil 124 to the core 120, which is illustrated in FIG. 17B. For example, the adhesive compound 129a is applied to the junction between the conductive coil 124 and the first contact/coil gap 126a, and the adhesive compound 129b is applied to the junction between the conductive coil 124 and the second contact/coil gap 126b. The adhesive compound 129a, 129b encapsulates the wire 128 and the core 120, which mechanically bonds the conductive coil 124 to the core 120.

Figure 18:
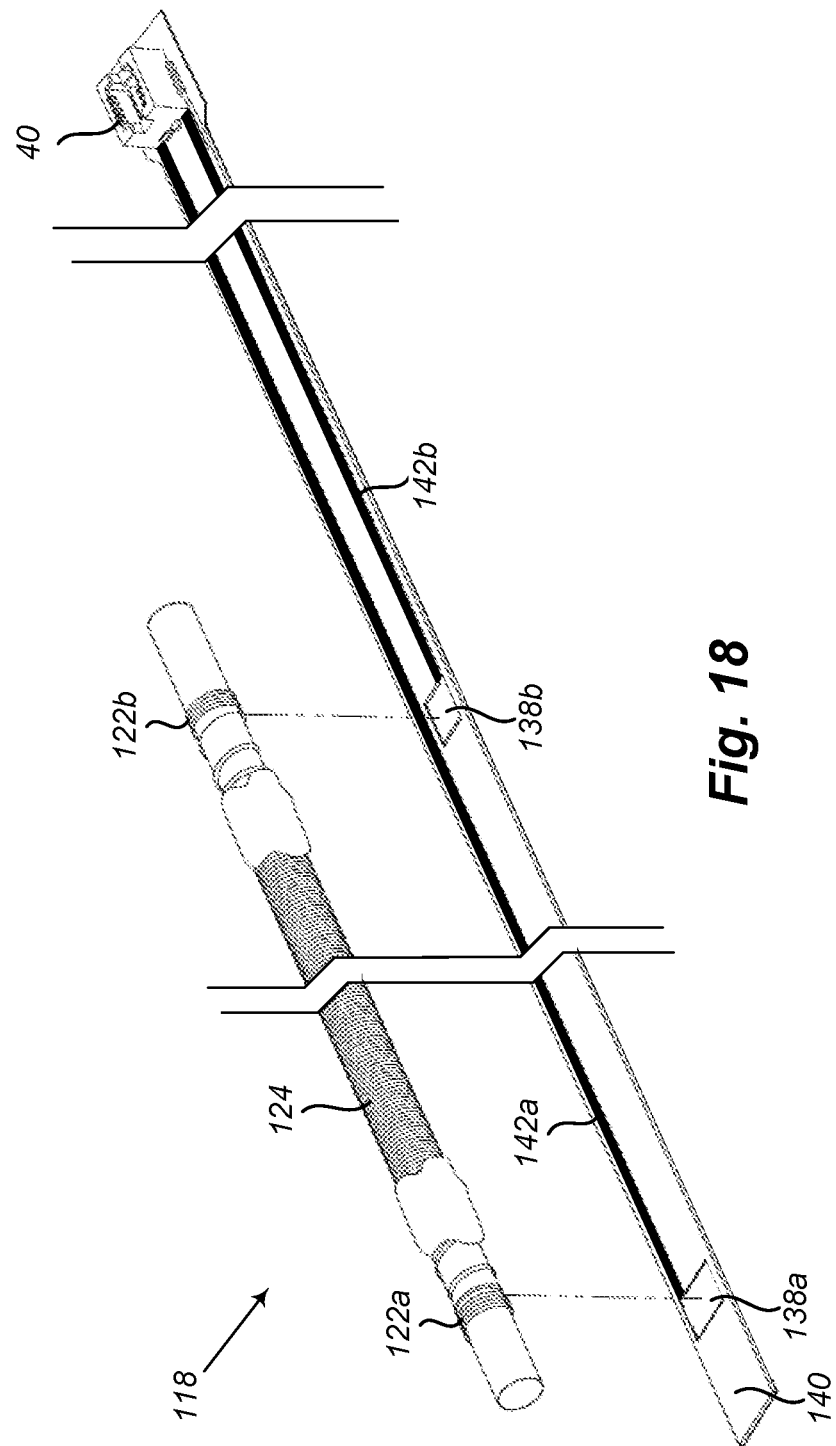
FIG. 18 is an illustration of a flexible printed circuit with an electromagnet structure as part of a medical instrument, according to one embodiment.

FIG. 18 is an illustration of a flexible printed circuit 140 with an electromagnet structure 118 as part of a medical instrument 16 (see FIG. 1), according to one embodiment. The flexible printed circuit 140 is a flexible substrate that includes patterned metal traces 142a, 142b and contact pads 138a, 138b with an electromagnet structure 118 affixed thereto.

The flexible printed circuit 140 has a length, a width, and a thickness, which may be similar to that which is described herein with reference to flexible printed circuit 20. Similarly, the flexible printed circuit 140 has a substantially flat top surface, and a substantially flat opposing (i.e., bottom) surface. In some cases, the flexible printed circuit 140 has a plurality of layers that together form the thickness of the flexible printed circuit 140. In some cases, one or more traces are arranged on a first layer of the flexible printed circuit 140 and one or more different traces are arranged on a second layer. Additional traces, electrodes, or other printed circuit features may be formed on still other layers.

As illustrated, the flexible printed circuit 140 includes metal traces 142a, 142b, similar to the metal traces 22a, 22b described herein. The metal traces 142a, 142b run substantially along the length of the flexible printed circuit 140 from ancillary circuitry 40 in one portion of the flexible printed circuit 140 to the electromagnet structure 118 in an opposing, different portion of the flexible printed circuit 140. A first end of each of the metal traces 142a, 142b is electrically coupled to the ancillary circuitry 40, and a second opposing end of each of the metal traces 142a, 142b is electrically coupled to a corresponding contact pad 138 (e.g., metal trace 142a is connected to contact pad 138a and metal trace 142b is connected to different contact pad 138b). In various embodiments, each contact pad 138a, 138b is a solderable pad to which a corresponding lead contact 122a, 122b can be electrically coupled.

As described herein, the electromagnet structure 118 is created by wrapping a wire 128 (see FIG. 17A) around a core 120 (see FIG. 17A) at different pitches to create, among other coil segments, the conductive coil 124, the first lead contact 122a, and the second lead contact 122b. The lead contacts 122a, 122b are electrically coupled to the respective metal traces 142a, 142b on the flexible printed circuit 140 via the respective contact pads 138a, 138b on the flexible printed circuit 140. For example, lead contact 122a is electrically connected (e.g., soldered) to contact pad 138a of metal trace 142a, and lead contact 122b is electrically connected (e.g., soldered) to contact pad 138b of metal trace 142b.

Similar to what is described herein, ancillary circuitry 40 is electrically coupled to the metal traces 142a, 142b to pass an electrical current (e.g., an excitation signal) through the metal traces 142a, 142b and through the conductive coil 124 (via lead contacts 122a, 122b) of the electromagnet structure 118. In this way, an excitation signal with a particular waveform is utilized to cause the conductive coil 124 to generate a magnetic field that correspondingly forms, grows, and collapses based on the electrical current associated with the excitation signal, similar to what is described herein.

Although FIGS. 17A, 17B, and 18 described herein illustrate a single electromagnet structure 118 on the flexible printed circuit 140, embodiments are not so limited. Rather, in some embodiments, multiple electromagnet structures 118 can be assembled on the flexible printed circuit 140, which may be manufactured on a single core prior to assembly on the flexible printed circuit 140.

Figure 19A:
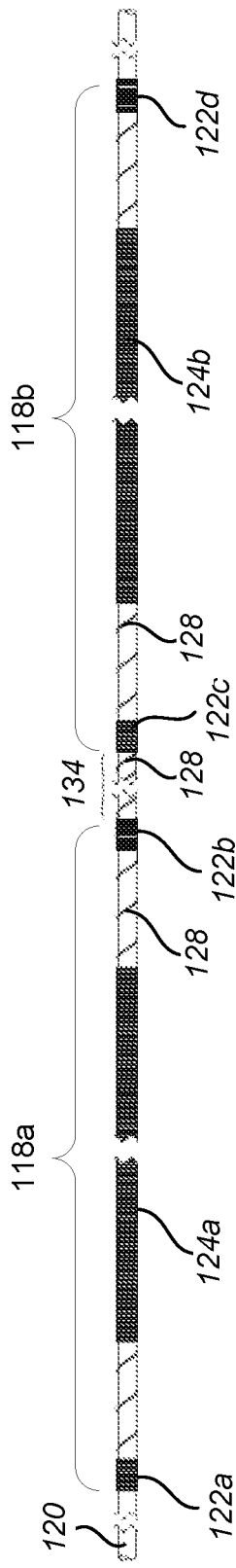
FIGS. 19A-19B are illustrations of multiple electromagnet structures manufactured on a single core, according to one embodiment.
Figure 19B:
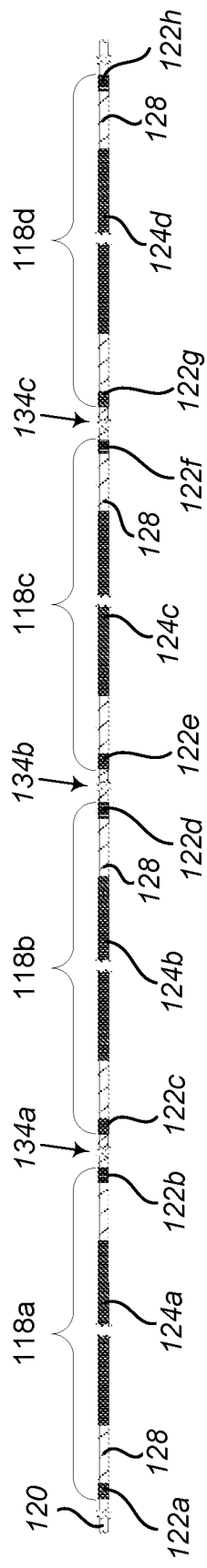

FIGS. 19A-19B are illustrations of multiple electromagnet structures manufactured on a single core, according to one embodiment. As illustrated in FIG. 19A, first and second electromagnet structures 118a, 118b are created on core 120 using wire 128. By employing embodiments described herein with respect to FIGS. 17A-17B, a first electromagnet structure 118a is created by wrapping the wire 128 around the core 120 at different pitches to create a first lead contact 122a, a conductive coil 124a, and a second lead contact 122b. For ease of illustration and discussion, the contact/coil gaps 126 between the lead contacts 122 and the conductive coil 124 are not referenced, and the adhesive compound 129a, 129b that mechanically stabilizes the conductive coil 124 on the core 120 is not illustrated or referenced.

After the first electromagnet structure 118a is created, the wire 128 that was used to create the first electromagnet coil structure 118a is continued (without a break or separation of the wire) and wrapped around the core 120 multiple times with a loose or high pitch to create an electromagnet assembly gap 134. The electromagnet assembly gap 134 creates a buffer or separation between the first electromagnet structure 118a and the second electromagnet structure 118b. The length of the electromagnet assembly gap 134 is dependent on a distance between the first and second electromagnet structures 118a, 118b when attached to the flexible printed circuit 140.

The second electromagnet structure 118b is then created by continuing and wrapping the wire 128 (i.e., the wire 128 that was used to create both the first electromagnet structure 118a and the electromagnet assembly gap 134) around the core 120 in a manner described herein with respect to FIGS. 17A-17B. As a result, a second electromagnet structure 118b is created with a first lead contact 122c, a conductive coil 124b, and a second lead contact 122d for the second electromagnet structure 118b. Again, for ease of illustration and discussion, the contact/coil gaps 126 between the lead contacts 122 and the conductive coil 124 are not referenced, and the adhesive compound 129a, 129b that mechanically stabilizes the conductive coil 124 on the core 120 is not illustrated or referenced.

By creating the first and second electromagnet structures 118a, 118b with the same continuous wire 128 (i.e., with no breaks or separation in the wire 128 between the first electromagnet structure 118a, the electromagnet assembly gap 134, and the second electromagnet structure 118b), a single excitation signal can be utilized to control the magnetic fields generated by both electromagnet structures 118a, 118b. As described in more detail below, the first lead contact 122a of the first electromagnet structure 118a is electrically coupled to a first metal trace on a flexible printed circuit, and the second lead contact 122d of the second electromagnet structure 118b is electrically coupled to a second metal trace on the flexible printed circuit. Ancillary circuitry passes current through both electromagnet structures 118a, 118b via these metal traces.

Although FIG. 19A illustrates two electromagnet structures 118a, 118b assembled on a single core 120, embodiments are not so limited, and other pluralities of electromagnet structures 118 may be assembled on a single core 120. For example, FIG. 19B illustrates an assembly with four electromagnet structures 118a-118d on a single core 120. Similar to what is described herein and employing embodiments described herein, a single continuous wire 128 is wrapped around the core 120 to create four distinct electromagnet structures 118a-118d that are each separated by a respective electromagnet assembly gap 134a-134c. As a result, a first electromagnet structure 118a includes first and second lead contacts 122a, 122b and conductive coil 124a; a second electromagnet structure 118b includes first and second lead contacts 122c, 122d and conductive coil 124b; a third electromagnet structure 118c includes first and second lead contacts 122e, 122f and conductive coil 124c; and a fourth electromagnet structure 118d includes first and second lead contacts 122g, 122h and conductive coil 124d. Again the length of each separate electromagnet assembly gap 134a-134c is dependent on a distance between each respective neighboring electromagnet structures 118a-118d when attached to the flexible printed circuit 140.

By creating the electromagnet structures 118a-118d with the same continuous wire 128 (i.e., with no breaks or separation in the wire 128 between the first electromagnet structure 118a and the fourth electromagnet structure 118b), a single excitation signal can be utilized to control the magnetic fields generated by each electromagnet structure 118a-118d, similar to what is described herein with reference to FIG. 19A. Accordingly, the first lead contact 122a of the first electromagnet structure 118a is electrically coupled to a first metal trace on a flexible printed circuit, and the second lead contact 122h of the fourth electromagnet structure 118d is electrically coupled to a second metal trace on the flexible printed circuit. Ancillary circuitry passes current through the electromagnet structures 118a-118d via these metal traces.

Figure 20:
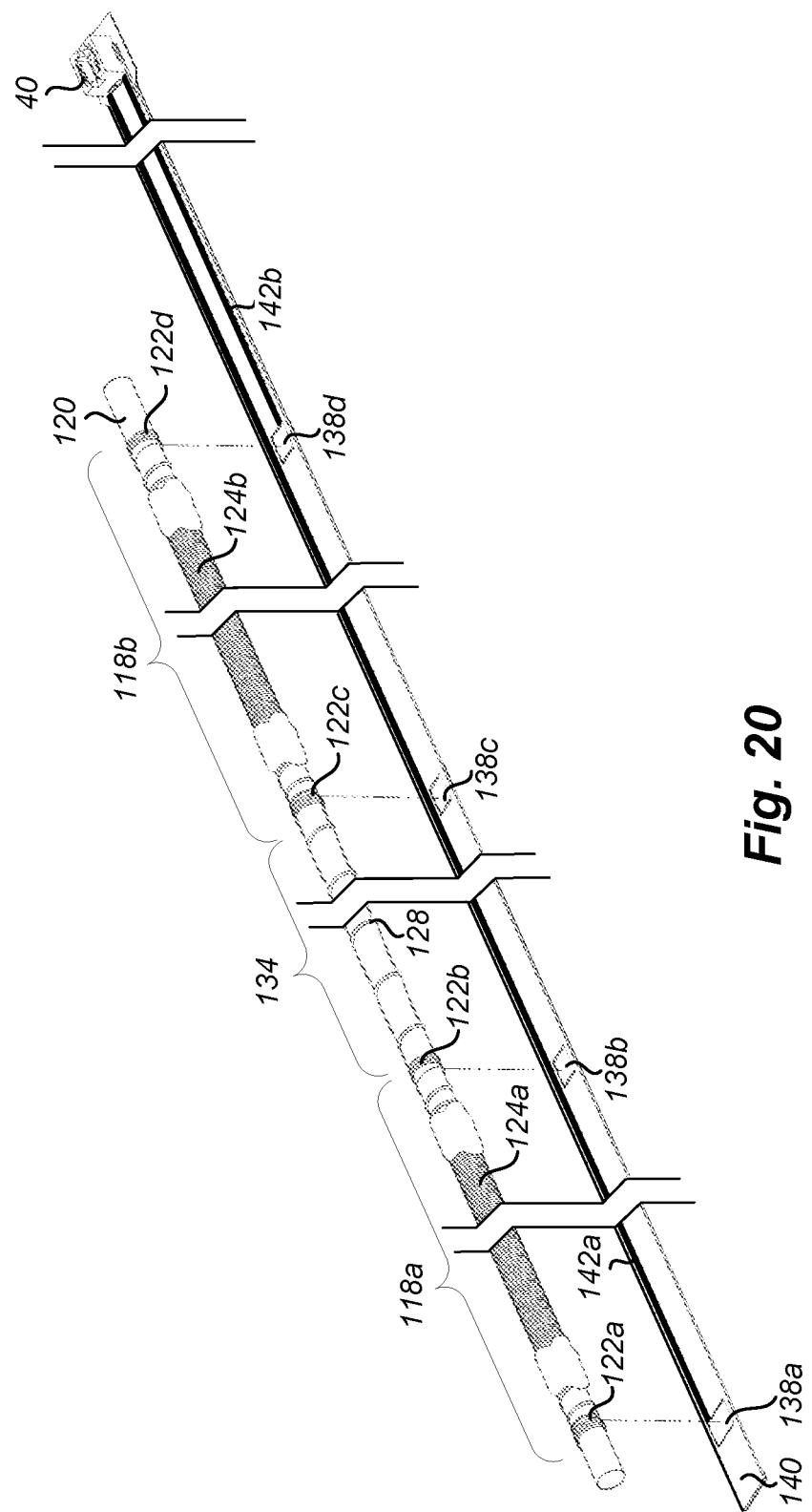
FIG. 20 is an illustration of a flexible printed circuit with multiple electromagnet structures as part of a medical instrument, according to one embodiment.

FIG. 20 is an illustration of a flexible printed circuit 140 with multiple electromagnet structures 118a, 118b as part of a medical instrument 16 (see FIG. 1), according to one embodiment. The flexible printed circuit 140 is an embodiment of the flexible printed circuit 140 described herein in conjunction with FIG. 18. Accordingly, the flexible printed circuit 140 is a flexible substrate that includes patterned contact pads 138a-138d and patterned metal traces 142a, 142b.

In various embodiments, contact pads 138a-138b are solderable pads on which corresponding lead contacts 122a-122d of electromagnet structures 118a, 118b can be coupled. These contact pads 138a-138b affix the electromagnet structures 118a, 118b to the flexible printed circuit 140 and enable an excitation signal to be applied to the electromagnet structures 118a, 118b.

As illustrated and described in more detail herein, the flexible printed circuit 140 includes metal traces 142a, 142b that run substantially along the length of the flexible printed circuit 140 from ancillary circuitry 40 in one portion of the flexible printed circuit 140 to the electromagnet structures 118a, 118b in an opposing, different portion of the flexible printed circuit 140. A first end of each of the metal traces 142a, 142b is electrically coupled to the ancillary circuitry 40, and a second opposing end of each of the metal traces 142a, 142b is electrically coupled to a corresponding contact pad 138 (e.g., metal trace 142a is connected to contact pad 138a and metal trace 142b is connected to different contact pad 138d). Accordingly, the contact pads 138a, 138d are electrically coupled to a corresponding metal trace 142a, 142b, and contact pads 138b, 138c are not electrically coupled to a metal trace.

As described herein, the electromagnet structures 118a, 118b are created by wrapping a wire 128 around a core 120 at different pitches to create a first electromagnet structure 118a with first and second lead contacts 122a, 122b and a conductive coil 124a, and a second electromagnet structure 118b with first and second lead contacts 122c, 122d and a conductive coil 124b, wherein the electromagnet structures 118a, 118b are separated by an electromagnet assembly gap 134. Each lead contact 122a-122d is coupled to a respective contact pad 138a-138d, for example, lead contact 122a is soldered to contact pad 138a, lead contact 122b is soldered to contact pad 138b, lead contact 122c is soldered to contact pad 138c, and lead contact 122d is soldered to contact pad 138d. At least lead contact 122a is electrically coupled to contact pad 138a and lead contact 122d is electrically coupled to contact pad 138d, which electrically couples lead contact 122a to metal trace 142a and electrically couples lead contact 122d to metal trace 142b. Since contact pads 138b, 138c are not electrically coupled to a metal trace 142, the connection between the lead contacts 122b, 122c and the respective contact pads 138b, 138c provide structural support in between the electromagnet structures 118a, 118b and the flexible printed circuit 140.

Similar to what is described herein, ancillary circuitry 40 is electrically coupled to the metal traces 142a, 142b to pass an electrical current (e.g., an excitation signal) through the metal traces 142a, 142b and through the conductive coils 124a, 124b (via lead contacts 122a, 122d) of the electromagnet structures 118a, 118b. In this way, an excitation signal with a particular waveform is utilized to cause the conductive coils 124a, 124b to generate magnetic fields that correspondingly form, grow, and collapse based on the electrical current associated with the excitation signal, similar to what is described herein.

FIGS. 18A-18B, described herein, illustrate multiple electromagnet structures 118 being assembled on a single core 120 using a single wire 128 such that each electromagnet receives the same excitation signal. Embodiments are not so limited, however, and in some embodiments, multiple electromagnet structures may be manufactured to receive separate or distinct excitation signals.

FIGS. 21A-21B also illustrate multiple electromagnet structures 118 being assembled on a single core 120 using a single wire 128, but structured to receive excitation signals distinct from one another. As illustrated in FIG. 21A, first and second electromagnet structures 118a, 118b are created on a core 120 using a wire 128. By employing embodiments described herein with respect to FIG. 19A, a first electromagnet structure 118a is created by wrapping the wire 128 around the core 120 at different pitches to create a first lead contact 122a, a conductive coil 124a, and a second lead contact 122b. For ease of illustration and discussion, the contact/coil gaps 126 between the lead contacts 122 and the conductive coil 124 are not referenced, and the adhesive compound 129a, 129b that mechanically stabilizes the conductive coil 124 on the core 120 is not illustrated or referenced.

After the first electromagnet structure 118a is created, the wire 128 that was used to create the first electromagnet coil structure 118a is looped over an electromagnet assembly gap section 134 of the core 120 to create a wire loop 136. The electromagnet assembly gap 134 creates a buffer or separation between the first electromagnet structure 118a and the second electromagnet structure 118b. And the wire loop 136 provides a structure where the wire 128 can be severed without impacting the core 120 or the first or second electromagnet structures 118a, 118b. Accordingly, the wire 128 is continued without a break or separation along the electromagnet assembly gap 134 between the first and second electromagnet structures 118a, 118b, which can increase the speed and number of electromagnet structures 118 that can be created on a single core 120. In some other embodiments, the wire 128 is severed after creating the first electromagnet structure 118a and prior to creating the second electromagnet structure 118b.

The second electromagnet structure 118b is then created after the wire loop 136 is created, by wrapping the wire 128 around the core 120 in a manner described herein with respect to FIG. 19A. As a result, a second electromagnet structure 118b is created with a first lead contact 122c, a conductive coil 124b, and a second lead contact 122d for the second electromagnet structure 118b. Again, for ease of illustration and discussion, the contact/coil gaps 126 between the lead contacts 122 and the conductive coil 124 are not referenced, and the adhesive compound 129a, 129b that mechanically stabilizes the conductive coil 124 on the core 120 is not illustrated or referenced.

By creating the wire loop 136 between the first and second electromagnet structures 118a, 118b, the wire loop 136 can be severed, which creates two distinct electromagnet structures 118a, 118b that can be provided with separate excitation signals. In some embodiments, only the wire loop 136 is severed and the core 120 is left intact over the electromagnet assembly gap 134. In this way, multiple distinct electromagnet structures 118 can be manufactured on a single core 120 and connected to a single flexible printed circuit, which is further illustrated below in conjunction with FIGS. 22A-22B. The length of the electromagnet assembly gap 134 is dependent on a distance between the first and second electromagnet structures 118a, 118b when attached to the flexible printed circuit 140. In other embodiments, both the wire loop 136 and the core 120 are severed at the electromagnet assembly gap 134. In this way, multiple distinct electromagnet structures 118 can be manufactured on a single core 120 regardless of whether the electromagnet structures 118 will be connected to a same flexible printed circuit or separate flexible printed circuits, which is further illustrated below in conjunction with FIGS. 22C and 22D.

Although FIG. 21A illustrates two electromagnet structures 118a, 118b assembled on a single core 120 with a wire loop 136 between them, embodiments are not so limited, and other pluralities of electromagnet structures 118 may be assembled on a single core 120. For example, FIG. 21B illustrates an assembly with four electromagnet structures 118a-118d on a single core 120, similar to what is described herein in conjunction with FIG. 19B. Again, a single continuous wire 128 is wrapped around the core 120 to create four distinct electromagnet structures 118a-118d that are each separated by a respective electromagnet assembly gap 134a-134c.

Along each electromagnet assembly gap 134a-134c the wire 128 is looped to create wire loops 136a-136c. As a result, a first electromagnet structure 118a includes first and second lead contacts 122a, 122b and conductive coil 124a; a second electromagnet structure 118b includes first and second lead contacts 122c, 122d and conductive coil 124b; a third electromagnet structure 118c includes first and second lead contacts 122e, 122f and conductive coil 124c; and a fourth electromagnet structure 118d includes first and second lead contacts 122g, 122h and conductive coil 124d.

As described herein, the wire loops 136a-136c provide structures for severing the wire 128 (and in some embodiments the core 120) between neighboring electromagnet structures 118a-118d, which allows for each electromagnet structure 118a-118d to be distinct from one another, thus allowing for multiple electromagnet structures 118a-118d to be manufactured on a single core 120. Again, in some embodiments, the electromagnet structures 118a-118d can be separated from one another by severing the core 120 such that the electromagnet structures 118a-118d can be used in separate locations on a single flexible printed circuit 140, or can be used on separate flexible printed circuits. In other embodiments, the core 120 may remain intact between the electromagnet structures 118a-118d such that separate and distinct excitation signals can be provided to the separate electromagnet structures 118a-118d.

As discussed herein, by providing separate or distinct excitation signals to the separate electromagnet structures 118a-118d, the magnetic field generated by electromagnet structures 118a-118d can be different at any given point in time, which allows for the sensor 12 (FIG. 1) to detect the separate magnetic fields. By sensing different magnetic fields, the position, orientation, and movement of various different portions (i.e., where the different electromagnet structures 118a-118d are positioned along the length of the flexible printed circuit) of the medical instrument 16 (FIG. 1) is determined at various depths within the body of the patient.

FIGS. 22A-22B are illustrations of a flexible printed circuit 158 with distinct electromagnet structures 118a, 118b with a same core 120 as part of a medical instrument 16 (see FIG. 1), according to one embodiment. The flexible printed circuit 158 is an embodiment of the flexible printed circuit 140 described herein in conjunction with FIG. 20. Accordingly, the flexible printed circuit 158 is a flexible substrate that includes patterned contact pads 138a-138d and patterned metal traces 142a, 142b. Unlike the flexible printed circuit 140, however, the flexible printed circuit 158 also includes additional patterned metal traces 142c, 142d.

The metal traces 142a-142d run substantially along the length of the flexible printed circuit 158 from ancillary circuitry 40 (not illustrated) in one portion of the flexible printed circuit 158 to the electromagnet structures 118a, 118b in an opposing, different portion of the flexible printed circuit 158. A first end of each of the metal traces 142a-142d is electrically coupled to the ancillary circuitry 40, and a second opposing end of each of the metal traces 142a-142d is electrically coupled to a corresponding contact pad 138. For example, metal trace 142a is electrically connected to contact pad 138c, metal trace 142b is electrically connected to contact pad 138d, metal trace 142c is electrically connected to contact pad 138a, and metal trace 142d is electrically connected to contact pad 138b. Similar to what is described herein, the contact pads 138a-138d are solderable pads on which a corresponding lead contact 122a-122d of electromagnet structures 118a, 118b can be electrically coupled.

In some cases, the flexible printed circuit 158 has a plurality of layers that together form the thickness of the flexible printed circuit 158. In some cases, one or more traces are arranged on a first layer of the flexible printed circuit 158 and one or more different traces are arranged on a second layer. In the illustrated example, the metal traces 142a, 142b are formed in a first layer of the flexible printed circuit 158 and the metal traces 142c, 142d are formed in a second layer of the flexible printed circuit 158, although in other embodiments, the metal traces 142a-142d may be formed in a same layer of the flexible printed circuit 158.

The electromagnet structures 118a, 118b are embodiments of the electromagnet structures 118a, 118b described herein in conjunction with FIG. 21A. In the illustrated example, however, the wire loop 136 (see FIG. 21A) has been severed between the electromagnet structures 118a, 118b without severing the core 120 of the electromagnet assembly gap 134. In this way, the electromagnet structures 118a, 118b are distinct from one another but both utilize the same core 120. The lead contact 122a of electromagnet structure 118a is electrically coupled (e.g., soldered) to contact pad 138a, lead contact 122b of electromagnet structure 118a is electrically coupled (e.g., soldered) to contact pad 138b, lead contact 122c of electromagnet structure 118b is electrically coupled (e.g., soldered) to contact pad 138c, and lead contact 122d of electromagnet structure 118b is electrically coupled (e.g., soldered) to contact pad 138d.

The ancillary circuitry 40 (not illustrated) is electrically coupled to the metal traces 142a-142d to pass an electrical current (e.g., an excitation signal) through the metal traces 142a-142d and through the conductive coils 124a, 124b of the electromagnet structures 118a, 118b. In a manner similar to what is described herein in conjunction with FIG. 9, each electromagnet structure 118a, 118b is individually controlled. The ancillary circuitry 40, or control circuit 14 (FIG. 1), includes various circuit components to control the separate flow of electrical current to each electromagnet structure 118a, 118b. The separate control of electrical current allows for separate and distinct excitation signals to be sent to each electromagnet structure 118a, 118b via their corresponding metal traces 142a, 142b and 142c, 142d, respectively. As described elsewhere herein, providing separate or distinct excitation signals to the separate electromagnet structures 118a, 118b causes the electromagnet structures 118a, 118b to generate different magnetic fields at any given point in time, which allows for the separate magnetic fields to be detected, and the position, orientation, and movement of various different portions of the medial instrument to be determined.

Moreover, although FIGS. 22A-22B illustrate two electromagnet structures, embodiments are not so limited, and in other embodiments, three or more electromagnet structures may be utilized along the length of the flexible printed circuit.

FIGS. 22C and 22D are illustrations of a flexible printed circuit 158 with distinct electromagnet structures 118a, 118b with separate cores 120a, 120b as part of a medical instrument 16 (see FIG. 1), according to one embodiment. The flexible printed circuit 158 is an embodiment of the flexible printed circuit 158 described herein in conjunction with FIGS. 22A-22B. Accordingly, the flexible printed circuit 158 includes patterned metal traces 142a, 142b on a first layer of the flexible printed circuit 158 to provide an excitation signal to the electromagnet structure 118a, and separate patterned metal traces 142c, 142d on a second layer of the flexible printed circuit 158 to provide an excitation signal to the electromagnet structure 118b. Moreover, the metal traces 142a-142d are electrically coupled to contact pads 138a-138d.

The electromagnet structures 118a, 118b are embodiments of the electromagnet structure 118 described herein in conjunction with FIG. 17A. Each electromagnet structure 118a, 118b may be manufactured on separate cores 120a, 120b as described herein in conjunction with FIG. 1, or they may be manufactured on a single core 120 as described herein in conjunction with FIG. 21A but with the wire 128 and the core 120 being severed at the electromagnet assembly gap 134. Similar to what is described herein in conjunction with FIGS. 22A-22B, the lead contact 122a of electromagnet structure 118a is electrically coupled (e.g., soldered) to contact pad 138a, lead contact 122b of electromagnet structure 118a is electrically coupled (e.g., soldered) to contact pad 138b, lead contact 122c of electromagnet structure 118b is electrically coupled (e.g., soldered) to contact pad 138c, and lead contact 122d of electromagnet structure 118b is electrically coupled (e.g., soldered) to contact pad 138d.

The ancillary circuitry 40 (not illustrated) is electrically coupled to the metal traces 142a-142d to pass an electrical current (e.g., an excitation signal) through the metal traces 142a-142d and through the conductive coils 124a, 124b of the electromagnet structures 118a, 118b. In a manner similar to what is described herein in conjunction with FIGS. 22A-22B, each electromagnet structure 118a, 118b is individually controlled, such that separate and distinct excitation signals are sent to each electromagnet structure 118a, 118b via their corresponding metal traces 142a, 142b and 142c, 142d, respectively.

Various embodiments described in conjunction with FIGS. 17A, 17B, 18, 19A, 19B, 20, 21A-21B, and 22A-22D may be combined with other embodiments described elsewhere herein. For example, the assembly of the flexible printed circuit 140 and electromagnet structure 118 described in conjunction with FIG. 18 may be utilized in a multi-lumen catheter as described in conjunction with FIGS. 5A-5B. As another example, the assembly of the flexible printed circuit 158 and electromagnet structures 118a, 118b described in conjunction with FIG. 20 may be utilized within a tube-like structure described in conjunction with FIG. 4. These examples are merely for illustration purposes, and other combinations of embodiments described are envisaged.

Figure 23:
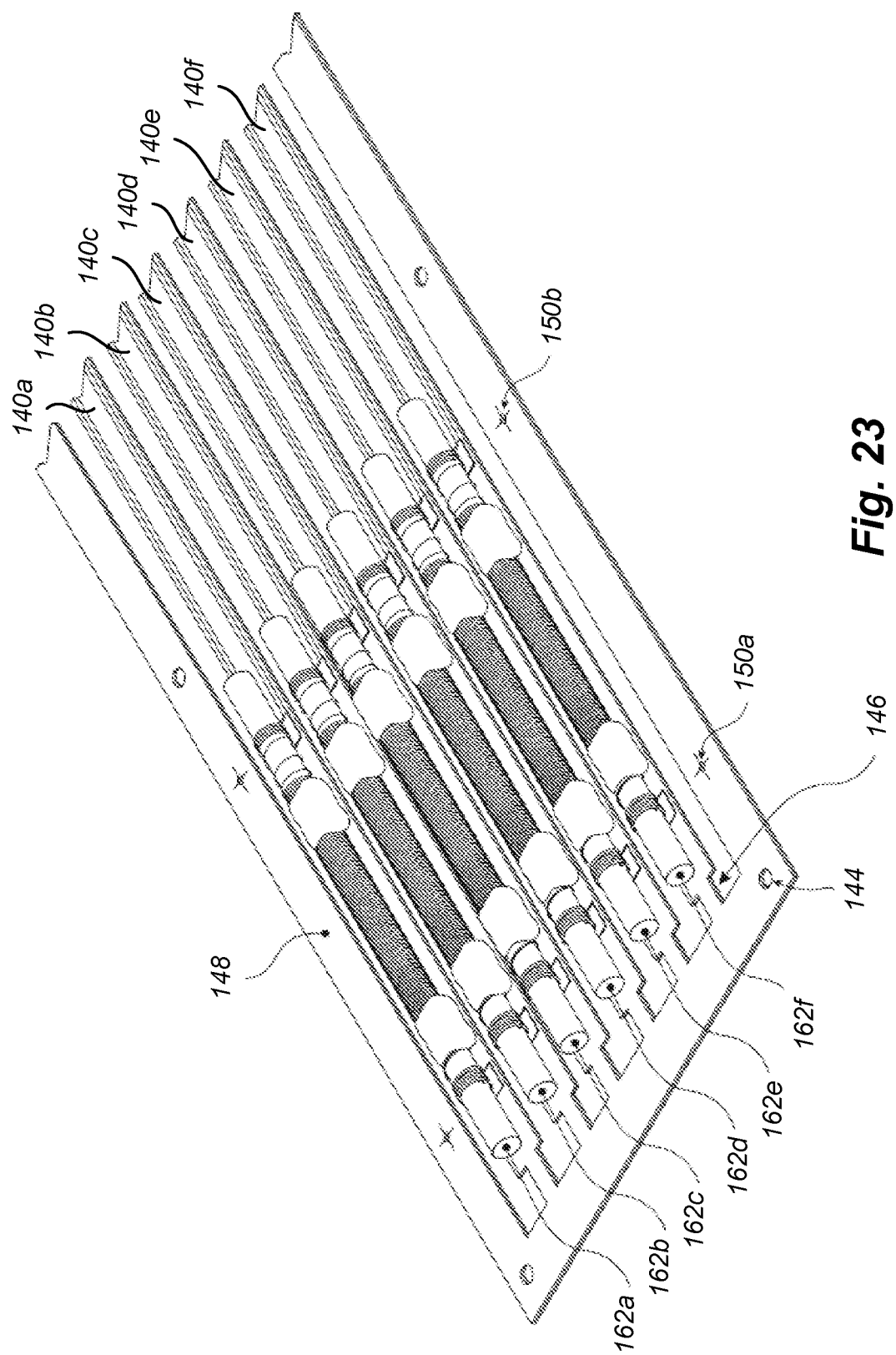
FIG. 23 is an illustration of a plurality of flexible printed circuits with electromagnet structure assemblies, according to one embodiment.

FIG. 23 is an illustration of a plurality of flexible printed circuits 140a-140f with electromagnet structure assemblies 162a-162f, according to one embodiment. Flexible printed circuits 140a-140f are embodiments of flexible printed circuit 140, and electromagnet structure assemblies 162a-162f are embodiments of electromagnet structure 118 described herein.

As illustrated, multiple flexible printed circuits 140a-140f are formed in a panelized configuration, i.e., assembly panel 148, for automated assembly. Each of the plurality of flexible printed circuits 140a-140f is formed independent of one another, but with a corresponding tab 146 to keep the position of each respective flexible printed circuit 140a-140f consistent in the assembly panel 148. In various embodiments, the flexible printed circuits 140a-140f are pre-formed prior to connecting corresponding electromagnet structures and ancillary circuitry to each flexible printed circuit.

The plurality of flexible printed circuits 140a-140f is formed such that each respective flexible printed circuit has patterned therein a first metal trace and a second metal trace running linearly along a substantial length of a flexible substrate to form the respective flexible printed circuit, each of the first and second metal traces having a first end electrically coupled to a respective contact pad and a second end electrically coupled to ancillary circuitry, as described herein. In various embodiments, the plurality of flexible printed circuits 140a-140f are formed such that their orientation is substantially similar in the assembly panel 148, as shown, or alternating orientations, similar to what is shown in FIG. 15A. The electromagnet structure assemblies 162a-162f are positioned relative to the flexible printed circuits 140a-140f, as described elsewhere herein.

The assembly panel 148 may also include other features or structures that are utilized in the manufacture of the assembly panel 148. For example the assembly panel 148 may include one or more mounting apertures 144 that are used to mount the assembly panel 148 to a solder/welder fixture or machine. The assembly panel 148 may also include one or more registration fiducials 150a, 150b for machine vision registration of the assembly panel 148. These and other components can be utilized to improve the accuracy of making the assembly panel 148 or positioning the electromagnet structure assemblies 162a-162f on the corresponding flexible printed circuits 140a-140f.

FIGS. 24A-24D are illustrations of assembly of a plurality of flexible printed circuits 140a-140e with electromagnet structure assemblies 162a-162e, according to one embodiment. These figures illustrate an exemplary hot bar process for coupling the lead contacts 160a-160j of the electromagnet structures 162a-162e to corresponding contact pads 166a-166j of the flexible printed circuits 140a-140e.

The flexible printed circuits 140a-140e are embodiments of flexible printed circuit 140 described herein in conjunction with FIG. 18. Accordingly, the flexible printed circuits 140a-140e include first contact pads 166a-166e, which are embodiments of contact pad 138a described herein, and second contact pads 166f-166j, which are embodiments of contact pad 138b described herein. The electromagnet structure assemblies 162a-162e are embodiments of electromagnet structure 118 described herein in conjunction with FIG. 18. Accordingly, the electromagnet structure assemblies 162a-162e include first lead contacts 160a-160e, which are embodiments of lead contact 122a described herein, and second lead contacts 160f-160j, which are embodiments of lead contact 122b described herein.

As illustrated in FIG. 24A, the flexible printed circuits 140a-140e and the electromagnet structure assemblies 162a-162e are manufactured and positioned as described herein such that the first lead contacts 160a-160e of the electromagnet structures 162a-162e align with first contact pads 166a-166e of the flexible printed circuits 140a-140e, respectively, and the second lead contacts 160f-160j of the electromagnet structures 162a-162e align with second contact pads 166f-166j of the flexible printed circuits 140a-140e, respectively.

Solder and flux is added to each contact pad 166a-166j of each flexible printed circuit 140a-140e such that the solder and flux is disposed between each contact pad 166a-166j and each respective lead contact 160a-160j of the electromagnet structures 162a-162e. FIG. 24B is an enlarged image of a portion of FIG. 24A, and it illustrates solder and flux 152 disposed between the first contact pad 166e of the flexible printed circuit 140e and the first contact 160e of the electromagnet assembly 162e. Solder and flux is similarly added between each other respective lead contact 160a-160j and contact pad 166a-166j.

A solder-bar head 154 is positioned over the first lead contacts 160a-160e of the electromagnet structures 162a-162e, as shown in FIG. 24A. The solder-bar head 154 includes a solder-bar tip 156, which, when pressed against the first lead contacts 160a-160e, applies heat and pressure to the first lead contacts 160a-160e, resulting in the soldering of the first lead contacts 160a-160e to the corresponding first contact pads 166a-166e. As described herein, in some embodiments, the wire (e.g., wire 128) that makes up the lead contacts and the core (e.g., core 120) are coated with an electrically insulating material. In at least one embodiment, the insulating material on the wire has a lower melting point than the insulating material on the core. When heat is applied to the lead contacts, the insulating material around the wire of the lead contacts melts to allow the lead contacts to be soldered and electrically coupled to the corresponding contact pads, without damaging the core or other portions of the electromagnet structures.

Figure 24C:
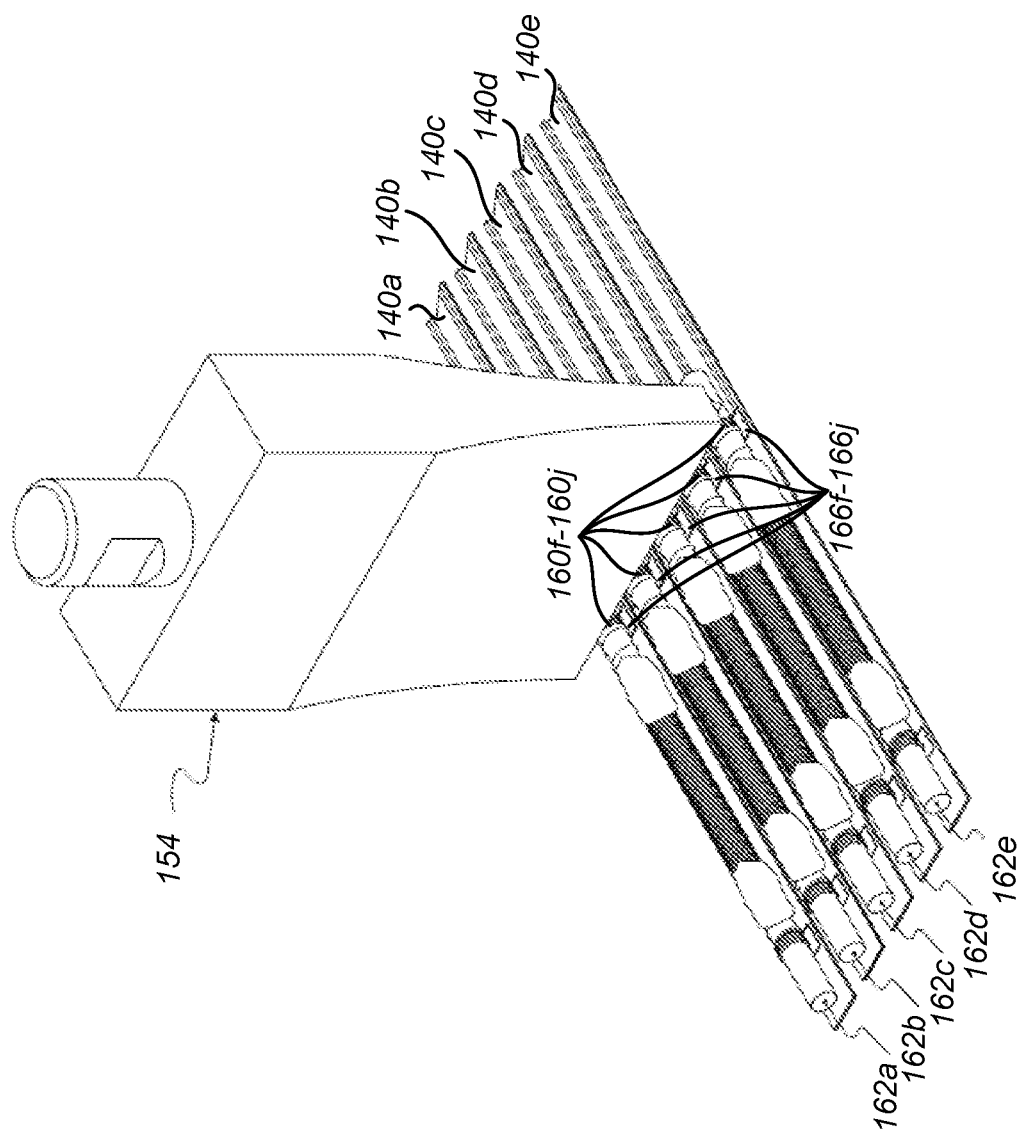

Once the first lead contacts 160a-160e are soldered to the first contact pads 166a-166e, the solder-bar head 154 is repositioned over the second lead contacts 160f-160j of the electromagnet structures 162a-162e, as shown in FIG. 24C. The solder-bar tip 156 is then pressed against the second lead contacts 160*f*-160*j* to apply heat and pressure to the second lead contacts 160*f*-160*j*, resulting in the soldering of the second lead contacts 160*f*-160*j* to the corresponding second contact pads 166*f*-166*j*.

Figure 24D:
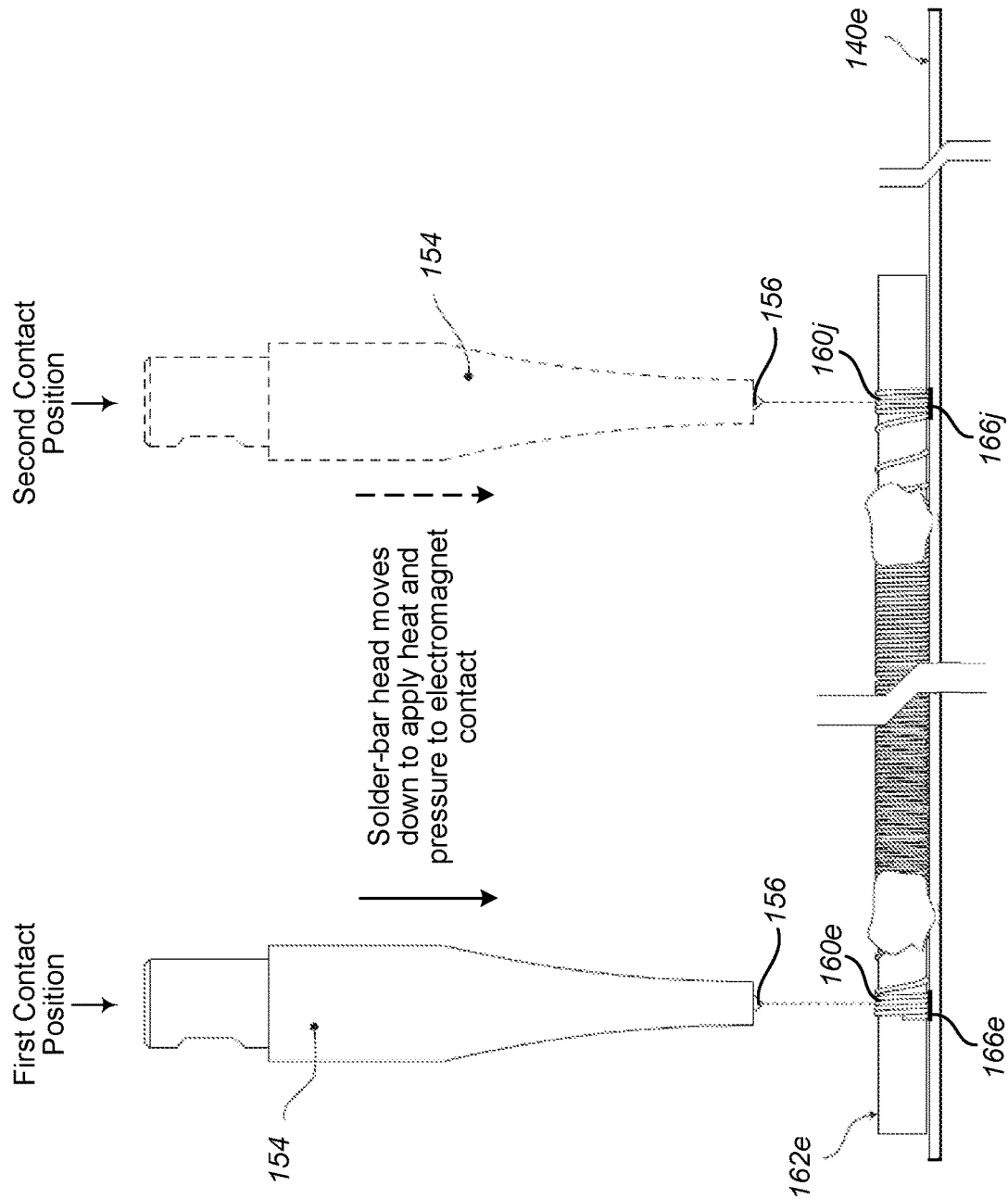

FIG. 24D shows a side view of the positioning and soldering of electromagnet structure 162*e* to flexible printed circuit 140*e*. As described herein, the solder-bar head 154 is positioned with the solder-bar tip 156 above the first lead contact 160*e* of the electromagnet structure 162*e*, and the solder-bar head 154 is moved down so that the solder-bar tip 156 contacts and applies heat and pressure to the first lead contact 160*e*, which results in the soldering of the first lead contact 160*e* of the electromagnet structure 162*e* to the first contact pad 166*e* of the flexible printed circuit 140*e*. The solder-bar head 154 is then repositioned above the second lead contact 160*j* of the electromagnet structure 162*e*. The solder-bar head 154 is moved down so that the solder-bar tip 156 contacts and applies heat and pressure to the second lead contact 160*j*, which results in the soldering of the second lead contact 160*j* of the electromagnet structure 162*e* to the second contact pad 166*e* of the flexible printed circuit 140*e*.

The assembly process described herein allows for the coupling of multiple electromagnet structures and corresponding flexible printed circuits at a single time. This process may be utilized to couple other embodiments of the electromagnet structure and flexible printed circuit as described herein.

Moreover, the hot bar process described herein is not limiting, and other soldering and electrical coupling techniques may be employed to couple the electromagnet structures and flexible printed circuits described herein.

FIGS. 25A-25D are illustrations of an electromagnet superstructure 218 embodiment formed in a primary manufacturing process, which can be arranged into a one or more electromagnet structure 218*a* embodiments according to a secondary manufacturing process. The electromagnet superstructure 218 (FIG. 25A) can be formed as a single electromagnet structure 218*a* (FIG. 25C) in some embodiments, or the electromagnet superstructure 218 can be formed into two or more electromagnet structures in other embodiments.

Figure 25A:
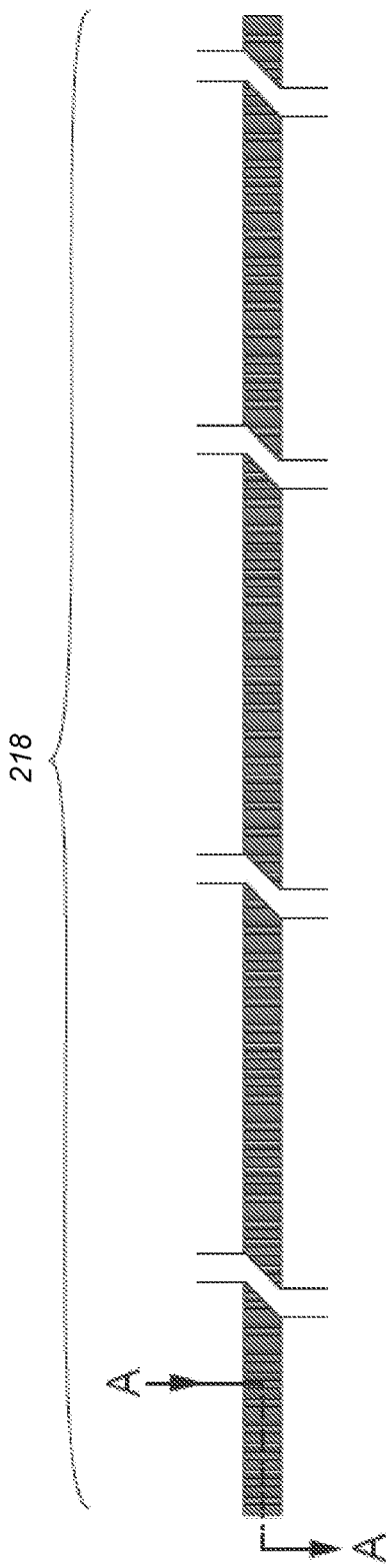
FIGS. 25A-25D are illustrations of an electromagnet superstructure embodiment formed in a primary manufacturing process, which can be arranged into a one or more electromagnet structure embodiments according to a secondary manufacturing process.
Figure 25B:
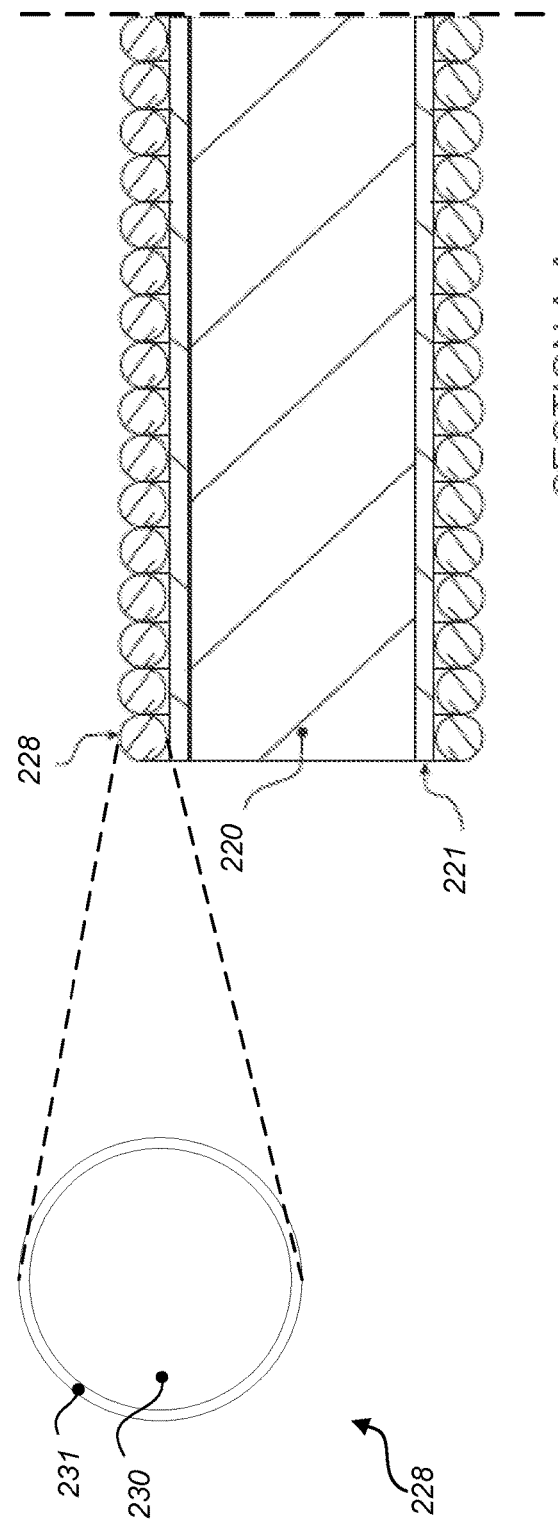

FIG. 25B is a portion of the electromagnet superstructure 218 embodiment of FIG. 25A as viewed in cross section at "A." In a first act of the primary manufacturing process, a coil (228) is wound along an entire length of a core 220, a substantial length of the core 220, or for some other determined portion of a core 220 (FIG. 25B). The core 220 may be a core along the lines of core 32 and core 120, and the coil 228 may be formed from a material and along the lines of conductive coil 34 and wire 128, all of which are described in the present disclosure and not repeated herein for brevity. Core 220 and coil 228 may additionally or alternatively have other characteristics, which are further described herein.

In some cases, the core 220 is a wire or wire-like structure. The core 220 may have any desirable diameter or dimension that corresponds to the diameter if the core 220 is not a "wire." For example, in some cases, the "diameter" of core 220 is between about 0.0005 inches and 0.250 inches. In some cases, the "diameter" of core 220 is between about 0.00025 inches and 0.05 inches. Other "diameters" are also contemplated. In at least one embodiments, the core 220 diameter is about 0.010 inches.

In some cases, core 220 is a determined length. In other cases, core 220 is an indeterminate length. For example, prior to formation of the electromagnet superstructure 218 in the first act of the primary manufacturing process, core 220 may be arranged on a spool or other means. The spool or other mechanism permits a dynamic formation of the electromagnet superstructure 218 by continuously winding conductive coil 228 around a core 220. Hence, the core 220, and the electromagnet superstructure 218, may have a length equal or about equal to the length of core 220 that is arranged on a spool or other means before the first act of the primary manufacturing process. In various embodiments, core 220 is five feet, 25 feet, 100 feet, 250 feet, 1000 feet, or any other desirable length.

The core 220 may be a ferrous material such as steel. The core 220 is coated, encased, enclosed, covered, confined, jacketed, or otherwise surrounded by an insulating material 221. The insulating material 221 of the core 220 will have electrically insulating properties. The insulating material 221 of the core 220 may also have desirable mechanical properties that permit the core 220 to be twisted, bent, heated, severed, or otherwise manipulated without undesirably compromising the electrically insulating properties. In some embodiments, due to these properties, in whole or in part, the electromagnet superstructure 218 or any single electromagnet structure 218*a* may be manipulated without electrically shorting the core 220 to the coil 228. In other embodiments, a selected portion of the coil 228 may be electrically shorted to the core 220 for a particular purpose such as to use the core 220 as an electrical conductor to pass a control signal to the coil 228.

In some embodiments, the insulating material 221 of the core 220 comprises a polymer, an oxide, or some other material having a transition temperature (e.g., melting point, evaporative point, decimation point, or the like) at a first temperature. The first temperature may be in excess of 212 degrees Fahrenheit (° F.), 350° F., 450° F., 550° F., or some other temperature. By heating the core 220 to a selected temperature that exceeds the first temperature, the insulating material 221 of core 220 may be breached, thereby exposing the conductive material of core 220.

Similar to the core 220, the coil 228 may be formed from a wire or the coil 228 may be otherwise structured in wire-like manner. That is, the coil 228 may have a cross-sectional shape that is circular, elliptical, square, rectangular, or any other shape. Considering that the coil 228 may be a wire or wire-like structure, the coil 228 may have any desirable diameter or dimension that corresponds to the diameter if the coil 228 is not a "wire." For example, in some cases, the "diameter" of coil 228 is between about 0.0005 inches or less. Other diameters are contemplated, for example, the coil 228 diameter may be between substantially about 0.00025 inches and 0.05 inches or some other range. In at least one embodiment, the coil 228 diameter is about 0.001 inches.

The coil 228 may be a determined length or an indeterminate length. In some cases, before the electromagnet superstructure 218 is formed in the first act of the primary manufacturing process, coil 228 may be arranged on a spool or some other means. The spool or other mechanism permits a dynamic formation of the electromagnet superstructure 218 by continuously winding coil 228 around a core 220. Embodiments may permit the wire or wire-like structure of coil 228 to begin the primary manufacturing process on a spool and with a length of five feet, 25 feet, 100 feet, 250 feet, 1000 feet, or any other desirable length.

Like the core 220, the coil 228 includes an electrically conductive portion 230 that is coated, encased, enclosed, covered, confined, jacketed, or otherwise surrounded by an insulating material 231. The insulating material 231 of the coil 228 will have electrically insulating properties. The insulating material 231 of the coil 228 may also have desirable mechanical properties that permit the coil 228 to be twisted, bent, heated, severed, or otherwise manipulated without undesirably compromising the electrically insulating properties. In some embodiments, due to these properties, in whole or in part, the electromagnet superstructure 218 or any single electromagnet structure 218a may be manipulated without electrically shorting the coil 228 to the core 220. In other embodiments, a selected portion of the coil 228 may be electrically shorted to the core 220.

In some embodiments, the insulating material 231 of the coil 228 comprises a polymer, an oxide, or some other material having a transition temperature at a second temperature that is lower than the first temperature (i.e., the transition temperature of the insulating material 221 of core 220). The second temperature may be less than 550 degrees Fahrenheit (° F.), 450° F., 350° F., 212° F., or some other temperature. By heating the coil 228 to a selected temperature that exceeds the second temperature, the insulating material 231 of coil 228 may be breached, thereby exposing the electrically conductive material 230 of coil 228.

In some cases, the electromagnet superstructure 218 may be heated to a temperature that is below the first temperature and above the second temperature. In this way, the transition temperature of the coil 228 insulating material 231 may be crossed, which exposes the electrically conductive portion 230 of coil 228, but transition temperature of the core 220 insulating material 221 is not crossed, which maintains the insulated integrity of the core 220 from the coil 228.

Figure 25C:
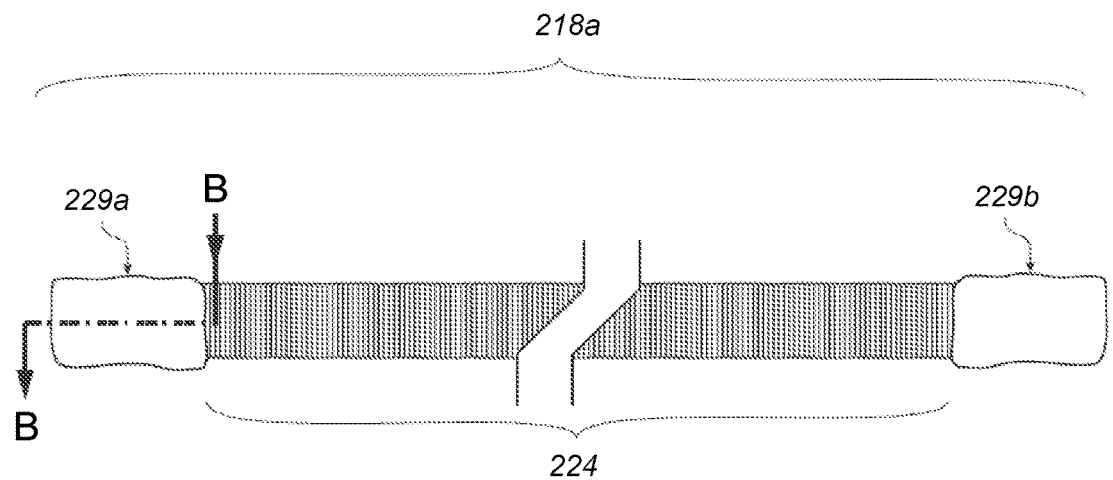

FIG. 25C is a single electromagnet structure 218a, which has been cut, severed, pinched, or otherwise formed from the electromagnet superstructure 218. The single electromagnet structure 218a includes "tinned" ends 229a, 229b and an "active" coil section 224. The active coil section may be operated as an electromagnet as described in the present disclosure, but not repeated here so as to not cloud the description of the embodiments depicted in FIGS. 25A-25D.

Figure 25D:
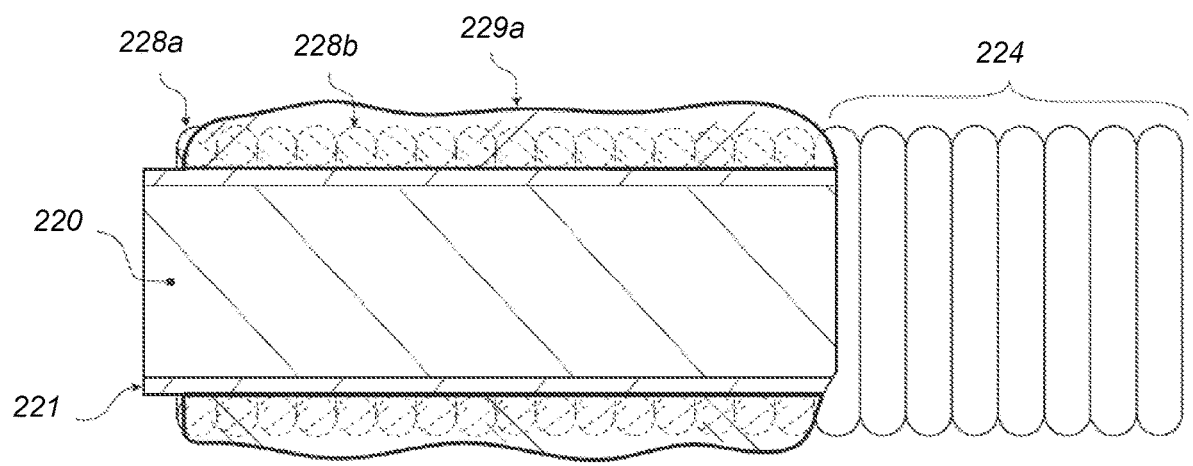

FIG. 25D is a detailed view of the portion of FIG. 25C at section B-B. In FIG. 25D, the core 220, core insulating material 221 and a portion of the active coil section 224 are identified. A portion of section B-B in FIG. 25D corresponds to the subject matter of FIG. 25B. That is, part of the single electromagnet structure 218a is shown in a cross-sectional view.

In the cross-sectional view portion of FIG. 25D, various turns of coil 228 are shown encased in solder, which forms the tinned end 229a of the single electromagnet structure 218a. For clarity a first coil 228a turn is partially encased in solder, and a second coil 228b turn is fully encased in solder. The tinned ends 229a, 229b are formed in a secondary manufacturing process of the single electromagnet structure 218a. In this secondary process, the coil windings under the solder patch become shorted together, which creates a fully- or quasi-electrical contact with one end of the coil 228. In some embodiments, this solder section is electrically isolated from the core 220 by the insulation material 221 of the core 220.

As part of the secondary manufacturing process, or in a different process, the single electromagnet structure 218a may be electrically coupled to a flexible printed circuit as described in the present disclosure, and not now repeated for brevity.

As described in the manufacturing processes of FIGS. 25A-25D, an electromagnet superstructure 218 embodiment can be formed from core 220 material and coil 228 material. The core 220 material and the coil 228 material may be continuously drawn from spools or some other delivery means. If the electromagnet superstructure 218 embodiment is "long," (i.e., a length longer than the length of a desired single electromagnetic structure) it can be used to form two or more single electromagnet structures 218a, which are separated (e.g., cut, pinched, severed, or the like) from the electromagnet superstructure 218 in any way. The coil 228, which includes insulating material 231, is wound over a core 220, which includes insulating material 221. The insulating material 221 of core 220 has transition temperature that is higher than the transition temperature of the coil 228 by a desired amount (e.g., 100° F., 175° F., 250° F., or more). This arrangement of structures having the characteristics described herein allows coil 228 material to be wound continuously on core 220 material and then cut to a desired length. The resulting structure has ends that are solder tinned without creating an electrical short to the core 220. The finished single electromagnet structure 218a can then be placed on a flexible circuit and solder reflowed, hot-bar soldered, or otherwise electrically coupled to the flexible circuit. In at least one embodiment, the single electromagnet structure 218a is formed having a core 220 with a diameter of about 0.010 inches, and a coil 228 with a diameter of about 0.001 inches. The number of coils per unit measure (e.g., the number of coils per inch) is about 1000 in this embodiment, and the coil 228 is wrapped over about two inches of the core 220. The single electromagnet structure length in this embodiment is about three inches.

Certain words and phrases used in the specification are set forth as follows. The terms "include" and "comprise," as well as derivatives thereof, mean inclusion without limitation. The term "or," is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation; such a device may be implemented in hardware, firmware, or software, or some combination of at least two of the same. The functionality associated with any particular controller may be centralized or distributed, whether locally or remotely. Other definitions of certain words and phrases may be provided within this patent document. Those of ordinary skill in the art will understand that in many, if not most instances, such definitions apply to prior as well as future uses of such defined words and phrases.

A processor (i.e., a processing unit), as used in the present disclosure, refers to one or more processing units individually, shared, or in a group, having one or more processing cores (e.g., execution units), including central processing units (CPUs), digital signal processors (DSPs), microprocessors, micro controllers, state machines, and the like that execute instructions. In the present disclosure, memory may be used in one configuration or another. The memory may be configured to store data. In the alternative or in addition, the memory may be a non-transitory computer readable medium (CRM) wherein the CRM is configured to store instructions executable by a processor. The instructions may be stored individually or as groups of instructions in files.

The files may include functions, services, libraries, and the like. The files may include one or more computer programs or may be part of a larger computer program. Alternatively, or in addition, each file may include data or other computational support material useful to carry out the computing functions of the systems, methods, and apparatus described in the present disclosure. Some or all of the stored contents of a memory may include software instructions executable by a processing device to carry out one or more particular acts.

The terms "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds or milliseconds), and that the activity may be performed on an ongoing basis. An example of an activity that is not real-time is one that occurs over an extended period of time (e.g., hours or days) or that occurs based on intervention or direction by a person or other activity, such as each magnetic sense measurement occurring at the press of a button.

Unless the context requires otherwise, throughout the specification and claims which follow, the word "comprise" and variations thereof, such as "comprises" and "comprising," are to be construed in an open, inclusive sense, e.g., "including, but not limited to."

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. As used in this specification and the appended claims, the singular forms "a," "an," and "the" include plural referents unless the content and context clearly dictates otherwise. It should also be noted that the conjunctive terms, "and" and "or" are generally employed in the broadest sense to include "and/or" unless the content and context clearly dictates inclusivity or exclusivity as the case may be. In addition, the composition of "and" and "or" when recited herein as "and/or" is intended to encompass an embodiment that includes all of the associated items or ideas and one or more other alternative embodiments that include fewer than all of the associated items or ideas.

The headings and Abstract of the Disclosure provided herein are for convenience only and do not limit or interpret the scope or meaning of the embodiments.

The various embodiments described herein can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
a medical instrument having a first portion and a second portion with the first portion configured for insertion into a body of a patient, the medical instrument including:
a flexible printed circuit having a length and a width, wherein the length is at least twenty times the width, the flexible printed circuit including:
a first metal trace running substantially along the length of the flexible printed circuit, the first metal trace having a first end in the first portion of the medical instrument and a second end in the second portion of the medical instrument; and
a second metal trace running substantially along the length of the flexible printed circuit, the second metal trace having a first end in the first portion of the medical instrument and a second end in the second portion of the medical instrument;
an electromagnet structure in the first portion of the medical instrument, the electromagnet structure including:
a core; and
a conductive coil wound around the core with a first end of the conductive coil electrically coupled to the first end of the first metal trace and a second end of the conductive coil electrically coupled to the first end of the second metal trace; and
ancillary circuitry arranged in the second portion of the medical instrument and electrically coupled to the second end of the first metal trace and to the second end of the second metal trace, the ancillary circuitry configured to drive an excitation signal through the conductive coil via the first and second metal traces to generate a magnetic field about the electromagnet structure.

2. The system of claim 1, further comprising:
a sensor configured to sense the magnetic field created when the excitation signal is driven through the conductive coil and further configured to output a sensor signal representative of at least one portion of the sensed magnetic field; and
a control circuit configured to calculate a position corresponding to the first portion of the medical instrument within the body of the patient based on the sensor signal.

3. The system of claim 1, wherein the first portion of the medical instrument further includes:
a containment structure that contains the electromagnet structure and a first portion of the flexible printed circuit.

4. The system of claim 3, wherein the containment structure is arranged as a multi-lumen catheter having at least two cavities that extend along a length of the multi-lumen catheter, wherein the electromagnet structure and the first portion of the flexible printed circuit are positioned in one of the two cavities of the multi-lumen catheter.

5. The system of claim 1, wherein the medical instrument further includes:
a stiffness member that extends linearly along the length of the flexible printed circuit.

6. The system of claim 5, wherein the stiffness member extends linearly along only a portion of the length of the flexible printed circuit.

7. The system of claim 5, wherein the stiffness member is arranged as an electrode that is electrically coupled to additional ancillary circuitry, the additional ancillary circuitry and the electrode arranged to capture one or more electrical measurements within the body of the patient.

8. The system of claim 5, wherein the medical instrument further includes:
a multi-lumen catheter that contains the first portion of the medical instrument in a first lumen, the first lumen extending along a length of the multi-lumen catheter.

9. The system of claim 1, wherein the medical instrument further includes:
a stiffness member coupled to the flexible printed circuit; and
a tube-like structure that contains the electromagnet structure, a first portion of the flexible printed circuit, and at least a portion of the stiffness member.

10. The system of claim 1, wherein the core has a length that extends linearly along the length of the flexible printed circuit, wherein the conductive coil is wound around a first portion of the length of the core, and wherein a second portion of the length of the core is affixed to the flexible printed circuit.

11. The system of claim 1, wherein the medical instrument further includes:
third and fourth metal traces running along the length of the flexible printed circuit wherein the third and fourth metal traces each have a first end in the first portion of the medical instrument and a second end in the second portion of the medical instrument;
a second electromagnet structure in the first portion of the medical instrument, the second electromagnet structure including:
a second core; and
a second conductive coil wound around the second core with a first end of the second conductive coil electrically coupled to the first end of the third metal trace and a second end of the second conductive coil electrically coupled to the first end of the fourth metal trace; and
second ancillary circuitry arranged in the second portion of the medical instrument and electrically coupled to the second end of the third metal trace and to the second end of the fourth metal trace, the second ancillary circuitry configured to drive a second excitation signal through the second conductive coil via the third and fourth metal traces.

12. The system of claim 11, wherein the core and the second core share a single core structure.

13. The system of claim 1, wherein the flexible printed circuit further includes:
a substantially flat first surface and a substantially flat opposing second surface that both run along the length of the flexible printed circuit;
wherein the first and second metal traces run along the length of the flexible printed circuit on the first surface; and
an electrode pattern runs along the length of the flexible printed circuit on the second surface.

14. The system of claim 1, wherein the flexible printed circuit further includes:
a plurality of layers, wherein the first and second metal traces run substantially along the length of the flexible printed circuit on a first layer of the plurality of layers;
a first electrode pattern runs substantially along the length of the flexible printed circuit on a second layer of the plurality of layers; and
a second electrode pattern runs substantially along the length of the flexible printed circuit on a third layer of the plurality of layers.

15. The system of claim 1, wherein the second portion of the medical instrument further includes:
a housing that contains the ancillary circuitry.

16. The system of claim 15, wherein the housing contains at least one battery arranged to supply power to the ancillary circuitry to drive the excitation signal to the conductive coil.

17. A method to make a medical device, comprising:
creating an electromagnet structure by winding a wire-like conductor into a coil around a core, the wire-like conductor having two opposing ends, wherein a first of the two opposing ends is arranged as a first lead of the coil and a second of the two opposing ends is arranged as a second lead of the coil;
providing a flexible printed circuit structure having patterned therein a first metal trace and a second metal trace running linearly along a substantial length of a flexible substrate to form the flexible printed circuit structure, each of the first and second metal traces having a first end and a second end;
electrically connecting the first lead of the coil to the first end of the first metal trace;
electrically connecting the second lead of the coil to the first end of the second metal trace; and
electrically connecting ancillary circuitry to the second end of the first metal trace and to the second end of the second metal trace, the ancillary circuitry positioned on the flexible printed circuit structure at an opposite end from the electromagnet structure.

18. The method of claim 17, further comprising:
creating a second electromagnet structure by winding a second wire-like conductor into a second coil around a second core, the second wire-like conductor having two opposing ends, wherein a first of the two opposing ends is arranged as a first lead of the second coil and a second of the two opposing ends is arranged as a second lead of the second coil;
providing the flexible printed circuit structure having patterned therein a third metal trace and a fourth metal trace running linearly along the substantial length of the flexible printed circuit structure, each of the third and fourth metal traces having a first end and a second end;
electrically connecting the first lead of the second coil to the first end of the third metal trace;
electrically connecting the second lead of the second coil to the first end of the fourth metal trace; and
electrically connecting the ancillary circuitry to the second end of the third metal trace and to the second end of the fourth metal trace.

19. The method of claim 17, further comprising:
containing at least a first portion of the flexible printed circuit structure and the electromagnet structure within a tube-like structure.

20. The method of claim 17, further comprising:
containing at least a first portion of the flexible printed circuit structure and the electromagnet structure within a cavity of a multi-lumen catheter.

21. The method of claim 17, further comprising:
integrating an electrode in the medical device substantially along the substantial length of the flexible printed circuit structure.

22. A method of operating a medical device, comprising:
passing a first portion of the medical device into a body of a patient while a second portion of the medical device remains outside the body of the patient;
operating ancillary circuitry arranged at the second portion of the medical device to drive an excitation signal through a conductive coil of an electromagnet structure arranged at the first portion of the medical device, the excitation signal passed via first and second traces running substantially along a length of a flexible printed circuit, wherein the electromagnet structure includes a core and the conductive coil wound around the core, and wherein a first end of the conductive coil is electrically connected to a first end of the first trace and a second end of the conductive coil is electrically connected to a first end of the second trace; and sensing a magnetic field generated about the electromagnet structure by the excitation signal being driven through the conductive coil.

23. The method of claim 22, further comprising;

based at least in part on the sensed magnetic field, generating a representation of the first portion of the medical device in the body of the patient; and outputting the representation of the first portion of the medical device in the body of the patient to a presentation system.

24. The method of claim 23, further comprising;

advancing the first portion of the medical device further into the body of the patient; and tracking the first portion of the medical device as it advances into the body of the patient.

25. A method to make a plurality of medical devices, comprising:

forming a plurality of electromagnet structures by winding a wire-like conductor into a respective coil around each respective core of a plurality of cores, the wire-like conductor of each respective coil having two opposing ends, wherein a first of the two opposing ends is arranged as a first lead of the respective coil and a second of the two opposing ends is arranged as a second lead of the respective coil;

arranging the plurality of electromagnet structures on an assembly tray;

forming an assembly panel of a plurality of flexible printed circuit structures, each respective flexible printed circuit structure of the plurality of flexible printed circuit structures having patterned therein a first metal trace and a second metal trace running linearly along a substantial length of a flexible substrate to form the respective flexible printed circuit structure, each of the first and second metal traces having a first end and a second end;

for each corresponding pair of electromagnet structures of the plurality of electromagnet structures on the assembly tray and flexible printed circuit structure of the plurality of flexible printed circuit structures in the assembly panel:

removing an electromagnet structure from the assembly tray and aligning the electromagnet structure with a corresponding flexible printed circuit structure with the first lead of the coil of the electromagnet structure positioned with the first end of the first metal trace of the corresponding flexible printed circuit structure and the second lead of the coil of the electromagnet structure positioned with the first end of the second metal trace of the corresponding flexible printed circuit structure;

electrically connecting the first lead of the coil of the electromagnet structure to the first end of the first metal trace of the corresponding flexible printed circuit structure;

electrically connecting the second lead of the coil of the electromagnet structure to the first end of the second metal trace of the corresponding flexible printed circuit structure;

positioning corresponding ancillary circuitry on the corresponding flexible printed circuit structure at an opposite end from the electromagnet structure; and electrically connecting the corresponding ancillary circuitry to the second end of the first metal trace of the corresponding flexible printed circuit structure and to the second end of the second metal trace of the corresponding flexible printed circuit structure.

26. The method of claim 25, wherein the arranging of the plurality of electromagnet structures on the assembly tray includes:

positioning an orientation of each of the plurality of electromagnet structures substantially similar to one another.

27. The method of claim 25, wherein the forming of the assembly panel of plurality of flexible printed circuit structures includes:

forming each of the plurality of flexible printed circuit structures in the assembly panel with a substantially similar orientation.

28. A system, comprising:

a medical instrument having a first portion and a second portion with the first portion configured for insertion into a body of a patient, the medical instrument including:

a flexible printed circuit having a length, the flexible printed circuit including:

a first metal trace running substantially along the length of the flexible printed circuit, the first metal trace having a first end in the first portion of the medical instrument and a second end in the second portion of the medical instrument;

a first contact pad electrically coupled to the first end of the first metal trace;

a second metal trace running substantially along the length of the flexible printed circuit, the second metal trace having a first end in the first portion of the medical instrument and a second end in the second portion of the medical instrument; and a second contact pad electrically coupled to the first end of the second metal trace;

an electromagnet structure in the first portion of the medical instrument, the electromagnet structure including:

a core;

a first lead contact electrically coupled to the first contact pad;

a second lead contact electrically coupled to the second contact pad; and a conductive coil wound around the core with a first end of the conductive coil electrically coupled to the first lead contact and a second end of the conductive coil electrically coupled to the second lead contact; and ancillary circuitry arranged in the second portion of the medical instrument and electrically coupled to the second end of the first metal trace and to the second end of the second metal trace, the ancillary circuitry configured to drive an excitation signal through the conductive coil via the first and second metal traces to generate a magnetic field about the electromagnet structure.

29. The system of claim 28, wherein the first lead contact, the second lead contact, and the conductive coil are configured from a wire wound around the core with the conductive coil disposed between the first and second lead contacts.

30. The system of claim 29, wherein the wire wound around the core for the first lead contact has a first pitch, the wire wound around the core for the second lead contact has a second pitch, and the wire wound around the core for the conductive coil has a third pitch.

31. The system of claim 28, wherein the electromagnet structure further comprises:
 a first gap section between the first lead contact and the conductive coil; and
 a second gap section between the second lead contact and the conductive coil.

32. The system of claim 31, wherein the electromagnet structure further comprises:
 a wire wound around the core to form the first and second lead contacts, the first and second gap sections and the conductive coil, wherein the wound wire for the first and second lead contacts and the conductive coil have a first pitch, and wherein the wound wire for the first and second gap sections have a second pitch that is higher than the first pitch.

33. A method to make a medical device, comprising:
 forming an electromagnet structure by winding a wire-like conductor around a core to form a first lead contact, a second lead contact, a conductive coil disposed between the first lead contact and the second lead contact, a first gap section disposed between the first lead contact and the conductive coil, and a second gap section disposed between the conductive coil and the second lead contact;
 forming a flexible printed circuit structure having a flexible substrate and patterned therein a first metal trace, a second metal trace, a first contact pad, and a second contact pad, the first and second metal traces having a first end and a second end and running linearly along a length of the flexible substrate, the first end of the first metal trace being electrically coupled to the first contact pad, and the first end of the second metal trace being electrically coupled to the second contact pad;
 aligning the electromagnet structure with the flexible printed circuit structure, the aligning including aligning first lead contact of the electromagnet structure with the first contact pad of the flexible printed circuit structure and aligning the second lead contact of the electromagnet structure with the second contact pad of the flexible printed circuit structure;
 electrically connecting the first lead contact of the electromagnet structure to the first contact pad of the flexible printed circuit structure;
 electrically connecting the second lead contact of the electromagnet structure to the second contact pad of the flexible printed circuit structure;
 positioning ancillary circuitry on the flexible printed circuit structure at an opposite end from the electromagnet structure; and
 electrically connecting the ancillary circuitry to the second end of the first metal trace of the flexible printed circuit structure and to the second end of the second metal trace of the flexible printed circuit structure.

34. The method of claim 33, wherein forming the electromagnet structure comprises:
 winding the wire-like conductor around the core at a first pitch to form the first lead contact;
 winding the wire-like conductor around the core at a second pitch to form the first gap section, the second pitch being higher than the first pitch;
 winding the wire-like conductor around the core at a third pitch to form the conductive coil, the third pitch being lower than the second pitch;
 winding the wire-like conductor around the core at a fourth pitch to form the second gap section, the fourth pitch being higher than the third pitch; and
 winding the wire-like conductor around the core at a fifth pitch to form the second lead contact, the fifth pitch being lower than the fourth pitch.

* * * * *